US011124518B2

(12) United States Patent
Huang et al.

(10) Patent No.: US 11,124,518 B2
(45) Date of Patent: Sep. 21, 2021

(54) L,2-DIHYDRO-3H-PYRAZOLO [3,4-D ]PYRIMIDIN-3-ONE ANALOGS

(71) Applicant: Recurium IP Holdings, LLC, San Diego, CA (US)

(72) Inventors: Peter Qinhua Huang, San Diego, CA (US); Brant Clayton Boren, San Diego, CA (US); Kevin Duane Bunker, Escondido, CA (US); Hui Liu, San Diego, CA (US); Sunil Paliwal, Monroe Township, NJ (US)

(73) Assignee: Recurium IP Holdings, LLC, San Diego, CA (US)

( * ) Notice: Subject to any disclaimer, the term of this patent is extended or adjusted under 35 U.S.C. 154(b) by 0 days.

(21) Appl. No.: 16/635,348

(22) PCT Filed: Jul. 31, 2018

(86) PCT No.: PCT/US2018/044580
§ 371 (c)(1),
(2) Date: Jan. 30, 2020

(87) PCT Pub. No.: WO2019/028008
PCT Pub. Date: Feb. 7, 2019

(65) Prior Publication Data
US 2020/0157112 A1    May 21, 2020

Related U.S. Application Data

(60) Provisional application No. 62/539,734, filed on Aug. 1, 2017.

(51) Int. Cl.
*C07D 487/04*  (2006.01)
*A61P 35/00*  (2006.01)
*A61P 35/02*  (2006.01)
*A61P 35/04*  (2006.01)
*C07D 519/00*  (2006.01)

(52) U.S. Cl.
CPC ............ *C07D 487/04* (2013.01); *A61P 35/00* (2018.01); *C07D 519/00* (2013.01)

(58) Field of Classification Search
CPC ..... C07D 487/04; C07D 519/00; A61P 35/00; A61P 35/04; A61P 35/02
See application file for complete search history.

(56) References Cited

U.S. PATENT DOCUMENTS 8,329,711 B2    12/2012    Furuyama et al.

FOREIGN PATENT DOCUMENTS

WO    WO 2006/074985    7/2006
WO    WO 2007/126122    11/2007

OTHER PUBLICATIONS

International Preliminary Report on Patentability dated Feb. 4, 2020 for PCT Application No. PCT/US2018/044580, filed Jul. 31, 2018.
International Search Report and Written Opinion dated Sep. 4, 2018 for PCT Application No. PCT/US2018/044580, filed Jul. 31, 2018.

*Primary Examiner* — John M Mauro
(74) *Attorney, Agent, or Firm* — Knobbe Martens Olson & Bear LLP

(57) ABSTRACT

Compounds of Formula (I) are provided herein. Such compounds, as well as pharmaceutically acceptable salts and compositions thereof, are useful for treating diseases or conditions, including conditions characterized by excessive cellular proliferation, such as breast cancer.

22 Claims, No Drawings

1,2-DIHYDRO-3H-PYRAZOLO [3,4-D]PYRIMIDIN-3-ONE ANALOGS

INCORPORATION BY REFERENCE TO ANY PRIORITY APPLICATIONS

Any and all applications for which a foreign or domestic priority claim is identified, for example, in the Application Data Sheet or Request as filed with the present application, are hereby incorporated by reference under 37 CFR 1.57, and Rules 4.18 and 20.6, including U.S. Provisional Application No. 62/539,734, filed Aug. 1, 2017.

FIELD

The present application relates to compounds that are WEE1 inhibitors and methods of using them to treat conditions characterized by excessive cellular proliferation, such as cancer.

DESCRIPTION

WEE1 kinase plays a role in the G2-M cell-cycle checkpoint arrest for DNA repair before mitotic entry. Normal cells repair damaged DNA during G1 arrest. Cancer cells often have a deficient G1-S checkpoint and depend on a functional G2-M checkpoint for DNA repair. WEE1 is overexpressed in various cancer types.

SUMMARY

Some embodiments provide a compound of Formula (I), or a pharmaceutically acceptable salt thereof.

Some embodiments disclosed herein relate to a pharmaceutical composition that can include an effective amount of one or more of compounds of Formula (I), or a pharmaceutically acceptable salt thereof, and a pharmaceutically acceptable carrier, diluent, excipient or combination thereof.

Some embodiments described herein relate to a method for ameliorating and/or treating a cancer described herein that can include administering an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) to a subject having a cancer described herein. Other embodiments described herein relate to the use of an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) in the manufacture of a medicament for ameliorating and/or treating a cancer described herein. Still other embodiments described herein relate to an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) for ameliorating and/or treating a cancer described herein.

Some embodiments described herein relate to a method for inhibiting replication of a malignant growth or a tumor that can include contacting the growth or the tumor with an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof), wherein the malignant growth or tumor is due to a cancer described herein. Other embodiments described herein relate to the use of an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) in the manufacture of a medicament for inhibiting replication of a malignant growth or a tumor, wherein the malignant growth or tumor is due to a cancer described herein. Still other embodiments described herein relate to an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) for inhibiting replication of a malignant growth or a tumor, wherein the malignant growth or tumor is due to a cancer described herein.

Some embodiments described herein relate to a method for ameliorating or treating a cancer described herein that can include contacting a malignant growth or a tumor with an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) to a subject having a cancer described herein. Other embodiments described herein relate to the use of an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) in the manufacture of a medicament for ameliorating or treating a cancer described herein that can include contacting a malignant growth or a tumor, wherein the malignant growth or tumor is due to a cancer described herein. Still other embodiments described herein relate to an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) for ameliorating or treating a cancer described herein that can include contacting a malignant growth or a tumor, wherein the malignant growth or tumor is due to a cancer described herein.

Some embodiments described herein relate to a method for inhibiting the activity of WEE1 in a cell (for example, inhibiting the activity of WEE1 in TP53-mutated cells, inhibiting the activity of WEE1 in TP53 wild-type cells, inhibiting the activity in WEE1 p53-deficient cells and/or decreasing the overexpression of WEE1 in cells) that can include providing an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) to a cancer cell from a cancer described herein. Other embodiments described herein relate to the use of an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) in the manufacture of a medicament for inhibiting the activity of WEE1 (for example, inhibiting the activity of WEE1 in TP53-mutated cells, inhibiting the activity of WEE1 in TP53 wild-type cells, inhibiting the activity in WEE1 p53-deficient cells and/or decreasing the overexpression of WEE1 in cells). Still other embodiments described herein relate to an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) for inhibiting the activity of WEE1 (for example, inhibiting the activity of WEE1 in TP53-mutated cells, inhibiting the activity of WEE1 in TP53 wild-type cells, inhibiting the activity in WEE1 p53-deficient cells and/or decreasing the overexpression of WEE1 in cells).

Some embodiments described herein relate to a method for ameliorating or treating a cancer described herein that can include inhibiting the activity of WEE1 (for example, inhibiting the activity of WEE1 in TP53-mutated cells, inhibiting the activity of WEE1 in TP53 wild-type cells, inhibiting the activity in WEE1 p53-deficient cells and/or decreasing the overexpression of WEE1 in cells) using an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof). Other embodiments described herein relate to the use of an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) in the manufacture of a medicament for ameliorating or treating a cancer described herein by inhibiting the activity of WEE1 (for example, inhibiting the activity of WEE1 in TP53-mutated cells, inhibiting the activity of WEE1 in TP53 wild-type cells, inhibiting the activity in WEE1 p53-deficient cells and/or decreasing the overexpression of WEE1 in cells). Still other embodiments described herein relate to an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) for ameliorating or treating a cancer described herein by inhibiting the activity of WEE1 (for example, inhibiting the activity of WEE1 in TP53-mutated cells, inhibiting the activity of WEE1 in TP53 wild-type cells, inhibiting the activity in WEE1 p53-deficient cells and/or decreasing the overexpression of WEE1 in cells).

DETAILED DESCRIPTION

WEE1 is a tyrosine kinase that is a critical component of the ATR-mediated G2 cell cycle checkpoint control that prevents entry into mitosis in response to cellular DNA damage. ATR phosphorylates and activates CHK1, which in turn activates WEE1, leading to the selective phosphorylation of cyclin-dependent kinase 1 (CDK1) at Tyr15, thereby stabilizing the CDK1-cyclin B complex and halting cell-cycle progression. This process confers a survival advantage by allowing tumor cells time to repair damaged DNA prior to entering mitosis. Inhibition of WEE1 abrogates the G2 checkpoint, promoting cancer cells with DNA damage to enter into unscheduled mitosis and undergo cell death via mitotic catastrophe. Therefore, WEE1 inhibition has the potential to sensitize tumors to DNA-damaging agents, such as cisplatin.

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

Whenever a group is described as being "optionally substituted" that group may be unsubstituted or substituted with one or more of the indicated substituents. Likewise, when a group is described as being "unsubstituted or substituted" if substituted, the substituent(s) may be selected from one or more the indicated substituents. If no substituents are indicated, it is meant that the indicated "optionally substituted" or "substituted" group may be substituted with one or more group(s) individually and independently selected from alkyl, alkenyl, alkynyl, cycloalkyl, cycloalkenyl, aryl, heteroaryl, heterocyclyl, aryl(alkyl), cycloalkyl (alkyl), heteroaryl(alkyl), heterocyclyl(alkyl), hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, nitro, sulfenyl, sulfinyl, sulfonyl, haloalkyl, haloalkoxy, an amino, a mono-substituted amine group, a di-substituted amine group, a mono-substituted amine(alkyl) and a di-substituted amine(alkyl).

As used herein, "$C_a$ to $C_b$" in which "a" and "b" are integers refer to the number of carbon atoms in a group. The indicated group can contain from "a" to "b", inclusive, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. If no "a" and "b" are designated, the broadest range described in these definitions is to be assumed.

If two "R" groups are described as being "taken together" the R groups and the atoms they are attached to can form a cycloalkyl, cycloalkenyl, aryl, heteroaryl or heterocycle. For example, without limitation, if $R^a$ and $R^b$ of an $NR^aR^b$ group are indicated to be "taken together," it means that they are covalently bonded to one another to form a ring:

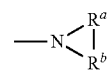

As used herein, the term "alkyl" refers to a fully saturated aliphatic hydrocarbon group. The alkyl moiety may be branched or straight chain. Examples of branched alkyl groups include, but are not limited to, iso-propyl, sec-butyl, t-butyl and the like. Examples of straight chain alkyl groups include, but are not limited to, methyl, ethyl, n-propyl, n-butyl, n-pentyl, n-hexyl, n-heptyl and the like. The alkyl group may have 1 to 30 carbon atoms (whenever it appears herein, a numerical range such as "1 to 30" refers to each integer in the given range; e.g., "1 to 30 carbon atoms"

means that the alkyl group may consist of 1 carbon atom, 2 carbon atoms, 3 carbon atoms, etc., up to and including 30 carbon atoms, although the present definition also covers the occurrence of the term "alkyl" where no numerical range is designated). The alkyl group may also be a medium size alkyl having 1 to 12 carbon atoms. The alkyl group could also be a lower alkyl having 1 to 6 carbon atoms. An alkyl group may be substituted or unsubstituted.

The term "alkenyl" used herein refers to a monovalent straight or branched chain radical of from two to twenty carbon atoms containing a carbon double bond(s) including, but not limited to, 1-propenyl, 2-propenyl, 2-methyl-1-propenyl, 1-butenyl, 2-butenyl and the like. An alkenyl group may be unsubstituted or substituted.

The term "alkynyl" used herein refers to a monovalent straight or branched chain radical of from two to twenty carbon atoms containing a carbon triple bond(s) including, but not limited to, 1-propynyl, 1-butynyl, 2-butynyl and the like. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused, bridged or spiro fashion. As used herein, the term "fused" refers to two rings which have two atoms and one bond in common. As used herein, the term "bridged cycloalkyl" refers to compounds wherein the cycloalkyl contains a linkage of one or more atoms connecting non-adjacent atoms. As used herein, the term "spiro" refers to two rings which have one atom in common and the two rings are not linked by a bridge. Cycloalkyl groups can contain 3 to 30 atoms in the ring(s), 3 to 20 atoms in the ring(s), 3 to 10 atoms in the ring(s), 3 to 8 atoms in the ring(s) or 3 to 6 atoms in the ring(s). A cycloalkyl group may be unsubstituted or substituted. Examples of mono-cycloalkyl groups include, but are in no way limited to, cyclopropyl, cyclobutyl, cyclopentyl, cyclohexyl, cycloheptyl and cyclooctyl. Examples of fused cycloalkyl groups are decahydronaphthalenyl, dodecahydro-1H-phenalenyl and tetradecahydroanthracenyl; examples of bridged cycloalkyl groups are bicyclo[1.1.1]pentyl, adamantanyl and norbornanyl; and examples of spiro cycloalkyl groups include spiro[3.3]heptane and spiro[4.5]decane.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). Cycloalkenyl groups can contain 3 to 10 atoms in the ring(s), 3 to 8 atoms in the ring(s) or 3 to 6 atoms in the ring(s). When composed of two or more rings, the rings may be connected together in a fused, bridged or spiro fashion. A cycloalkenyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group or a $C_6$ aryl group. Examples of aryl groups include, but are not limited to, benzene, naphthalene and azulene. An aryl group may be substituted or unsubstituted.

As used herein, "heteroaryl" refers to a monocyclic or multicyclic aromatic ring system (a ring system with fully delocalized pi-electron system) that contain(s) one or more heteroatoms (for example, 1, 2 or 3 heteroatoms), that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s), such as nine carbon atoms and one heteroatom; eight carbon atoms and two heteroatoms; seven carbon atoms and three heteroatoms; eight carbon atoms and one heteroatom; seven carbon atoms and two heteroatoms; six carbon atoms and three heteroatoms; five carbon atoms and four heteroatoms; five carbon atoms and one heteroatom; four carbon atoms and two heteroatoms; three carbon atoms and three heteroatoms; four carbon atoms and one heteroatom; three carbon atoms and two heteroatoms; or two carbon atoms and three heteroatoms. Furthermore, the term "heteroaryl" includes fused ring systems where two rings, such as at least one aryl ring and at least one heteroaryl ring or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsubstituted.

As used herein, "heterocyclyl" or "heteroalicyclyl" refers to three-, four-, five-, six-, seven-, eight-, nine-, ten-, up to 18-membered monocyclic, bicyclic and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The heteroatom(s) is an element other than carbon including, but not limited to, oxygen, sulfur and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused, bridged or spiro fashion. As used herein, the term "fused" refers to two rings which have two atoms and one bond in common. As used herein, the term "bridged heterocyclyl" or "bridged heteroalicyclyl" refers to compounds wherein the heterocyclyl or heteroalicyclyl contains a linkage of one or more atoms connecting non-adjacent atoms. As used herein, the term "spiro" refers to two rings which have one atom in common and the two rings are not linked by a bridge. Heterocyclyl and heteroalicyclyl groups can contain 3 to 30 atoms in the ring(s), 3 to 20 atoms in the ring(s), 3 to 10 atoms in the ring(s), 3 to 8 atoms in the ring(s) or 3 to 6 atoms in the ring(s). For example, five carbon atoms and one heteroatom; four carbon atoms and two heteroatoms; three carbon atoms and three heteroatoms; four carbon atoms and one heteroatom; three carbon atoms and two heteroatoms; two carbon atoms and three heteroatoms; one carbon atom and four heteroatoms; three carbon atoms and one heteroatom; or two carbon atoms and one heteroatom. Additionally, any nitrogens in a heteroalicyclic may be quaternized. Heterocyclyl or heteroalicyclic groups may be unsubstituted or substituted. Examples of such "heterocyclyl" or "heteroalicyclyl" groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3- oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, azepane, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone and their benzo-fused analogs (e.g., benzimidazolidinone, tetrahydroquinoline and/or 3,4-methylenedioxyphenyl). Examples of spiro heterocyclyl groups include 2-azaspiro[3.3]heptane, 2-oxaspiro[3.3]heptane, 2-oxa-6-azaspiro[3.3]heptane, 2,6-diazaspiro[3.3]heptane, 2-oxaspiro[3.4]octane and 2-azaspiro[3.4]octane.

As used herein, "aralkyl" and "aryl(alkyl)" refer to an aryl group connected, as a substituent, via a lower alkylene group. The lower alkylene and aryl group of an aralkyl may be substituted or unsubstituted. Examples include but are not limited to benzyl, 2-phenylalkyl, 3-phenylalkyl and naphthylalkyl.

As used herein, "heteroaralkyl" and "heteroaryl(alkyl)" refer to a heteroaryl group connected, as a substituent, via a lower alkylene group. The lower alkylene and heteroaryl group of heteroaralkyl may be substituted or unsubstituted. Examples include but are not limited to 2-thienylalkyl, 3-thienylalkyl, furylalkyl, thienylalkyl, pyrrolylalkyl, pyridylalkyl, isoxazolylalkyl and imidazolylalkyl and their benzo-fused analogs.

A "heteroalicyclyl(alkyl)" and "heterocyclyl(alkyl)" refer to a heterocyclic or a heteroalicyclic group connected, as a substituent, via a lower alkylene group. The lower alkylene and heterocyclyl of a (heteroalicyclyl)alkyl may be substituted or unsubstituted. Examples include but are not limited tetrahydro-2H-pyran-4-yl(methyl), piperidin-4-yl(ethyl), piperidin-4-yl(propyl), tetrahydro-2H-thiopyran-4-yl(methyl) and 1,3-thiazinan-4-yl(methyl).

As used herein, "lower alkylene groups" are straight-chained —CH$_2$-tethering groups, forming bonds to connect molecular fragments via their terminal carbon atoms. Examples include but are not limited to methylene (—CH$_2$—), ethylene (—CH$_2$CH$_2$—), propylene (—CH$_2$CH$_2$CH$_2$—) and butylene (—CH$_2$CH$_2$CH$_2$CH$_2$—). A lower alkylene group can be substituted by replacing one or more hydrogen of the lower alkylene group and/or by substituting both hydrogens on the same carbon with a cycloalkyl group

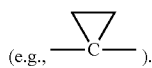

As used herein, the term "hydroxy" refers to a —OH group.

As used herein, "alkoxy" refers to the Formula —OR wherein R is an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl) is defined herein. A non-limiting list of alkoxys are methoxy, ethoxy, n-propoxy, 1-methylethoxy (isopropoxy), n-butoxy, iso-butoxy, sec-butoxy, tert-butoxy, phenoxy and benzoxy. An alkoxy may be substituted or unsubstituted.

As used herein, "acyl" refers to a hydrogen, alkyl, alkenyl, alkynyl, aryl, heteroaryl, heterocyclyl, aryl(alkyl), heteroaryl(alkyl) and heterocyclyl(alkyl) connected, as substituents, via a carbonyl group. Examples include formyl, acetyl, propanoyl, benzoyl and acryl. An acyl may be substituted or unsubstituted.

A "cyano" group refers to a "—CN" group.

The term "halogen atom" or "halogen" as used herein, means any one of the radio-stable atoms of column 7 of the Periodic Table of the Elements, such as, fluorine, chlorine, bromine and iodine.

A "thiocarbonyl" group refers to a "—C(=S)R" group in which R can be the same as defined with respect to O-carboxy. A thiocarbonyl may be substituted or unsubstituted.

An "O-carbamyl" group refers to a "—OC(=O)N(R$_A$R$_B$)" group in which R$_A$ and R$_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An O-carbamyl may be substituted or unsubstituted.

An "N-carbamyl" group refers to an "ROC(=O)N(R$_A$)—" group in which R and R$_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-carbamyl may be substituted or unsubstituted.

An "O-thiocarbamyl" group refers to a "—OC(=S)—N(R$_A$R$_B$)" group in which R$_A$ and R$_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An O-thiocarbamyl may be substituted or unsubstituted.

An "N-thiocarbamyl" group refers to an "ROC(=S)N(R$_A$)—" group in which R and R$_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-thiocarbamyl may be substituted or unsubstituted.

A "C-amido" group refers to a "—C(=O)N(R$_A$R$_B$)" group in which R$_A$ and R$_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). A C-amido may be substituted or unsubstituted.

An "N-amido" group refers to a "RC(=O)N(R$_A$)—" group in which R and R$_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-amido may be substituted or unsubstituted.

An "S-sulfonamido" group refers to a "—SO$_2$N(R$_A$R$_B$)" group in which R$_A$ and R$_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An S-sulfonamido may be substituted or unsubstituted.

An "N-sulfonamido" group refers to a "RSO$_2$N(R$_A$)—" group in which R and R$_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-sulfonamido may be substituted or unsubstituted.

An "O-carboxy" group refers to a "RC(=O)O—" group in which R can be hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein. An O-carboxy may be substituted or unsubstituted.

The terms "ester" and "C-carboxy" refer to a "—C(=O)OR" group in which R can be the same as defined with respect to O-carboxy. An ester and C-carboxy may be substituted or unsubstituted.

A "nitro" group refers to an "—NO$_2$" group.

A "sulfenyl" group refers to an "—SR" group in which R can be hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). A sulfenyl may be substituted or unsubstituted.

A "sulfinyl" group refers to an "—S(=O)—R" group in which R can be the same as defined with respect to sulfenyl. A sulfinyl may be substituted or unsubstituted.

A "sulfonyl" group refers to an "SO$_2$R" group in which R can be the same as defined with respect to sulfenyl. A sulfonyl may be substituted or unsubstituted.

As used herein, "haloalkyl" refers to an alkyl group in which one or more of the hydrogen atoms are replaced by a halogen (e.g., mono-haloalkyl, di-haloalkyl, tri-haloalkyl and polyhaloalkyl). Such groups include but are not limited to, chloromethyl, fluoromethyl, difluoromethyl, trifluoromethyl, 1-chloro-2-fluoromethyl, 2-fluoroisobutyl and pentafluoroethyl. A haloalkyl may be substituted or unsubstituted.

As used herein, "haloalkoxy" refers to an alkoxy group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy, 1-chloro-2-fluoromethoxy and 2-fluoroisobutoxy. A haloalkoxy may be substituted or unsubstituted.

The term "amino" as used herein refers to a —NH$_2$ group.

A "mono-substituted amine" group refers to a "—NHR$_A$" group in which R$_A$ can be an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein. The R$_A$ may be substituted or unsubstituted. Examples of mono-substituted amino groups include, but are not limited to, —NH(methyl), —NH(phenyl) and the like.

A "di-substituted amine" group refers to a "—NR$_A$R$_B$" group in which R$_A$ and R$_B$ can be independently an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein. R$_A$ and R$_B$ can independently be substituted or unsubstituted. Examples of di-substituted amino groups include, but are not limited to, —N(methyl)$_2$, —N(phenyl)(methyl), —N(ethyl)(methyl) and the like.

As used herein, "mono-substituted amine(alkyl)" group refers to a mono-substituted amine as provided herein connected, as a substituent, via a lower alkylene group. A mono-substituted amine(alkyl) may be substituted or unsubstituted. Examples of mono-substituted amine(alkyl) groups include, but are not limited to, —CH$_2$NH(methyl), —CH$_2$NH(phenyl), —CH$_2$CH$_2$NH(methyl), —CH$_2$CH$_2$NH(phenyl) and the like.

As used herein, "di-substituted amine(alkyl)" group refers to a di-substituted amine as provided herein connected, as a substituent, via a lower alkylene group. A di-substituted amine(alkyl) may be substituted or unsubstituted. Examples of di-substituted amine(alkyl)groups include, but are not limited to, —CH$_2$N(methyl)$_2$, —CH$_2$N(phenyl)(methyl), —NCH$_2$(ethyl)(methyl), —CH$_2$CH$_2$N(methyl)$_2$, —CH$_2$CH$_2$N(phenyl)(methyl), —NCH$_2$CH$_2$(ethyl)(methyl) and the like.

Where the number of substituents is not specified (e.g. haloalkyl), there may be one or more substituents present. For example, "haloalkyl" may include one or more of the same or different halogens. As another example, "C$_1$-C$_3$ alkoxyphenyl" may include one or more of the same or different alkoxy groups containing one, two or three atoms.

As used herein, a radical indicates species with a single, unpaired electron such that the species containing the radical can be covalently bonded to another species. Hence, in this context, a radical is not necessarily a free radical. Rather, a radical indicates a specific portion of a larger molecule. The term "radical" can be used interchangeably with the term "group."

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), a sulfuric acid, a nitric acid and a phosphoric acid (such as 2,3-dihydroxypropyl dihydrogen phosphate). Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluensulfonic, trifluoroacetic, benzoic, salicylic, 2-oxopentanedioic or naphthalenesulfonic acid. Pharmaceutical salts can also be obtained by reacting a compound with a base to form a salt such as an ammonium salt, an alkali metal salt, such as a sodium, a potassium or a lithium salt, an alkaline earth metal salt, such as a calcium or a magnesium salt, a salt of a carbonate, a salt of a bicarbonate, a salt of organic bases such as dicyclohexylamine, N-methyl-D-glucamine, tris(hydroxymethyl)methylamine, C$_1$-C$_7$ alkylamine, cyclohexylamine, triethanolamine, ethylenediamine and salts with amino acids such as arginine and lysine. For compounds of Formula (I), those skilled in the art understand that when a salt is formed by protonation of a nitrogen-based group (for example, NH$_2$), the nitrogen-based group can be associated with a positive charge (for example, NH$_2$ can become NH$_3^+$) and the positive charge can be balanced by a negatively charged counterion (such as Cl$^-$).

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched or a stereoisomeric mixture. In addition, it is understood that, in any compound described herein having one or more double bond(s) generating geometrical isomers that can be defined as E or Z, each double bond may independently be E or Z a mixture thereof. Likewise, it is understood that, in any compound described, all tautomeric forms are also intended to be included.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

It is understood that the methods and combinations described herein include crystalline forms (also known as polymorphs, which include the different crystal packing arrangements of the same elemental composition of a compound), amorphous phases, salts, solvates and hydrates. In some embodiments, the compounds described herein exist in solvated forms with pharmaceutically acceptable solvents such as water, ethanol or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol or the like. Hydrates are formed when the solvent is water or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein.

Where a range of values is provided, it is understood that the upper and lower limit, and each intervening value between the upper and lower limit of the range is encompassed within the embodiments.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; and use of terms like 'preferably,' 'preferred,' 'desired,' or 'desirable,' and words of similar meaning should not be understood as implying that certain features are critical, essential, or even important to the structure or function, but instead as merely intended to highlight alternative or additional features that may or may not be utilized in a particular embodiment. In addition, the term "comprising" is to be interpreted synonymously with the phrases "having at least" or "including at least". When used in the context of a compound, composition or device, the term "comprising" means that the compound, composition or device includes at least the recited features or components, but may also include additional features or components. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

Compounds

Some embodiments disclosed herein relate to a compound of Formula (I), or a pharmaceutically acceptable salt thereof, having the structure:

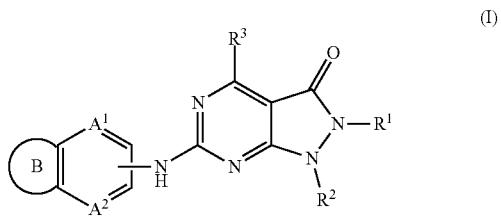

(I)

wherein $R^1$ can be selected from an optionally substituted $C_{1-4}$ alkyl, an optionally substituted $C_{2-4}$ alkenyl, an optionally substituted $C_{2-4}$ alkynyl, an optionally substituted $C_{3-6}$ cycloalkyl and an optionally substituted $C_{3-6}$ cycloalkyl($C_{1-4}$ alkyl), wherein when substituted, the $C_{1-4}$ alkyl, the $C_{2-4}$ alkenyl and the $C_{2-4}$ alkynyl can be independently substituted with one or more substituents selected from halogen, $C_{1-4}$ alkoxy, $C_{1-4}$ haloalkyl, $C_{1-4}$ haloalkoxy, cyano, amino, mono-$C_{1-4}$ alkyl amine and di-$C_{1-4}$ alkyl amine, and wherein the ring(s) of the $C_{3-6}$ cycloalkyl and the $C_{3-6}$ cycloalkyl ($C_{1-4}$ alkyl) can be independently substituted with one or more substituents selected from halogen, $C_{1-4}$ alkyl, $C_{1-4}$ alkoxy, $C_{1-4}$ haloalkyl, $C_{1-4}$ haloalkoxy, cyano, amino, mono-$C_{1-4}$ alkyl amine and di-$C_{1-4}$ alkyl amine; $R^2$ can be an optionally substituted aryl or an optionally substituted heteroaryl, wherein when the aryl or the heteroaryl are substituted, the aryl and the heteroaryl can be independently substituted with one or more substituents selected from an unsubstituted $C_{1-4}$ alkyl and

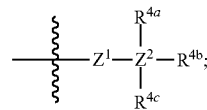

$R^3$ can be hydrogen or an unsubstituted $C_{1-4}$ alkyl; $A^1$ can be $CR^{6A}$ or N (nitrogen); $A^2$ can be $CR^{6B}$ or N (nitrogen); $Z^1$ can be a single bond, —C(═O)— or an optionally substituted $C_{1-6}$ alkylene group, wherein one or two more methylene groups constituting the optionally substituted $C_{1-6}$ alkylene group can be independently optionally replaced by an oxygen atom or carbonyl group, and wherein when the $C_{1-6}$ alkylene group is substituted, one or more methylene group can be independently substituted with an unsubstituted $C_{1-6}$ alkyl group; $Z^2$ can be N (nitrogen) or C (carbon), and when $Z^2$ is N, then $R^{4c}$ is absent; $R^{4a}$ and $R^{4b}$ can be independently selected from hydrogen, halogen, cyano, hydroxy, an unsubstituted $C_{1-6}$ alkyl, an unsubstituted hydroxy($C_{1-6}$ alkyl), an unsubstituted alkoxy($C_{1-6}$ alkyl), an unsubstituted $C_{2-7}$ acyl, an unsubstituted —C-carboxy having 2-7 carbons, an unsubstituted —C-amido and an unsubstituted $C_{1-7}$ alkylsulfonyl; or $R^{4a}$ and $R^{4b}$ together can form an optionally substituted $C_{1-6}$ alkylene, wherein one or two more methylene groups constituting the $C_{1-6}$ alkylene group can be independently optionally replaced by an oxygen atom, a sulfur atom, a sulfinyl group, a sulfonyl group, a carbonyl group or —(NR$^5$)—, and wherein when the $C_{1-6}$ alkylene group is substituted, one or more methylene group can be independently substituted with a substituent selected from halogen and an unsubstituted $C_{1-6}$ alkyl; or $R^{4a}$ and $R^{4b}$ together with $Z^2$ can form an unsubstituted monocyclic $C_{3-6}$ cycloalkyl and an unsubstituted 4-, 5-, or 6-membered heterocyclyl; $R^{4c}$ can be selected from halogen, hydroxy, an unsubstituted $C_{1-6}$ alkyl and an unsubstituted hydroxy($C_{1-6}$ alkyl); $R^5$ can be hydrogen, an unsubstituted $C_{1-6}$ alkyl or an unsubstituted $C_{1-6}$ haloalkyl; $R^{6A}$ and $R^{6B}$ can be independently hydrogen, halogen or an unsubstituted $C_{1-4}$ alkyl; and Ring B can be an optionally substituted monocyclic $C_{5-7}$ cycloalkyl, an optionally substituted 5-7 membered monocyclic heterocyclyl or an optionally substituted 7-10 membered bicyclic heterocyclyl, wherein when Ring B is substituted, Ring B is substituted with one or more substituents selected from the group consisting of halogen, an optionally substituted $C_{1-6}$ alkyl, an optionally substituted $C_{1-6}$ haloalkyl, an optionally substituted $C_{3-6}$ cycloalkyl, an optionally substituted aryl, an optionally substituted heteroaryl, an optionally substituted heterocyclyl, an optionally substituted aryl($C_{1-6}$ alkyl), an optionally substituted heteroaryl($C_{1-6}$ alkyl), an optionally substituted heterocyclyl($C_{1-6}$ alkyl), an optionally substituted acyl, an optionally substituted -hydroxy($C_{1-6}$ alkyl), an optionally substituted —C-amido, an optionally substituted —C-amido($C_{1-6}$ alkyl), an optionally substituted —N-amido, an optionally substituted —N-amido($C_{1-6}$ alkyl), an optionally substituted mono-substituted amine, an optionally substituted di-substituted amine, an optionally substituted mono-substituted amine ($C_{1-6}$ alkyl), an optionally substituted di-substituted amine ($C_{1-6}$ alkyl) and an optionally substituted sulfonyl. In some embodiments Ring B is substituted, is substituted with one or more substituents selected from an optionally substituted $C_{1-6}$ alkyl, an optionally substituted $C_{1-6}$ haloalkyl, an optionally substituted $C_{3-6}$ cycloalkyl, an optionally substituted heterocyclyl($C_{1-6}$ alkyl), an optionally substituted acyl, an optionally substituted —C-amido($C_{1-6}$ alkyl), an optionally substituted —N-amido, an optionally substituted mono-substituted amine, an optionally substituted di-substituted amine, an optionally substituted mono-substituted amine ($C_{1-6}$ alkyl), an optionally substituted di-substituted amine ($C_{1-6}$ alkyl) and an optionally substituted sulfonyl.

In some embodiment, $R^1$ can be an optionally substituted $C_{1-4}$ alkyl, such as an optionally substituted version of the following: methyl, ethyl, n-propyl, iso-propyl, n-butyl, iso-butyl and tert-butyl. In some embodiment, $R^1$ can be an unsubstituted $C_{1-4}$ alkyl. In other embodiments, $R^1$ can be an optionally substituted $C_{2-4}$ alkenyl. For example, $R^1$ can be a substituted or unsubstituted ethenyl, a substituted or unsubstituted propenyl or a substituted or unsubstituted butenyl. In still other embodiments, $R^1$ can be an optionally substituted $C_{2-4}$ alkynyl, such as a substituted or unsubstituted ethynyl, a substituted or unsubstituted propynyl or a substituted or unsubstituted butynyl. In yet still other embodiments, $R^1$ can be an optionally substituted $C_{3-6}$ cycloalkyl. For example, $R^1$ can be an optionally substituted monocyclic cyclopropyl, an optionally substituted monocyclic cyclobutyl, an optionally substituted monocyclic cyclopentyl, an optionally substituted monocyclic cyclohexyl, an optionally substituted bicyclic (fused, bridged or spiro) cyclopentyl, or an optionally substituted bicyclic (fused, bridged or spiro) cyclohexyl. In some embodiments, $R^1$ can be a substituted or unsubstituted bicyclo[1.1.1]pentyl. In some embodiments, $R^1$ can be a substituted or unsubstituted monocyclic cyclopropyl. In some embodiments, $R^1$ can be an optionally substituted $C_{3-6}$ cycloalkyl($C_{1-4}$ alkyl). Examples of suitable $C_{3-6}$ cycloalkyls that can be part of the optionally substituted $C_{3-6}$ cycloalkyl($C_{1-4}$ alkyl) are described herein, and include an optionally substituted monocyclic cyclopropyl, an optionally substituted monocyclic cyclobutyl, an optionally substituted monocyclic cyclopentyl, an optionally substituted monocyclic cyclohexyl, an optionally substituted bicyclic (fused, bridged or spiro) cyclopentyl, or an optionally substituted bicyclic (fused, bridged or spiro) cyclohexyl. For the ($C_{1-4}$ alkyl) of the optionally substituted $C_{3-6}$ cycloalkyl, $C_{1-4}$ alkyl can be methylene, ethylene, propylene or butylene, wherein each can be optionally substituted. In some embodiments, the ($C_{1-4}$ alkyl) of the optionally substituted $C_{3-6}$ cycloalkyl can be unsubstituted methylene, unsubstituted ethylene, unsubstituted propylene or unsubstituted butylene.

In some embodiment, $R^2$ can be an optionally substituted aryl, for example, $R^2$ can be an optionally substituted phenyl or an optionally substituted naphthyl. In other embodiments, $R^2$ can be an optionally substituted heteroaryl. The optionally substituted heteroaryl for $R^2$ can be monocyclic or bicyclic. In some embodiments, $R^2$ can be an optionally substituted monocyclic heteroaryl. Various heteroaryls can be present at $R^2$. In some embodiments, $R^2$ can be an optionally substituted monocyclic, nitrogen-containing heteroaryl. In some embodiments, $R^2$ can be substituted one substituent. In other embodiments, $R^2$ can be substituted two, three, four or five substituents. When substituted with multiple substituents, the substituents can be the same or different from each other.

In some embodiment, when $R^2$ is substituted, $R^2$ can be substituted with an unsubstituted $C_{1-4}$ alkyl. Examples of $C_{1-4}$ alkyls are described herein. In other embodiments, when $R^2$ is substituted, $R^2$ can be substituted with

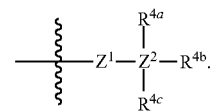

In some embodiments, $Z^1$ can be a single bond. In other embodiments, $Z^1$ can be —C(=O)—. In still other embodiments, $Z^1$ can be an optionally substituted $C_{1-6}$ alkylene group, wherein one or two more methylene groups constituting the optionally substituted $C_{1-6}$ alkylene group can be independently optionally replaced by an oxygen atom or carbonyl group, and wherein when the $C_{1-6}$ alkylene group is substituted, one or more methylene group can be independently substituted with an unsubstituted $C_{1-6}$ alkyl group. Various $C_{1-6}$ alkylene groups are known to those skilled in the art and include, but are not limited to, methylene, ethylene, propylene, butylene, pentylene and hexylene. Various $C_{1-6}$ alkyl groups are also known to those skilled in the art. Examples of $C_{1-6}$ alkyl groups are methyl, ethyl, n-propyl, iso-propyl, n-butyl, iso-butyl, tert-butyl, pentyl (straight-chained or branched) and hexyl (straight-chained or branched). In still other embodiments, $Z^1$ can be N (nitrogen). In some embodiments, $Z^2$ can be N (nitrogen). As provided herein, when $Z^2$ is N (nitrogen), then $R^{4c}$ is absent. In other embodiments, $Z^2$ can be C (carbon).

In some embodiments, $R^{4a}$ and $R^{4b}$ can be independently selected from hydrogen, halogen, cyano, hydroxy, an unsubstituted $C_{1-6}$ alkyl, an unsubstituted hydroxy($C_{1-6}$ alkyl), an unsubstituted alkoxy($C_{1-6}$ alkyl), an unsubstituted $C_{2-7}$ acyl, an unsubstituted —C-carboxy having 2-7 carbons, an unsubstituted —C-amido and an unsubstituted $C_{1-7}$ alkylsulfonyl. In some embodiments, $R^{4a}$ and $R^{4b}$ can be independently hydroxy or an unsubstituted $C_{1-6}$ alkyl. For example, one of $R^{4a}$ and $R^{4b}$ can be hydroxy, and the other of $R^{4a}$ and $R^{4b}$ can be an unsubstituted $C_{1-6}$ alkyl, such as methyl, ethyl, n-propyl, iso-propyl, n-butyl, iso-butyl, tert-butyl, pentyl (straight-chained or branched) and hexyl (straight-chained or branched). In some embodiments, one of $R^{4a}$ and $R^{4b}$ can be hydroxy, and the other of $R^{4a}$ and $R^{4b}$ can be methyl. In other embodiments, $R^{4a}$ and $R^{4b}$ can be independently an unsubstituted $C_{1-6}$ alkyl or an unsubstituted hydroxy($C_{1-6}$ alkyl). In still other embodiments, $R^{4a}$ and $R^{4b}$ can be independently an unsubstituted $C_{1-6}$ alkyl or an unsubstituted $C_{1-7}$ alkylsulfonyl. As one example, one of $R^{4a}$ and $R^{4b}$ can be an unsubstituted $C_{1-6}$ alkyl (such as methyl) and the other of $R^{4a}$ and $R^{4b}$ can be an unsubstituted $C_{1-7}$ alkylsulfonyl (such as an unsubstituted methyl-sulfenyl). In still other embodiments, $R^{4a}$ and $R^{4b}$ can be each an unsubstituted $C_{1-6}$ alkyl. In some embodiments, $R^{4a}$ and $R^{4b}$ can be each methyl. In some embodiments, $R^{4a}$ and $R^{4b}$ can together form an optionally substituted $C_{1-6}$ alkylene, wherein one or two more methylene groups constituting the $C_{1-6}$ alkylene group can be independently optionally replaced by an oxygen atom, a sulfur atom, a sulfinyl group, a sulfonyl group, a carbonyl group or —(NR$^5$)—, and wherein when the $C_{1-6}$ alkylene group is substituted, one or more methylene group can be independently substituted with a substituent selected from halogen and an unsubstituted $C_{1-6}$ alkyl. In other embodiments, $R^{4a}$ and $R^{4b}$ can together with $Z^2$ form an unsubstituted monocyclic $C_{3-6}$ cycloalkyl and an unsubstituted 4-, 5-, or 6-membered heterocyclyl. Examples of monocyclic $C_{3-6}$ cycloalkyls are cyclopropyl, cyclobutyl, cyclopentyl and cyclohexyl. Examples of an unsubstituted 4-, 5-, or 6-membered heterocyclyl include, but are not limited to, azetidinyl, morpholinyl, piperazinyl and piperidyl.

In some embodiments, including those in the paragraph above, $R^{4c}$ can be selected from halogen, hydroxy, an unsubstituted $C_{1-6}$ alkyl and an unsubstituted hydroxy($C_{1-6}$ alkyl). For example, when $R^{4c}$ is halogen, $R^{4c}$ can be F, Cl, Br or I. In some embodiments, including those in the paragraph above, $R^{4c}$ can be hydroxy. In other embodiments, including those in the paragraph above, $R^{4c}$ can be an unsubstituted $C_{1-6}$ alkyl. Examples of $C_{1-6}$ alkyls are described herein. In some embodiments, including those in the paragraph above, $R^{4c}$ can be methyl. In still other embodiments, including those in the paragraph above, $R^{4c}$ can be an unsubstituted hydroxy($C_{1-6}$ alkyl).

As described herein, $R^2$ can be substituted with

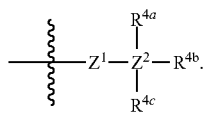

Examples of

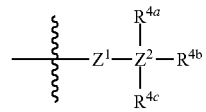

include, but are not limited to the following:

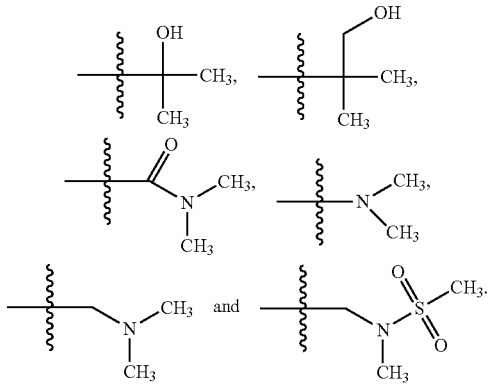

In some embodiments, $R^3$ can be hydrogen. In other embodiments, $R^3$ can be an unsubstituted $C_{1-4}$ alkyl. For example, $R^3$ can be methyl, ethyl, n-propyl, iso-propyl, n-butyl, iso-butyl and tert-butyl.

In some embodiments, $A^1$ can be $CR^{6A}$. In other embodiments, $A^1$ can be N (nitrogen). In some embodiments, including those of this paragraph, $A^2$ can be $CR^{6B}$. In other embodiments, $A^2$ can be N. In some embodiments, $R^{6A}$ can be hydrogen. In other embodiments, $R^{6A}$ can be halogen. In still other embodiments, $R^{6A}$ can be an unsubstituted $C_{1-4}$ alkyl. In some embodiments, $R^{6B}$ can be hydrogen. In other embodiments, $R^{6B}$ can be halogen. In still other embodiments, $R^{6B}$ can be an unsubstituted $C_{1-4}$ alkyl. Examples of suitable halogens and $C_{1-4}$ alkyls are described herein. In some embodiments, $A^1$ and $A^2$ can be each N. In other embodiments, $A^1$ can be CH; and $A^2$ can be CH. In still other embodiments, $A^1$ can be N; and $A^2$ can be $CR^{6B}$. In yet still other embodiments, $A^1$ can be $CR^{6A}$; and $A^2$ can be N.

In some embodiments, Ring B can be an optionally substituted monocyclic $C_{5-7}$ cycloalkyl. In other embodiments, Ring B can be an optionally substituted 5-7 membered monocyclic heterocyclyl. In still other embodiments, Ring B can be an optionally substituted 7-10 membered bicyclic heterocyclyl. In some embodiments, Ring B can be a substituted or unsubstituted monocyclic $C_5$ cycloalkyl. In other embodiments, Ring B can be a substituted or unsubstituted monocyclic $C_6$ cycloalkyl.

Examples of rings for Ring B include the following:

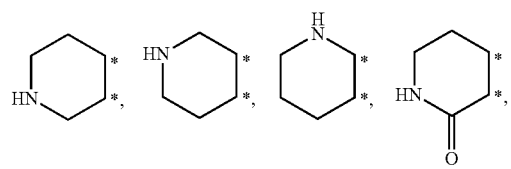

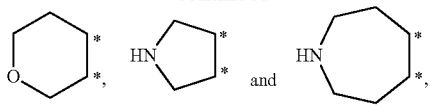

wherein the asterisks indicate the points of attachment to ring

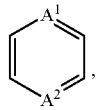

wherein each ring can be optionally substituted at a ring carbon, and wherein each ring can be optionally substituted at a ring nitrogen. When a ring nitrogen is substituted, the hydrogen of the ring NH group is replaced with a substituent.

Additional examples of rings for Ring B include the following:

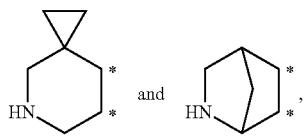 [SMILES: C1CNCC2(C1)CC2 ; C1CC2CC1CN2]

wherein the asterisks indicate the points of attachment to ring

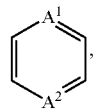

wherein each ring can be optionally substituted at a ring carbon, and wherein each ring can be optionally substituted at a ring nitrogen. When a ring nitrogen is substituted, the hydrogen of the ring NH group is replaced with a substituent.

When Ring B is substituted, any of the hydrogens attached to Ring B can be replaced with a substituent listed for "optionally substituted" including any hydrogen attached to a nitrogen. In some embodiments, the nitrogen of Ring B can be substituted. In some embodiments, at least one carbon of Ring B can be substituted. In some embodiments, one carbon of Ring B can be substituted. In some embodiments, Ring B can be substituted at one position. In other embodiments, Ring B can be substituted at two positions. In still other embodiments, Ring B can be substituted at three positions. In other embodiments, Ring B can be unsubstituted.

In some embodiments Ring B is substituted with one or more substituents selected from halogen, an optionally substituted $C_{1-6}$ alkyl, an optionally substituted $C_{1-6}$ haloalkyl, an optionally substituted $C_{3-6}$ cycloalkyl, an optionally substituted aryl, an optionally substituted heteroaryl, an optionally substituted heterocyclyl, an optionally substituted aryl($C_{1-6}$ alkyl), an optionally substituted heteroaryl($C_{1-6}$ alkyl), an optionally substituted heterocyclyl($C_{1-6}$ alkyl), an optionally substituted acyl, an optionally substituted -hydroxy($C_{1-6}$ alkyl), an optionally substituted —C-amido, an optionally substituted —C-amido($C_{1-6}$ alkyl), an optionally substituted —N-amido, an optionally substituted —N-amido($C_{1-6}$ alkyl), an optionally substituted mono-substituted amine, an optionally substituted di-substituted amine, an optionally substituted mono-substituted amine($C_{1-6}$ alkyl), an optionally substituted di-substituted amine($C_{1-6}$ alkyl) and an optionally substituted sulfonyl. In some embodiments Ring B is substituted, is substituted with one or more substituents selected from an optionally substituted $C_{1-6}$ alkyl, an optionally substituted $C_{1-6}$ haloalkyl, an optionally substituted $C_{3-6}$ cycloalkyl, an optionally substituted heterocyclyl($C_{1-6}$ alkyl), an optionally substituted acyl, an optionally substituted —C-amido($C_{1-6}$ alkyl), an optionally substituted —N-amido, an optionally substituted mono-substituted amine, an optionally substituted di-substituted amine, an optionally substituted mono-substituted amine($C_{1-6}$ alkyl), an optionally substituted di-substituted amine($C_{1-6}$ alkyl) and an optionally substituted sulfonyl. In some embodiments Ring B is substituted with one or more substituents selected from halogen, an unsubstituted $C_{1-6}$ alkyl, an unsubstituted $C_{1-6}$ haloalkyl, an unsubstituted $C_{3-6}$ cycloalkyl, an unsubstituted heterocyclyl($C_{1-6}$ alkyl), an unsubstituted acyl, an unsubstituted —C-amido($C_{1-6}$ alkyl), an unsubstituted mono-substituted amine, an unsubstituted di-substituted amine, an unsubstituted hydroxy($C_{1-6}$ alkyl), an unsubstituted mono-substituted amine($C_{1-6}$ alkyl), an unsubstituted di-substituted amine($C_{1-6}$ alkyl), a substituted —N-amido (wherein the substituted —N-amido can be —NH—C(=O)—$(CH_2)_{1-4}$—$NR^{7A}R^{7B}$, and $R^{7A}$ and $R^{7B}$ can be independently hydrogen or an unsubstituted $C_{1-6}$ alkyl) and an unsubstituted sulfonyl (wherein the unsubstituted sulfonyl can be —S(=O)$_2$— an unsubstituted $C_{1-4}$ alkyl).

In some embodiments, a compound of Formula (I) can have the structure of Formula (Ia), or a pharmaceutically acceptable salt thereof:

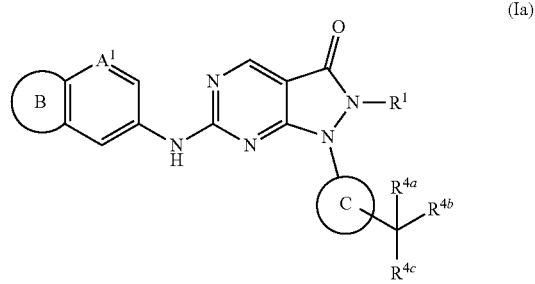

(Ia)

wherein: $R^1$ can be an unsubstituted alkenyl; Ring C can be a monocyclic heteroaryl; $R^{4a}$ can be hydroxy; $R^{4b}$ and $R^{4c}$ can be each an unsubstituted $C_{1-4}$ alkyl; $A^1$ can be CH or N; and Ring B can be an optionally substituted monocyclic $C_{5-7}$ cycloalkyl, an optionally substituted 5-7 membered monocyclic heterocyclyl or an optionally substituted 7-10 membered bicyclic heterocyclyl, wherein when Ring B is substituted, Ring B is substituted with one or more substituents selected from the group consisting of halogen, an unsubstituted $C_{1-6}$ alkyl, an unsubstituted $C_{1-6}$ haloalkyl, an unsubstituted $C_{3-6}$ cycloalkyl, an unsubstituted heterocyclyl($C_{1-6}$ alkyl), an unsubstituted acyl, an unsubstituted —C-amido ($C_{1-6}$ alkyl), an unsubstituted mono-substituted amine, an unsubstituted di-substituted amine, an unsubstituted hydroxy($C_{1-6}$ alkyl), an unsubstituted mono-substituted amine($C_{1-6}$ alkyl), an unsubstituted di-substituted amine ($C_{1-6}$ alkyl), a substituted —N-amido wherein the substituted —N-amido is —NH—C(=O)—$(CH_2)_{1-4}$—$NR^{7A}R^{7B}$, and $R^{7A}$ and $R^{7B}$ are independently hydrogen or an unsubstituted $C_{1-6}$ alkyl and an unsubstituted sulfonyl wherein the unsubstituted sulfonyl is —S(=O)$_2$— an unsubstituted $C_{1-4}$ alkyl-.

In some embodiments of Formula (Ia), $A^1$ can be CH. In some embodiments of Formula (Ia), $R^1$ is —$CH_2CH=CH_2$. In some embodiments of Formula (Ia), Ring C can be a nitrogen-containing monocyclic heteroaryl such as a pyridinyl. When Ring C is pyridinyl, Ring C and

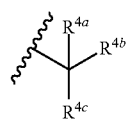

can have the following structure:

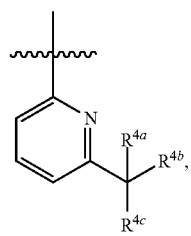

wherein $R^{4a}$ can be hydroxy; and $R^{4b}$ and $R^{4c}$ can be each an unsubstituted $C_{1-4}$ alkyl. In some embodiments of Formula (Ia), Ring B can be selected from

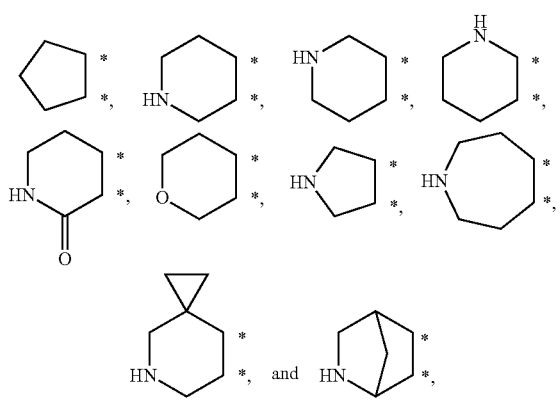

wherein the asterisks indicate the points of attachment to ring

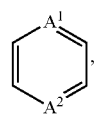

wherein each ring can be optionally substituted at a ring carbon, and wherein each ring can be optionally substituted at a ring nitrogen. As provided herein, Ring B can be unsubstituted or substituted with one or more substituents. For example, when Ring B is substituted, Ring B can be substituted with 1, 2 or 3 substituents.

In some embodiments, Ring B of Formulae (I) and (Ia) can be substituted with fluoro, chloro, methyl, ethyl, —$CF_3$, —$CHF_2$, —$CH_2CF_3$, —$CH_2CHF_2$, —$CH_2OH$, —$CH_2CH_2OH$, cyclopropyl, cyclobutyl, oxetanyl, —C(=O)$CH_3$, —S(=O)$_2CH_3$, —$CH_2$C(=O)N($CH_3$)$_2$, —$CH_2$C(=O)NH($CH_3$), —$CH_2CH_2$C(=O)N($CH_3$)$_2$, —$CH_2CH_2$C(=O)NH($CH_3$), —NH($CH_3$), —N($CH_3$)$_2$, —NHC(=O)$CH_2$NH($CH_3$), —NHC(=O)$CH_2$N($CH_3$)$_2$, —$CH_2$NH($CH_3$), —$CH_2CH_2$NH($CH_3$), —$CH_2$N($CH_3$)$_2$, —$CH_2CH_2$N($CH_3$)$_2$, —$CH_2$pyrrolidinyl and —$CH_2CH_2$pyrrolidinyl.

Examples of a compound of Formula (I) include:

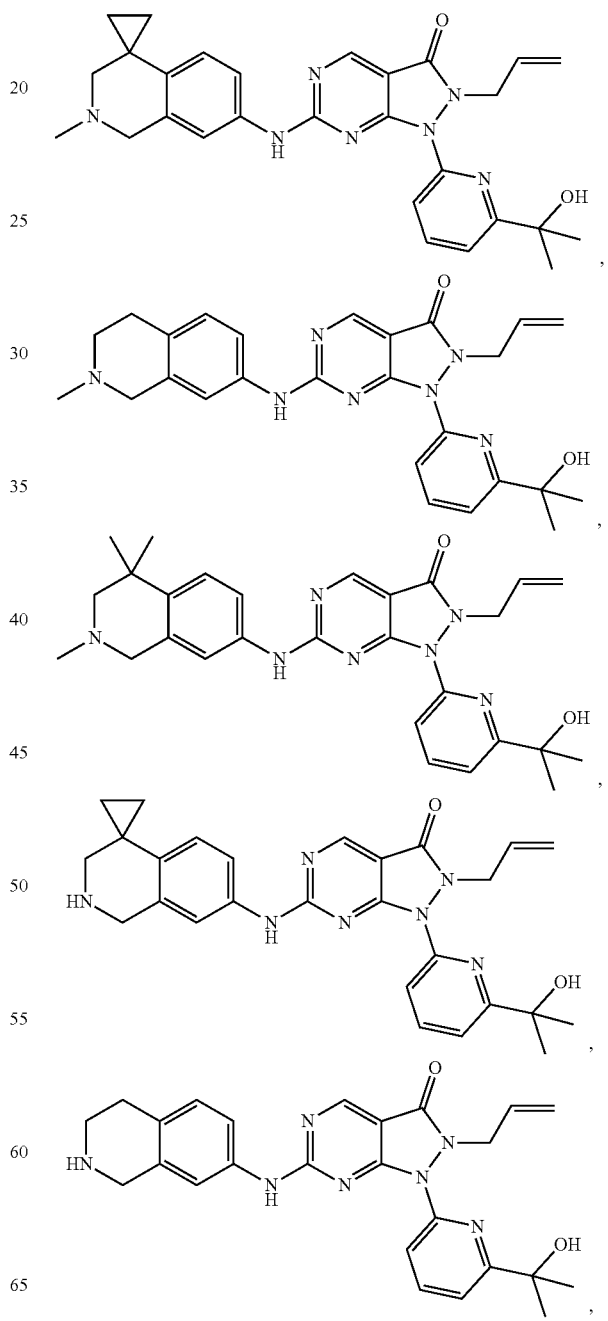

| 21 -continued | 22 -continued |
|---|---|
| 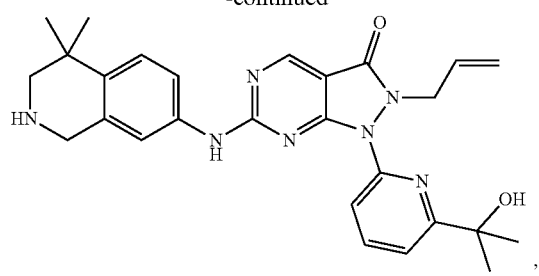 | 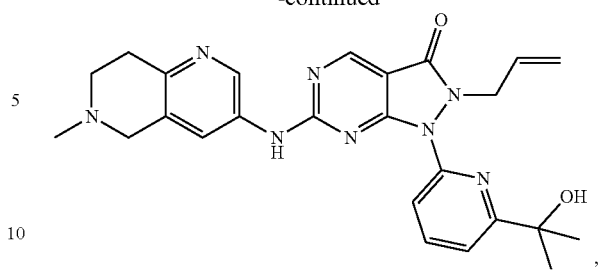 |
| 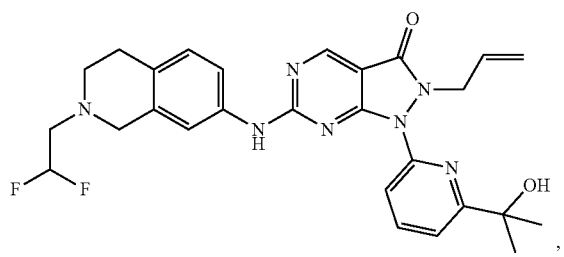 | 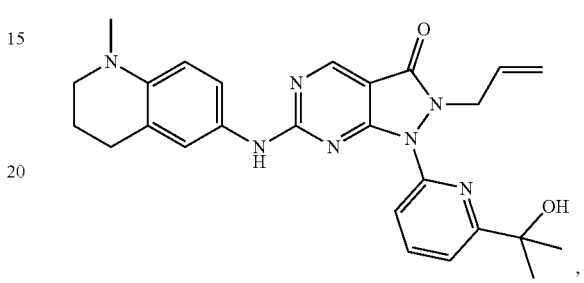 |
| 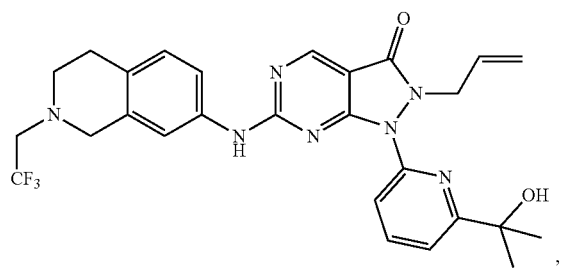 | 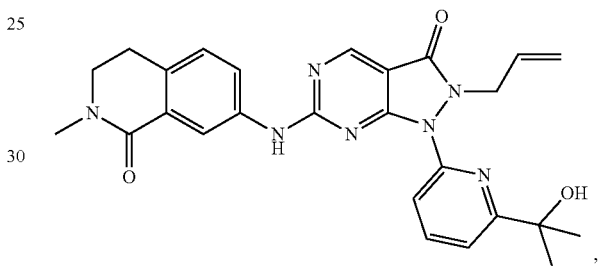 |
| 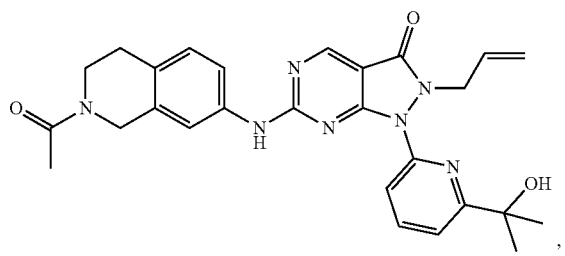 | 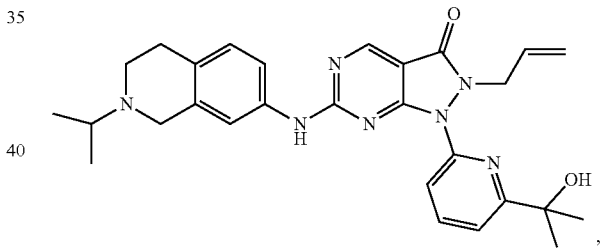 |
| 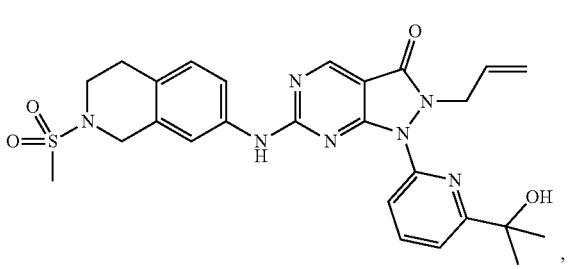 | 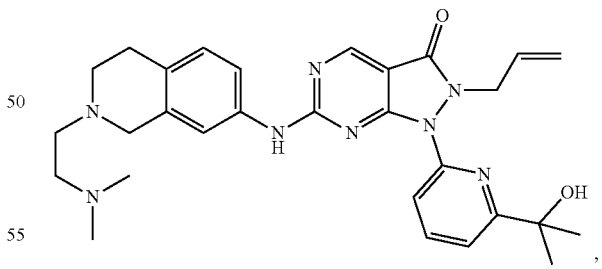 |
| 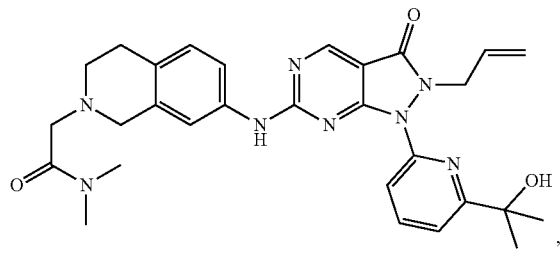 | 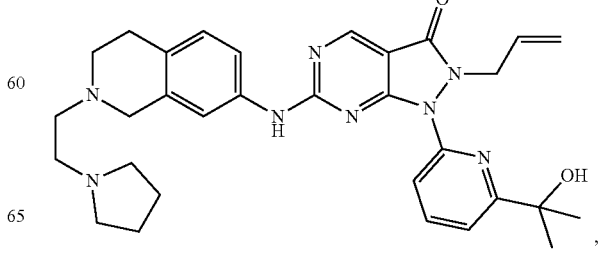 |

23
-continued
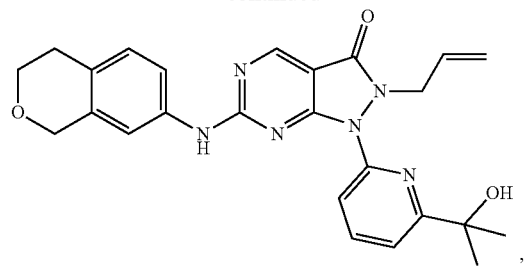,
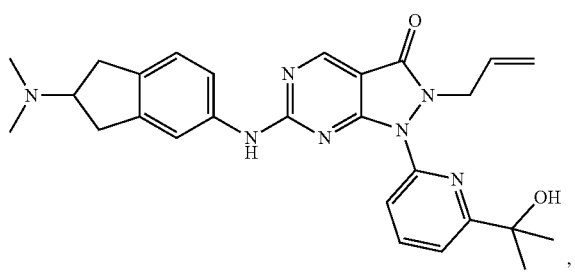,
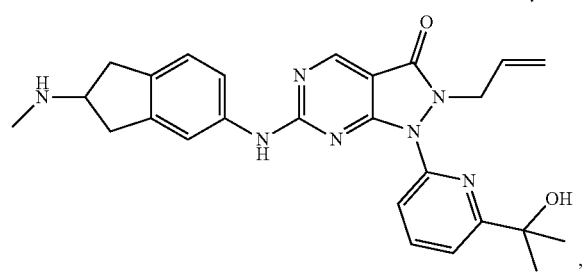,
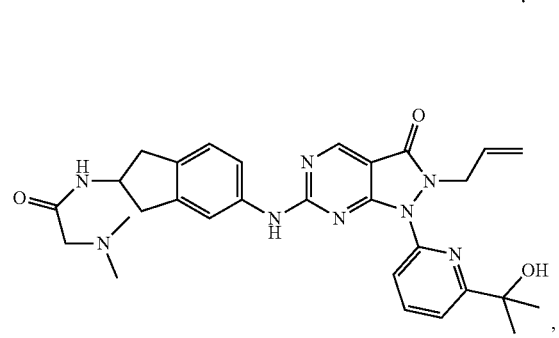,
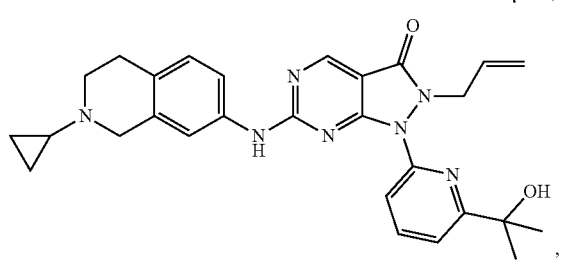,
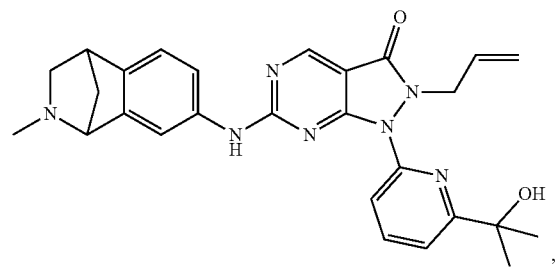,
24
-continued
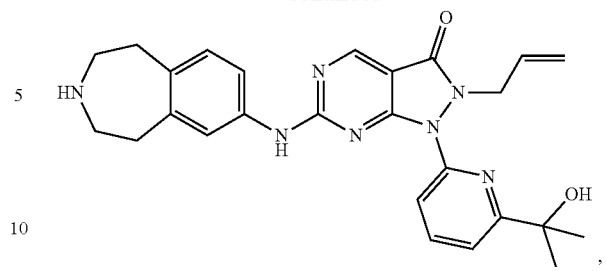,
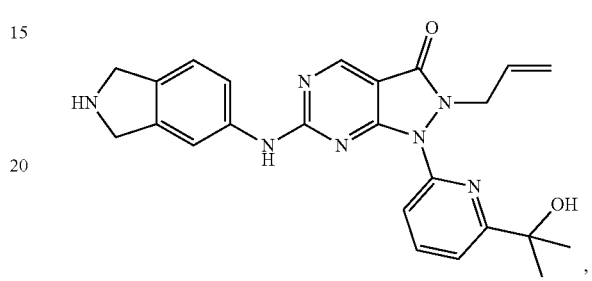,
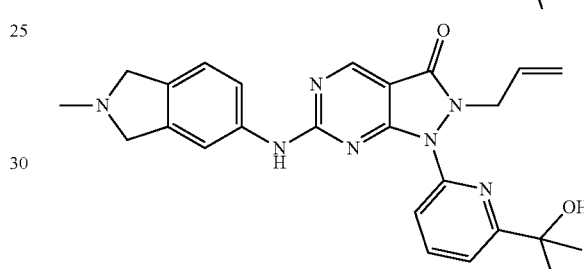,
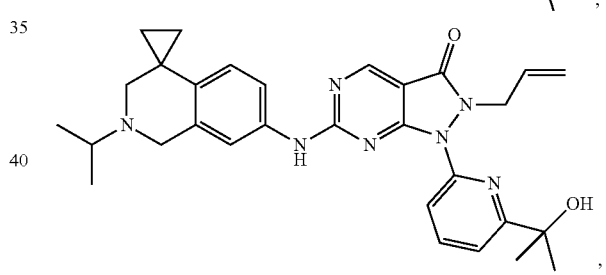,
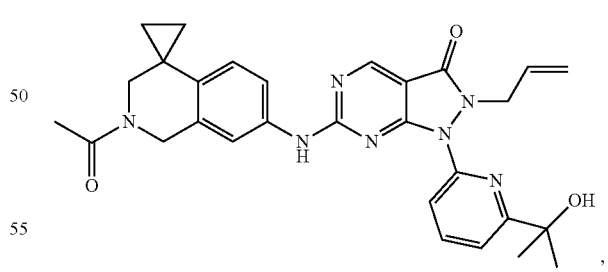,
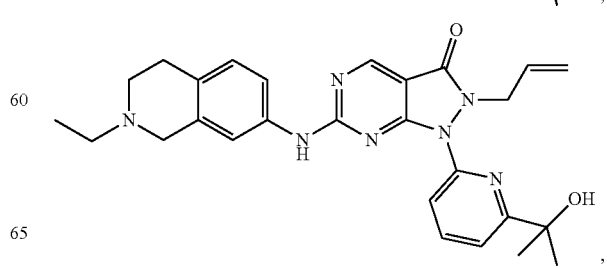,

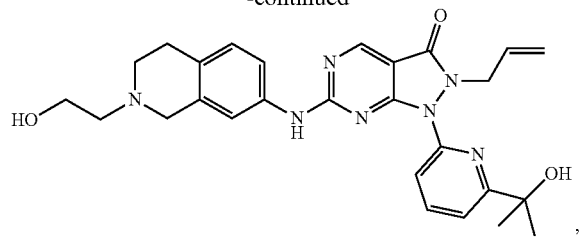
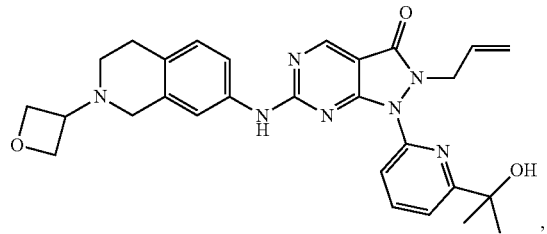
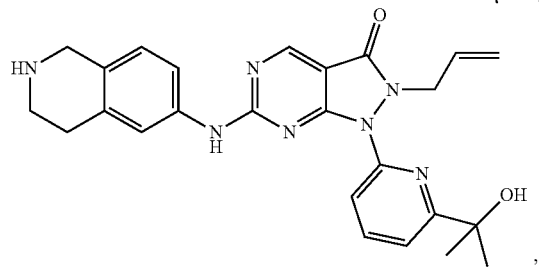
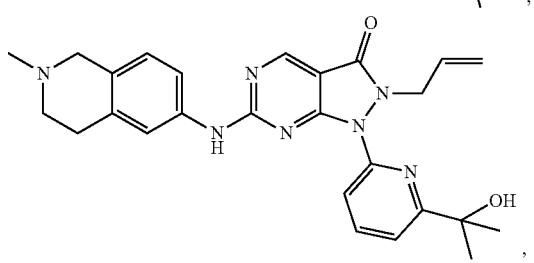
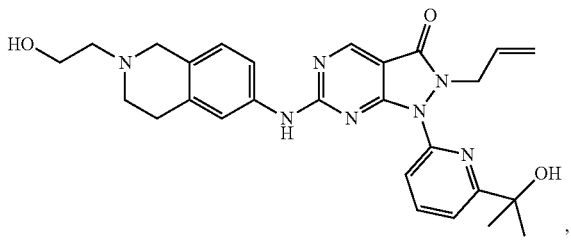
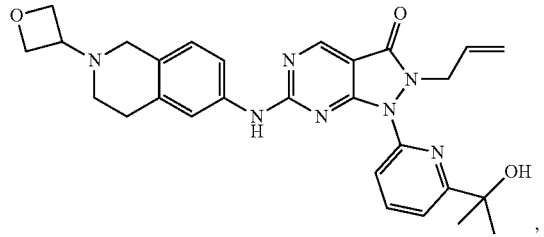
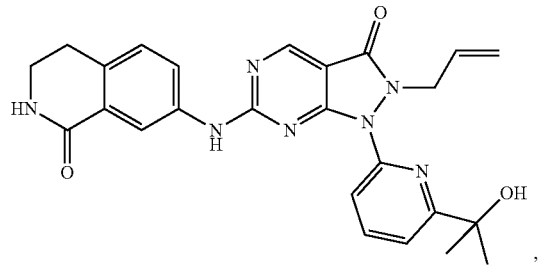
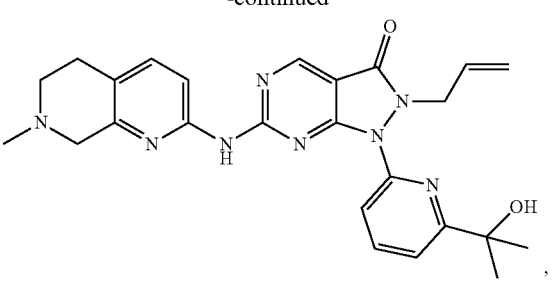
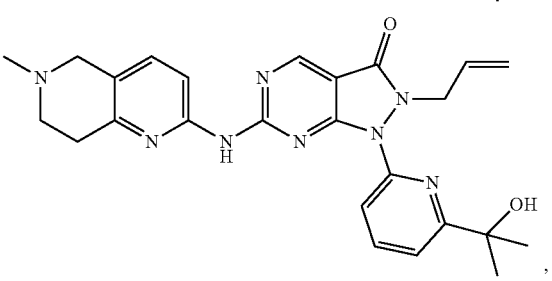
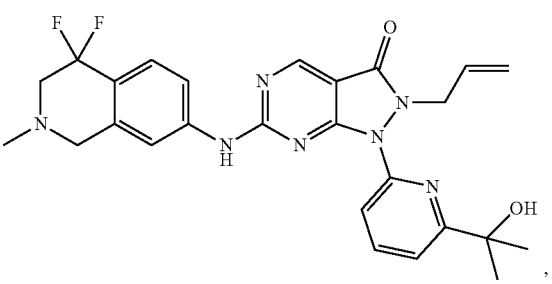
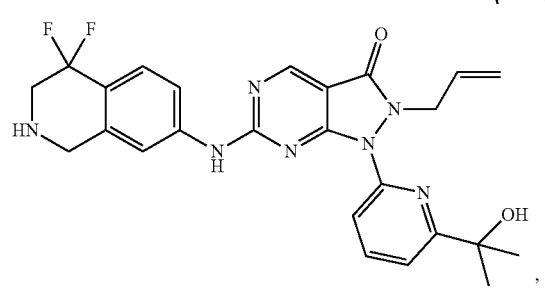
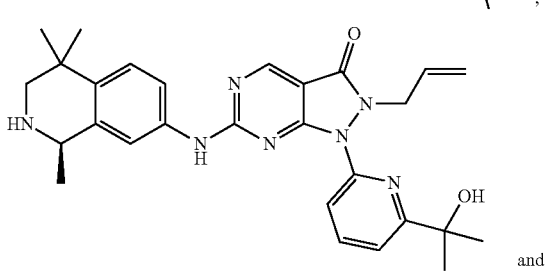
and
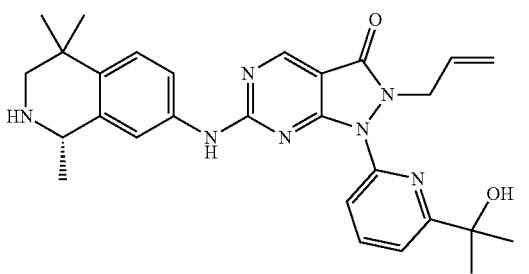
or a pharmaceutically acceptable salt of any of the foregoing.

Examples of compound of Formula (I) include the following:

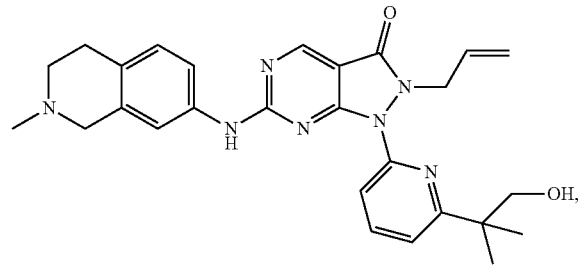

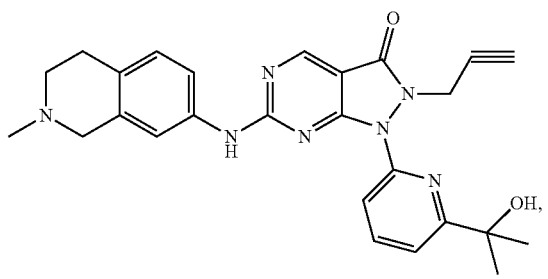

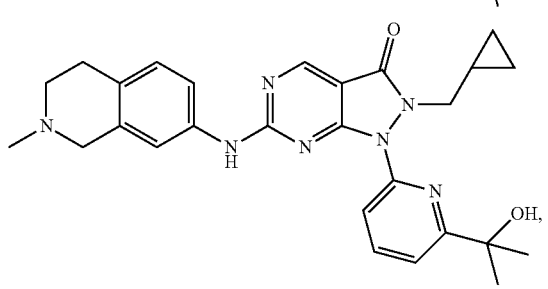

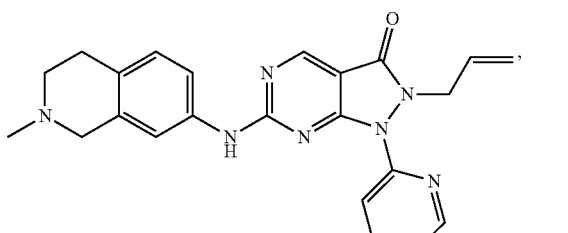

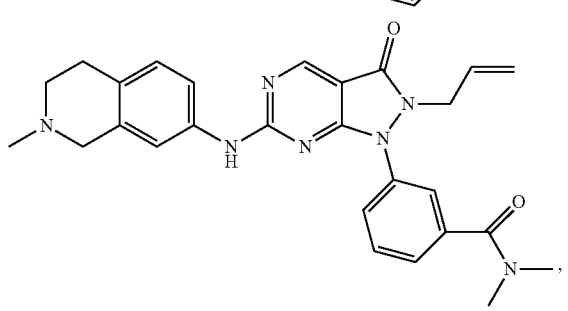

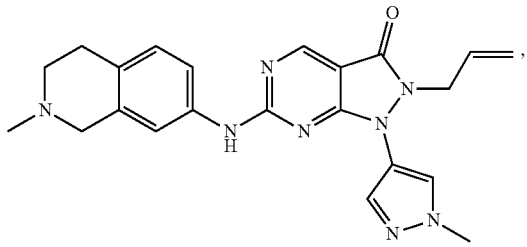

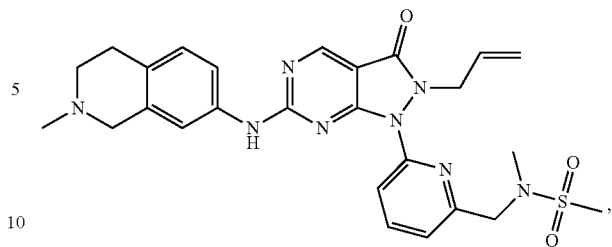

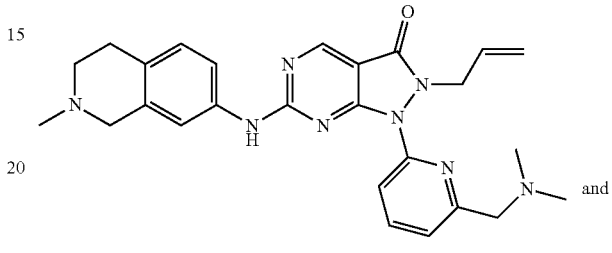

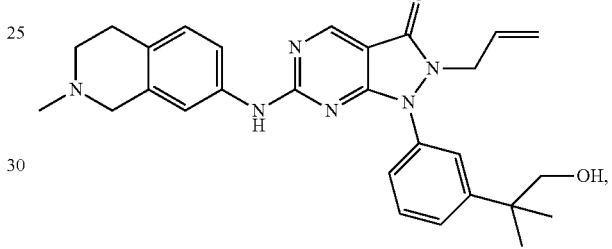

or a pharmaceutically acceptable salt of any of the foregoing.

Synthesis

Compounds of the Formula (I), or pharmaceutically acceptable salts thereof, can be made in various ways by those skilled using known techniques as guided by the detailed teachings provided herein. For example, in an embodiment, compounds of the Formula (I) are prepared in accordance with General Scheme 1 as shown herein.

In general, the coupling reaction reactions between compounds of the general Formulae A and B to form compounds of the Formula (I) as illustrated in General Scheme 1 can be carried out in a manner similar to the reactions as described herein in the Examples, by appropriate adjustment of the reagents and conditions described in the Examples. Any preliminary reaction steps required to form starting compounds of the general Formula A and B, or other precursors, can be carried out by those skilled in the art. In General Scheme 1, $A^1$, $A^2$, $R^1$, $R^2$, $R^3$ and Ring B can be as described herein.

General Scheme 1

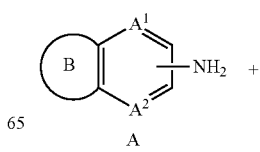

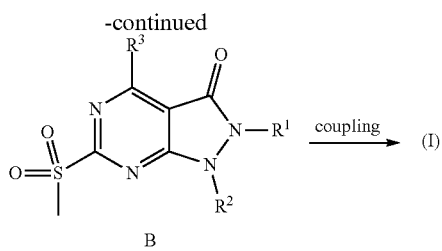

$$\text{B} \xrightarrow{\text{coupling}} \text{(I)}$$

Pharmaceutical Compositions

Some embodiments described herein relate to a pharmaceutical composition, that can include an effective amount of one or more compounds described herein (for example, a compound of Formula (I), or a pharmaceutically acceptable salt thereof) and a pharmaceutically acceptable carrier, diluent, excipient or combination thereof.

The term "pharmaceutical composition" refers to a mixture of one or more compounds and/or salts disclosed herein with other chemical components, such as diluents or carriers. The pharmaceutical composition facilitates administration of the compound to an organism. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, and salicylic acid. Pharmaceutical compositions will generally be tailored to the specific intended route of administration.

The term "physiologically acceptable" defines a carrier, diluent or excipient that does not abrogate the biological activity and properties of the compound nor cause appreciable damage or injury to an animal to which delivery of the composition is intended.

As used herein, a "carrier" refers to a compound that facilitates the incorporation of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks appreciable pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the pH and isotonicity of human blood.

As used herein, an "excipient" refers to an essentially inert substance that is added to a pharmaceutical composition to provide, without limitation, bulk, consistency, stability, binding ability, lubrication, disintegrating ability etc., to the composition. For example, stabilizers such as antioxidants and metal-chelating agents are excipients. In an embodiment, the pharmaceutical composition comprises an anti-oxidant and/or a metal-chelating agent. A "diluent" is a type of excipient.

The pharmaceutical compositions described herein can be administered to a human patient per se, or in pharmaceutical compositions where they are mixed with other active ingredients, as in combination therapy, or carriers, diluents, excipients or combinations thereof. Proper formulation is dependent upon the route of administration chosen. Techniques for formulation and administration of the compounds described herein are known to those skilled in the art.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. Additionally, the active ingredients are contained in an amount effective to achieve its intended purpose. Many of the compounds used in the pharmaceutical combinations disclosed herein may be provided as salts with pharmaceutically compatible counterions.

Multiple techniques of administering a compound, salt and/or composition exist in the art including, but not limited to, oral, rectal, pulmonary, topical, aerosol, injection, infusion and parenteral delivery, including intramuscular, subcutaneous, intravenous, intramedullary injections, intrathecal, direct intraventricular, intraperitoneal, intranasal and intraocular injections. In some embodiments, a compound of Formula (I), or a pharmaceutically acceptable salt thereof, can be administered orally.

One may also administer the compound, salt and/or composition in a local rather than systemic manner, for example, via injection or implantation of the compound directly into the affected area, often in a depot or sustained release formulation. Furthermore, one may administer the compound in a targeted drug delivery system, for example, in a liposome coated with a tissue-specific antibody. The liposomes will be targeted to and taken up selectively by the organ. For example, intranasal or pulmonary delivery to target a respiratory disease or condition may be desirable.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions that can include a compound and/or salt described herein formulated in a compatible pharmaceutical carrier may also be prepared, placed in an appropriate container, and labeled for treatment of an indicated condition.

Uses and Methods of Treatment

Some embodiments described herein relate to a method for ameliorating and/or treating a cancer described herein that can include administering an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) to a subject having a cancer described herein. Other embodiments described herein relate to the use of an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) in the manufacture of a medicament for ameliorating and/or treating a cancer described herein. Still other embodiments described herein relate to an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) for ameliorating and/or treating a cancer described herein.

Some embodiments described herein relate to a method for inhibiting replication of a malignant growth or a tumor that can include contacting the growth or the tumor with an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof), wherein the malignant growth or tumor is due to a cancer described herein. Other embodiments described herein relate to the use of an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) in the manufacture of a medicament for inhibiting replication of a malignant growth or a tumor, wherein the malignant growth or tumor is due to a cancer described herein. Still other embodiments described herein relate to an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) for inhibiting replication of a malignant growth or a tumor, wherein the malignant growth or tumor is due to a cancer described herein.

Some embodiments described herein relate to a method for ameliorating or treating a cancer described herein that can include contacting a malignant growth or a tumor with an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) to a subject having a cancer described herein. Other embodiments described herein relate to the use of an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) in the manufacture of a medicament for ameliorating or treating a cancer that can include contacting a malignant growth or a tumor, wherein the malignant growth or tumor is due to a cancer described herein. Still other embodiments described herein relate to an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) for ameliorating or treating a cancer that can include contacting a malignant growth or a tumor, wherein the malignant growth or tumor is due to a cancer described herein.

Some embodiments described herein relate to a method for inhibiting the activity of WEE1 (for example, inhibiting the activity of WEE1 in TP53-mutated cells, inhibiting the activity of WEE1 in TP53 wild-type cells, inhibiting the activity in WEE1 p53-deficient cells and/or decreasing the overexpression of WEE1 in cells) that can include providing an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) to a cancer cell from a cancer described herein. Other embodiments described herein relate to the use of an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) in the manufacture of a medicament for inhibiting the activity of WEE1 (for example, inhibiting the activity of WEE1 in TP53-mutated cells, inhibiting the activity of WEE1 in TP53 wild-type cells, inhibiting the activity in WEE1 p53-deficient cells and/or decreasing the overexpression of WEE1 in cells). Still other embodiments described herein relate to an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) for inhibiting the activity of WEE1 (for example, inhibiting the activity of WEE1 in TP53-mutated cells, inhibiting the activity of WEE1 in TP53 wild-type cells, inhibiting the activity in WEE1 p53-deficient cells and/or decreasing the overexpression of WEE1 in cells). Some embodiments described herein relate to a method for inhibiting the activity of WEE1 (for example, inhibiting the activity of WEE1 in TP53-mutated cells, inhibiting the activity of WEE1 in TP53 wild-type cells, inhibiting the activity in WEE1 p53-deficient cells and/or decreasing the overexpression of WEE1 in cells) that can include providing an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) to a cancer cell from a cancer described herein. Other embodiments described herein relate to a method for inhibiting the activity of WEE1 (for example, inhibiting the activity of WEE1 in TP53-mutated cells, inhibiting the activity of WEE1 in TP53 wild-type cells, inhibiting the activity in WEE1 p53-deficient cells and/or decreasing the overexpression of WEE1 in cells) that can include contacting a cancer cell from a cancer described herein with an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof), and thereby inhibiting the activity of WEE 1.

Some embodiments described herein relate to a method for ameliorating or treating a cancer described herein that can include inhibiting the activity of WEE1 (for example, inhibiting the activity of WEE1 in TP53-mutated cells, inhibiting the activity of WEE1 in TP53 wild-type cells, inhibiting the activity in WEE1 p53-deficient cells and/or decreasing the overexpression of WEE1 in cells) using an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof). Other embodiments described herein relate to the use of an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) in the manufacture of a medicament for ameliorating or treating a cancer described herein by inhibiting the activity of WEE1 (for example, inhibiting the activity of WEE1 in TP53-mutated cells, inhibiting the activity of WEE1 in TP53 wild-type cells, inhibiting the activity in WEE1 p53-deficient cells and/or decreasing the overexpression of WEE1 in cells). Still other embodiments described herein relate to an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) for ameliorating or treating a cancer described herein by inhibiting the activity of WEE1 (for example, inhibiting the activity of WEE1 in TP53-mutated cells, inhibiting the activity of WEE1 in TP53 wild-type cells, inhibiting the activity in WEE1 p53-deficient cells and/or decreasing the overexpression of WEE1 in cells). Some embodiments described herein relate to a method for ameliorating or treating a cancer described herein that can include contacting a cancer cell with an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof), wherein the compound inhibits the activity of WEE1 (for example, inhibiting the activity of WEE1 in TP53-mutated cells, inhibiting the activity of WEE1 in TP53 wild-type cells, inhibiting the activity in WEE1 p53-deficient cells and/or decreasing the overexpression of WEE1 in cells).

Some embodiments disclosed herein relate to a method for inhibiting the activity of WEE1 that can include providing an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) to a subject having a cancer described herein or a cancer cell from a cancer described herein. Other embodiments disclosed herein relate to the use of an effective amount of a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) in the manufacture of a medicament for inhibiting the activity of WEE1. Still other embodiments disclosed herein relate to a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) for inhibiting the activity of WEE 1.

Examples of suitable cancers include, but are not limited to: brain cancers, cervicocerebral cancers, esophageal cancers, thyroid cancers, small cell cancers, non-small cell cancers, breast cancers, lung cancers (for example non-small cell lung cancer and small cell lung cancer), stomach cancers, gallbladder/bile duct cancers, liver cancers, pancreatic cancers, colon cancers, rectal cancers, ovarian cancers, choriocarcinomas, uterus body cancers, uterocervical cancers, renal pelvis/ureter cancers, bladder cancers, prostate cancers, penis cancers, testicular cancers, fetal cancers, Wilms' cancer, skin cancers, malignant melanoma, neuroblastomas, osteosarcomas, Ewing's tumors, soft part sarcomas, acute leukemia, chronic lymphatic leukemias, chronic myelocytic leukemias, polycythemia vera, malignant lymphomas, multiple myeloma, Hodgkin's lymphomas, and non-Hodgkin's lymphomas.

As described herein, a cancer can become resistant to one or more anti-cancer agents. In some embodiments, a compound described herein (for example, a compound of Formula (I), or a pharmaceutically acceptable salt thereof) or a pharmaceutical composition that includes of a compound described herein (for example, a compound of Formula (I), or a pharmaceutically acceptable salt thereof) can be used to treat and/or ameliorate a cancer that has become resistant to one or more anti-cancer agents (such as one or more WEE1 inhibitors). Examples of anti-cancer agents that a subject may have developed resistance to include, but are not limited to, WEE1 inhibitors (such as AZD1775). In some embodiments, the cancer that has become resistant to one or more anti-cancer agents can be a cancer described herein.

Several known WEE1 inhibitors can cause one or more undesirable side effects in the subject being treated. Examples of undesirable side effects include, but are not limited to, thrombocytopenia, neutropenia, anemia, diarrhea, vomiting, nausea, abdominal pain, and constipation. In some embodiments, a compound described herein (for example, a compound of Formula (I), or a pharmaceutically acceptable salt thereof) can decrease the number and/or severity of one or more side effects associated with a known WEE1 inhibitor. In some embodiments, a compound of Formula (I), or a pharmaceutically acceptable salt thereof, can result in a severity of a side effect (such as one of those described herein) that is 25% less than compared to the severity of the same side effect experienced by a subject receiving a known WEE1 inhibitor (such as AZD1775, formally known as MK1775 (CAS No.: 955365-80-7, 2-allyl-1-(6-(2-hydroxypropan-2-yl)pyridin-2-yl)-6-(4-(4-methylpiperazin-1-yl)phenylamino)-1,2-dihydropyrazolo[3,4-d]pyrimidin-3-one)). In some embodiments, a compound of Formula (I), or a pharmaceutically acceptable salt thereof, results in a number of side effects that is 25% less than compared to the number of side effects experienced by a subject receiving a known WEE1 inhibitor (for example, AZD1775). In some embodiments, a compound of Formula (I), or a pharmaceutically acceptable salt thereof, results in a severity of a side effect (such as one of those described herein) that is less in the range of about 10% to about 30% compared to the severity of the same side effect experienced by a subject receiving a known WEE1 inhibitor (such as AZD1775) In some embodiments, a compound of Formula (I), or a pharmaceutically acceptable salt thereof, results in a number of side effects that is in the range of about 10% to about 30% less than compared to the number of side effects experienced by a subject receiving a known WEE1 inhibitor (for example, AZD1775).

The one or more compounds of Formula (I), or a pharmaceutically acceptable salt thereof, that can be used to treat, ameliorate and/or inhibit the growth of a cancer wherein inhibiting the activity of WEE1 is beneficial is provided in any of the embodiments described in paragraphs under the heading titled "Compounds." to the first full paragraph on page 26.

As used herein, a "subject" refers to an animal that is the object of treatment, observation or experiment. "Animal" includes cold- and warm-blooded vertebrates and invertebrates such as fish, shellfish, reptiles and, in particular, mammals. "Mammal" includes, without limitation, mice, rats, rabbits, guinea pigs, dogs, cats, sheep, goats, cows, horses, primates, such as monkeys, chimpanzees, and apes, and, in particular, humans. In some embodiments, the subject can be human. In some embodiments, the subject can be a child and/or an infant, for example, a child or infant with a fever. In other embodiments, the subject can be an adult.

As used herein, the terms "treat," "treating," "treatment," "therapeutic," and "therapy" do not necessarily mean total cure or abolition of the disease or condition. Any alleviation of any undesired signs or symptoms of the disease or condition, to any extent can be considered treatment and/or therapy. Furthermore, treatment may include acts that may worsen the subject's overall feeling of well-being or appearance.

The terms "therapeutically effective amount" and "effective amount" are used to indicate an amount of an active compound, or pharmaceutical agent, that elicits the biological or medicinal response indicated. For example, a therapeutically effective amount of compound, salt or composition can be the amount needed to prevent, alleviate or ameliorate symptoms of the disease or condition, or prolong the survival of the subject being treated. This response may occur in a tissue, system, animal or human and includes alleviation of the signs or symptoms of the disease or condition being treated. Determination of an effective amount is well within the capability of those skilled in the art, in view of the disclosure provided herein. The therapeutically effective amount of the compounds disclosed herein required as a dose will depend on the route of administration, the type of animal, including human, being treated and the physical characteristics of the specific animal under consideration. The dose can be tailored to achieve a desired effect, but will depend on such factors as weight, diet, concurrent medication and other factors which those skilled in the medical arts will recognize.

For example, an effective amount of a compound, or radiation, is the amount that results in: (a) the reduction, alleviation or disappearance of one or more symptoms caused by the cancer, (b) the reduction of tumor size, (c) the elimination of the tumor, and/or (d) long-term disease stabilization (growth arrest) of the tumor. In the treatment of lung cancer (such as non-small cell lung cancer) a therapeutically effective amount is that amount that alleviates or eliminates cough, shortness of breath and/or pain. As another example, an effective amount, or a therapeutically effective amount of an WEE1 inhibitor is the amount which results in the reduction in WEE1 activity and/or phosphorylation (such as phosphorylation of CDC2). The reduction in WEE1 activity is known to those skilled in the art and can be determined by the analysis of WEE1 intrinsic kinase activity and downstream substrate phosphorylation.

The amount of the compound of Formula (I), or a pharmaceutically acceptable salt thereof, required for use in treatment will vary not only with the particular compound or salt selected but also with the route of administration, the nature and/or symptoms of the disease or condition being treated and the age and condition of the patient and will be ultimately at the discretion of the attendant physician or clinician. In cases of administration of a pharmaceutically acceptable salt, dosages may be calculated as the free base. As will be understood by those of skill in the art, in certain situations it may be necessary to administer the compounds disclosed herein in amounts that exceed, or even far exceed, the dosage ranges described herein in order to effectively and aggressively treat particularly aggressive diseases or conditions.

In general, however, a suitable dose will often be in the range of from about 0.05 mg/kg to about 10 mg/kg. For example, a suitable dose may be in the range from about 0.10 mg/kg to about 7.5 mg/kg of body weight per day, such as about 0.15 mg/kg to about 5.0 mg/kg of body weight of the recipient per day, about 0.2 mg/kg to 4.0 mg/kg of body weight of the recipient per day, or any amount in between. The compound may be administered in unit dosage form; for example, containing 1 to 500 mg, 10 to 100 mg, 5 to 50 mg or any amount in between, of active ingredient per unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

As will be readily apparent to one skilled in the art, the useful in vivo dosage to be administered and the particular mode of administration will vary depending upon the age, weight, the severity of the affliction, the mammalian species treated, the particular compounds employed and the specific use for which these compounds are employed. The determination of effective dosage levels, that is the dosage levels necessary to achieve the desired result, can be accomplished by one skilled in the art using routine methods, for example, human clinical trials, in vivo studies and in vitro studies. For example, useful dosages of a compound of Formula (I), or pharmaceutically acceptable salts thereof, can be determined by comparing their in vitro activity, and in vivo activity in animal models. Such comparison can be done by comparison against an established drug, such as cisplatin and/or gemcitabine)

Dosage amount and interval may be adjusted individually to provide plasma levels of the active moiety which are sufficient to maintain the modulating effects, or minimal effective concentration (MEC). The MEC will vary for each compound but can be estimated from in vivo and/or in vitro data. Dosages necessary to achieve the MEC will depend on individual characteristics and route of administration. However, HPLC assays or bioassays can be used to determine plasma concentrations. Dosage intervals can also be determined using MEC value. Compositions should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration.

It should be noted that the attending physician would know how to and when to terminate, interrupt or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the disease or condition to be treated and to the route of administration. The severity of the disease or condition may, for example, be evaluated, in part, by standard prognostic evaluation methods. Further, the dose and perhaps dose frequency, will also vary according to the age, body weight and response of the individual patient. A program comparable to that discussed above may be used in veterinary medicine.

Compounds, salts and compositions disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, dogs or monkeys, may be determined using known methods. The efficacy of a particular compound may be established using several recognized methods, such as in vitro methods, animal models, or human clinical trials. When selecting a model to determine efficacy, the skilled artisan can be guided by the state of the art to choose an appropriate model, dose, route of administration and/or regime.

EXAMPLES

Additional embodiments are disclosed in further detail in the following examples, which are not in any way intended to limit the scope of the claims.

Intermediate 1

2-Allyl-1-(6-(2-hydroxypropan-2-yl)pyridin-2-yl)-6-(methylthio)-1,2-dihydro-3H-pyrazolo[3,4-d]pyrimidin-3-one

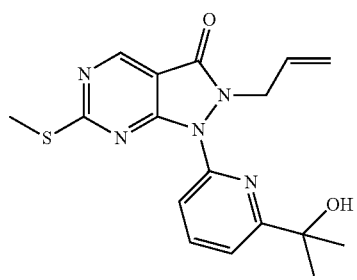 [SMILES: C=CCn1c(=O)c2cnc(SC)nc2n1-c1cccc(C(C)(C)O)n1]

Intermediate 1 was prepared according to WO 2008/133866 and Matheson et al., ACS Chemical Biology (2016) 11(4):921-930, which are hereby incorporated by reference for the limited purpose of the synthesis of Intermediate 1.

General Procedure A

Two Step Coupling Method

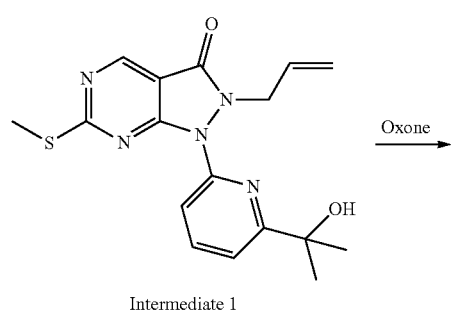

Intermediate 1

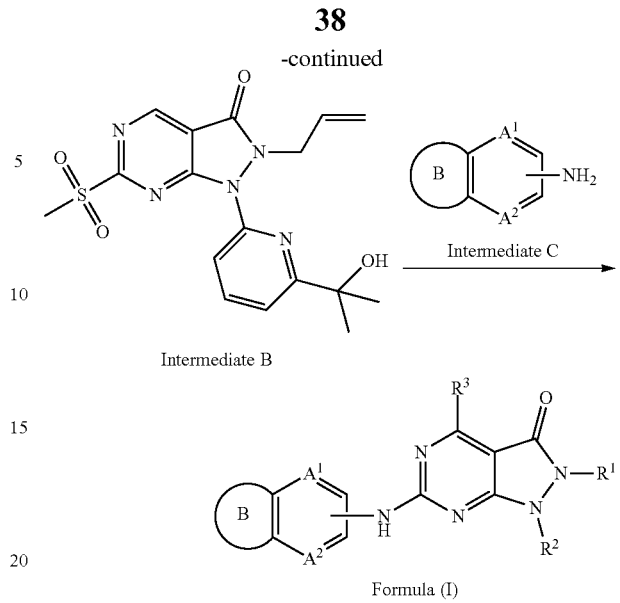

Intermediate B

Formula (I)

To a solution of Intermediate 1 (1 eq) in THF/Water (0.2 to 0.5 M) was added oxone (3 eq) at RT (room temperature), and the reaction was stirred for 1 h. The reaction was diluted with water and extracted with EA. The combined organic layers were dried ($Na_2SO_4$), filtered and concentrated in vacuo to afford Intermediate B as a pale yellow semi-solid. To a stirred solution of Intermediate B (1 eq) in toluene (0.3 to 0.5 M) was added DIPEA (3 eq) and Intermediate C (1 eq). The reaction was stirred at RT for 16 h. The reaction was diluted with water, extracted with EA, dried ($Na_2SO_4$), filtered and concentrated. The crude residue was purified by column chromatography or reverse phase HPLC to give Product Formula (I).

General Procedure B

One Pot Coupling Method

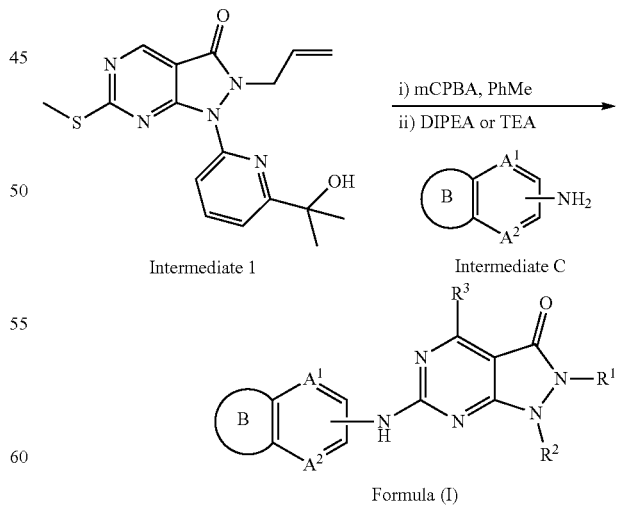

Formula (I)

To a solution of Intermediate 1 (1 eq) in toluene (0.2 to 0.5 M), was added mCPBA (2.0 eq). The reaction was stirred at RT for 1 h. DIPEA (5.0 eq) and the corresponding amine (1.0 eq) were added. The reaction was stirred at RT for 24 h.

NaHCO$_3$ was added, and the mixture was extracted 3× with EA. The combined organic extracts were washed with brine, dried (Na$_2$SO$_4$) and concentrated in vacuo. The crude residue was purified by column chromatography or reverse phase HPLC to give Product Formula (I).

Example 1

2-Allyl-1-(6-(2-hydroxypropan-2-yl)pyridin-2-yl)-6-((2'-methyl-2',3'-dihydro-1'H-spiro-[cyclopropane-1,4'-isoquinolin]-7'-yl)amino)-1,2-dihydro-3H-pyrazolo[3,4-d]pyrimidin-3-one

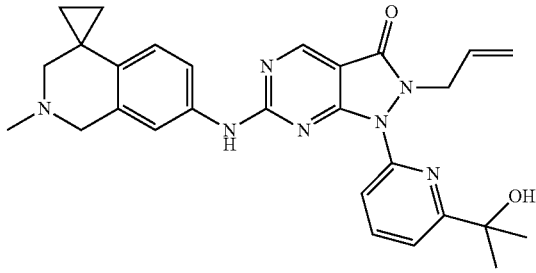 [SMILES: C=CCn1c(=O)c2cnc(Nc3ccc4c(c3)CN(C)CC43CC3)nc2n1-c1cccc(C(C)(C)O)n1]

2-(2-Iodophenyl)acetic acid (100 g, 381.67 mmol) was dissolved in MeOH (400 mL). SOCl$_2$ (34 mL, 458.01 mmol) was added at RT with stirring, and the reaction mixture was heated at 60° C. for 1 h. The solvent was removed in vacuo. The resulting crude material was dissolved in ethyl acetate (250 mL), washed with saturated NaHCO$_3$ (1×100 mL), brine (1×100 mL) and dried (Na$_2$SO$_4$). The solvent was removed to afford methyl 2-(2-iodophenyl)acetate (100 g, 95%) as a brown oil. MS (ESI) m/z 276.9 [M+H]$^+$.

To a solution of methyl 2-iodobenzoate (100 g, 362.31 mmol) in DMF (350 mL) was added copper (I) cyanide (35.6 g, 398.55 mmol). The resulting mixture was stirred at 130° C. for 5 h. The reaction was diluted with 5% aq. NH$_4$OH solution (350 mL). After stirring for 30 min, the mixture was extracted with CH$_2$Cl$_2$ (3×200 mL). The organic extracts were dried (Na$_2$SO$_4$) and concentrated under reduced pressure. The resulting crude mixture was purified by flash chromatography (SiO$_2$, 7% EA/pet. ether) to afford methyl 2-(2-cyanophenyl)acetate (56 g, 86%) as a brown oil. MS (ESI) m/z 176.0 [M+H]$^+$.

Sodium hydride (14.5 g, 604.20 mmol) was suspended in dry DMF (500 mL). The mixture was cooled to 0° C. under N$_2$. To this solution, methyl 2-(2-cyanophenyl)acetate (53 g, 302.87 mmol) in DMF (50 mL) was added at 0° C. and stirred at RT for 20 mins. 1,2-dibromoethane (52.4 mL, 605.7 mmol) was then added to the reaction mixture at 0° C. The reaction was stirred at 0° C. for 30 mins and at RT for 1 h. After completion of the reaction, cold water (300 mL) was added, and the mixture was extracted with ethyl acetate (3×750 mL). The combined organic layers were washed with brine (300 mL) and concentrated. The resulting crude mixture was purified by flash chromatography (SiO$_2$, 5% EA/pet. ether) to afford methyl 1-(2-cyanophenyl)cyclopropane-1-carboxylate (40 g, 65%) as a yellow oil. MS (ESI) m/z 202.1 [M+H]$^+$.

Methyl 1-(2-cyanophenyl)cyclopropanecarboxylate (38 g, 56.18 mmol), MeOH (500 mL) and Raney-Ni (19 g) were added to a steel bomb. The mixture was stirred at RT under 50 PSI hydrogen for 15 h. After completion of the reaction, the reaction mixture was filtered through a celite pad and washed with 30% MeOH:DCM. The solvent was removed, and the resulting crude product was purified by flash chromatography (SiO$_2$, 30% EA/pet. ether) to afford 1',2'-dihydro-3'H-spiro[cyclopropane-1,4'-isoquinolin]-3'-one (25 g, 78%) as an off white solid. MS (ESI) m/z 174.0 [M+H]$^+$.

Potassium nitrate (15.4 g, 152.48 mmol) was added over 5 mins to a sulfuric acid solution (650 mL) of 1',2'-dihydro-3'H-spiro[cyclopropane-1,4'-isoquinolin]-3'-one (25 g, 144.51 mmol). The reaction was stirred for 10 mins and then poured into cold water. The precipitate was removed via filtration and washed with water to obtain 7'-nitro-1'H-spiro [cyclopropane-1,4'-isoquinolin]-3'(2'H)-one (20 g, 63%) as a yellow solid. MS (ESI) m/z 219.0 [M+H]$^+$.

BF$_3$.OEt$_2$ (47.3 mL, 366.4 mmol) was added to a 0° C. suspension of NaBH$_4$ (10.4 g, 275.3 mmol) in THF (40 mL) and then stirred for 1 h. A solution of 7'-nitro-1'H-spiro [cyclopropane-1,4'-isoquinolin]-3'(2'H)-one (20 g, 91.74 mmol) in THF (400 mL) was added to the reaction. The mixture was heated at reflux for 2 h. The reaction was cooled, and neutralized with saturated NaHCO$_3$. The solvent was evaporated under reduced pressure. The residue was dissolved in EtOH and HCl (5N) was added. The mixture heated under reflux for 1 h. The reaction was cooled, then the solvent was evaporated under reduced pressure. The residue was neutralized with sat. NaHCO$_3$, and the aqueous layer was extracted with chloroform. The organic layer was dried (Na$_2$SO$_4$) and concentrated under reduced pressure to afford 7'-nitro-2',3'-dihydro-1$^1$H-spiro[cyclopropane-1,4'-isoquinoline](14.6 g, 78%). MS (ESI) m/z 205.0 [M+H]$^+$.

NaCNBH$_3$ (9.8 g, 157.45 mmol) was added to a solution of 7'-nitro-2',3'-dihydro-1'H-spiro[cyclopropane-1,4'-isoquinoline] (14.6 g, 71.57 mmol) in MeOH (400 mL). Formaldehyde (37% aq., 5.8 mL, 213.10 mmol) and acetic acid (4.0 mL, 71.57 mmol) were added. The reaction was stirred at RT for 4 h. The reaction was neutralized with sat. NaHCO$_3$. The solvent was evaporated under reduced pressure. The residue was diluted with water and extracted with 5% MeOH:DCM (3×200 mL). The combined organic layers were concentrated under reduced pressure. The resulting crude mixture was purified flash chromatography (SiO$_2$, 3% MeOH/DCM) to afford 2'-methyl-7'-nitro-2',3'-dihydro-1'H-spiro[cyclopropane-1,4'-isoquinoline] (11.5 g, 73%) as an off white solid. MS (ESI) m/z 219.2 [M+H]$^+$.

2'-methyl-7'-nitro-2',3'-dihydro-1'H-spiro[cyclopropane-1,4'-isoquinoline](1.5 g, 6.88 mmol) was added to a steel bomb followed by MeOH (50 mL) and Raney-Ni (0.75 g). The reaction mixture was stirred at RT under a H$_2$ atmosphere for 3 h. After completion, the reaction mixture was filtered through a celite pad and washed with 30% MeOH: DCM. The filtrate was concentrated and dried to afford 2'-methyl-2',3'-dihydro-1'H-spiro[cyclopropane-1,4'-isoquinolin]-7'-amine (0.78 g, 63%) as a pale yellow solid. MS (ESI) m/z 189.2 [M+H]$^+$.

Example 1 was prepared according to General Procedure B using 2'-methyl-2',3'-dihydro-1'H-spiro[cyclopropane-1, 4'-isoquinolin]-7'-amine. Melting Point: 115-117° C.; $^1$H NMR (DMSO-d$_6$, 400 MHz) δ 10.17 (br s, 1H), 8.85 (s, 1H), 8.01 (t, J=8.4 Hz, 1H), 7.76 (d, J=8.4 Hz, 1H), 7.63 (d, J=7.6 Hz, 1H), 7.55 (br s, 1H), 7.38-7.33 (m, 1H), 6.66 (d, J=8.8 Hz, 1H), 5.71-5.61 (m, 1H), 5.30 (s, 1H), 5.01-4.96 (m, 1H), 4.86-4.78 (m, 1H), 4.68 (d, J=6.0 Hz, 2H), 3.56 (s, 2H), 2.44 (s, 2H), 2.34 (s, 3H), 1.46 (s, 6H), 0.93-0.79 (m, 4H); MS (ESI) m/z 498.2 [M+H]$^+$.

Example 2

2-Alyl-6-((2',3'-dihydro-1'H-spiro[cyclopropane-1,4'-isoquinolin]-7'-yl)amino)-1-(6-(2-hydroxypropan-2-yl)pyridin-2-yl)-1,2-dihydro-3H-pyrazolo[3,4-d]pyrimidin-3-one hydrochloride

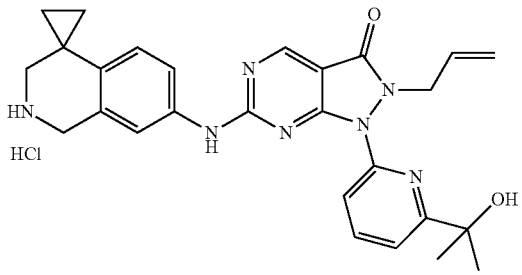 [SMILES: Cl ; C=CCn1c(=O)c2cnc(Nc3ccc4c(c3)CNCC43CC3)nc2n1-c1cccc(C(C)(C)O)n1]

To a stirred solution of 7'-nitro-2',3'-dihydro-1'H-spiro[cyclopropane-1,4'-isoquinoline] (3 g, 14.63 mmol) in 1,4-dioxane: $H_2O$ (45 mL, 2:1) was added 1 N NaOH (15 mL) at 0° C. After 5 mins, di-tert-butyl dicarbonate (3.7 mL, 16.91 mmol) was added at 0° C., and the reaction was stirred at RT for 2 h. The reaction was acidified with $KHSO_4$ (pH: 2-3), then the mixture was extracted with ethyl acetate (2×100 mL). The combined organic layers were washed with water (25 mL), dried ($Na_2SO_4$) and concentrated. The resulting crude mixture was purified by column chromatography ($SiO_2$, 20% EA/pet. ether) to afford tert-butyl 7'-nitro-1'H-spiro[cyclopropane-1,4'-isoquinoline]-2'(3'H)-carboxylate (2.5 g, 56%) as a pale yellow solid. MS (ESI) m/z 249.0 $[M-C_4H_8+H]^+$.

To a stirred solution of tert-butyl 7'-nitro-1'H-spiro[cyclopropane-1,4'-isoquinoline]-2'(3'H)-carboxylate (1.0 g, 3.28 mmol) in EtOH (50 mL) was added stannous chloride (3.74 g, 19.67 mmol) followed by ammonium chloride (1.04 g, 19.672 mmol) at RT. The reaction was stirred at 70° C. for 1 h. After completion of the reaction, the crude reaction was concentrated under reduced pressure, diluted water (20 mL) and the pH was adjusted with saturated $NaHCO_3$ to pH 8-9. The mixture was filtered through a celite pad, washed with 30% MeOH:DCM (3×100 mL) and concentrated to afford tert-butyl 7'-amino-1'H-spiro[cyclopropane-1,4'-isoquinoline]-2'(3'H)-carboxylate (615 mg, 93%) as an off-white solid. MS (ESI) m/z 275.4 $[M+H]^+$.

Tert-butyl 7'-(2-allyl-1-(6-(2-hydroxypropan-2-yl)pyridin-2-yl)-3-oxo-2,3-dihydro-1H-pyrazolo[3,4-d]pyrimidin-6-ylamino)-1'H-spiro[cyclopropane-1,4'-isoquinoline]-2'(3'H)-carboxylate was prepared according to General Procedure B using tert-butyl-7'-amino-1'H-spiro[cyclopropane-1,4'-isoquinoline]-2'(3'H)-carboxylate. MS (ESI) m/z 584.6 $[M+H]^+$.

To a stirred solution of tert-butyl 7'-(2-allyl-1-(6-(2-hydroxypropan-2-yl)pyridin-2-yl)-3-oxo-2,3-dihydro-1H-pyrazolo[3,4-d]pyrimidin-6-ylamino)-1'H-spiro[cyclopropane-1,4'-isoquinoline]-2'(3'H)-carboxylate (110 mg, 0.22 mmol) in 1,4-dioxane (2 mL) was added 4.0 M HCl in 1,4-dioxane (2 mL) at 0° C. The reaction was stirred at RT for 1 h. The reaction was concentrated under reduced pressure and co-distilled with diethyl ether (2×) to afford Example 2 (110 mg, 88%) as an off white solid. Melting Point: 246-248° C.; $^1H$ NMR (DMSO-$d_6$, 400 MHz) δ 10.30 (br s, 1H), 9.29 (br s, 2H), 8.89 (s, 1H), 8.05 (t, J=7.6 Hz, 1H), 7.78 (d, J=8.4 Hz, 1H), 7.75-7.71 (m, 1H), 7.63 (d, J=8.0 Hz, 1H), 7.48 (d, J=8.4 Hz, 1H), 6.83 (d, J=8.8 Hz, 1H), 5.72-5.61 (m, 1H), 4.99 (d, J=10.0 Hz, 1H), 4.84-4.80 (m, 1H), 4.69 (d, J=5.6 Hz, 2H), 4.41-4.34 (m, 2H), 3.28-3.24 (m, 2H), 1.46 (s, 6H), 1.11-1.05 (d, J=5.6 Hz, 4H); MS (ESI) m/z 484.2 $[M+H]^+$.

Example 3

2-Allyl-1-(6-(2-hydroxypropan-2-yl)pyridin-2-yl)-6-((2'-isopropyl-2',3'-dihydro-1'H-spiro[cyclopropane-1,4'-isoquinolin]-7'-yl)amino)-1,2-dihydro-3H-pyrazolo[3,4-d]pyrimidin-3-one

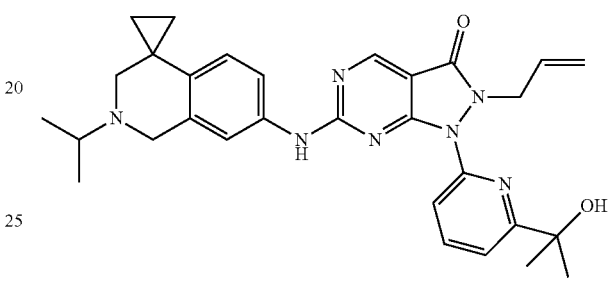

To a stirred solution of 7'-nitro-2',3'-dihydro-1'H-spiro[cyclopropane-1,4'-isoquinoline] (0.7 g, 3.41 mmol) in DMF (6 mL) was added $K_2CO_3$ (1.88 g, 13.66 mmol) followed by 2-iodopropane (0.68 mL, 6.83 mmol). The reaction was stirred at RT for 6 h. Water (50 mL) was added, and the mixture was extracted with EA (2×100 mL). The combined organic layers were washed with brine (50 mL), dried ($Na_2SO_4$) and concentrated in vacuo. The crude reaction was purified by column chromatography ($SiO_2$, 30% EA/pet. ether to afford 2'-isopropyl-7'-nitro-2',3'-dihydro-1'H-spiro[cyclopropane-1,4'-isoquinoline] (0.45 g, 53%) as a pale yellow liquid. MS (ESI) m/z 247.3 $[M+H]^+$.

To a stirred solution of 2'-isopropyl-7'-nitro-2',3'-dihydro-1'H-spiro[cyclopropane-1,4'-isoquinoline] (0.38, 1.54 mmol) in ethanol (12 mL) was added $SnCl_2$ (1.75 g, 9.27 mmol) followed by $NH_4Cl$ (0.48 g, 9.23 mmol) at RT. The reaction was stirred at 70° C. for 1 h. After completion, the crude reaction was concentrated under reduced pressure, diluted water (20 mL) and the pH was adjusted with saturated $NaHCO_3$ to pH 8-9. The mixture was filtered through a celite pad, washed with 30% MeOH:DCM (3×100 mL) and concentrated to afford to afford 2'-isopropyl-2',3'-dihydro-1'H-spiro[cyclopropane-1,4'-isoquinolin]-7'-amine (0.18 g, 54%) as a yellow solid. MS (ESI) m/z 217.2 $[M+H]^+$.

Example 3 was prepared according to General Procedure B using 2'-isopropyl-2',3'-dihydro-1'H-spiro[cyclopropane-1,4'-isoquinolin]-7'-amine. Melting Point: 118-120° C.; $^1H$ NMR (DMSO-$d_6$, 400 MHz) δ 10.17 (br s, 1H), 8.85 (s, 1H), 7.99 (t, J=8.0 Hz, 1H), 7.77 (d, J=7.6 Hz, 1H), 7.63 (d, J=7.2 Hz, 1H), 7.60-7.54 (m, 1H), 7.32 (d, J=6.8 Hz, 1H), 6.65 (d, J=8.8 Hz, 1H), 5.72-5.59 (m, 1H), 5.30 (s, 1H), 4.98 (d, J=10.0 Hz, 1H), 4.82 (d, J=18.8 Hz, 1H), 4.68 (d, J=6.0 Hz, 2H), 3.70 (s, 2H), 2.86-2.80 (m, 1H), 2.51 (s, 2H), 1.46 (s, 6H), 1.06 (d, J=6.4 Hz, 6H), 1.00-0.78 (m, 4H); MS (ESI) m/z 526.3 $[M+H]^+$.

Example 4

6-((2'-Acetyl-2',3'-dihydro-1'H-spiro[cyclopropane-1,4'-isoquinolin]-7'-yl)amino)-2-allyl-1-(6-(2-hydroxypropan-2-yl)pyridin-2-yl)-1,2-dihydro-3H-pyrazolo[3,4-d]pyrimidin-3-one

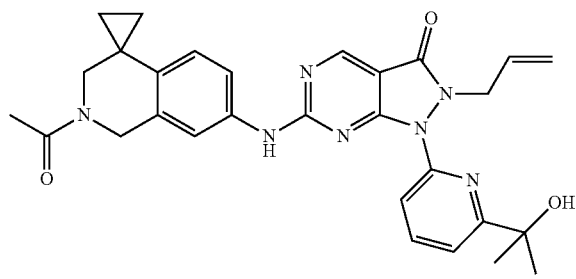 [SMILES: C=CCn1c(=O)c2cnc(Nc3ccc4c(c3)CN(C(C)=O)CC43CC3)nc2n1-c1cccc(C(C)(C)O)n1]

To a stirred solution of 7'-nitro-2',3'-dihydro-1'H-spiro[cyclopropane-1,4'-isoquinoline] (500 mg, 2.45 mmol) in THF (10 mL) was added Et$_3$N (0.825 mL, 6.13 mmol) at 0° C. After 5 mins, acetyl chloride (0.19 mL, 2.69 mmol) was added at 0° C. The reaction was stirred at RT for 2 h. The reaction mixture was diluted with water and extracted with EA (2×30 mL). The combined organic layers were washed with water (15 mL) dried (Na$_2$SO$_4$) and concentrated. The residue was triturated with pentane to afford 1-(7'-nitro-1'H-spiro[cyclopropane-1,4'-isoquinoline]-2'(3'H)-yl)ethanone (386 mg, 63%) as a pale yellow solid. MS (ESI) m/z 247.3 [M+H]$^+$.

To a stirred solution of 1-(7'-nitro-1'H-spiro[cyclopropane-1,4'-isoquinoline]-2'(3'H)-yl)ethanone (380 mg, 1.54 mmol) in EtOH (20 mL) was added SnCl$_2$ (1.76 g, 9.27 mmol) followed by NH$_4$Cl (0.49 g, 9.27 mmol) at RT. The reaction was stirred at 70° C. for 1 h. After completion, the crude reaction was concentrated under reduced pressure, diluted with water (20 mL) and the pH was adjusted with saturated NaHCO$_3$ to pH 8-9. The reaction was filtered through a celite pad, washed with 30% MeOH:DCM (3×100 mL) and concentrated to afford 1-(7'-amino-1'H-spiro[cyclopropane-1,4'-isoquinoline]-2'(3'H)-yl)ethanone (305 mg, 91%) as a light yellow liquid. MS (ESI) m/z 217.3 [M+H]$^+$.

Example 4 was prepared according to General Procedure B using 1-(7'-amino-1'H-spiro[cyclopropane-1,4'-isoquinoline]-2'(3'H)-yl)ethanone. Melting Point: 181-183° C.; $^1$H NMR (DMSO-d$_6$, 400 MHz, VT NMR at 80° C.) δ 10.27 (br s, 1H), 8.87 (s, 1H), 8.12-8.01 (m, 1H), 7.76 (d, J=10 Hz, 1H), 7.71-7.66 (m, 1H), 7.62 (d, J=10 Hz, 1H), 7.40-7.37 (m, 1H), 6.77 (d, J=11.2 Hz, 1H), 5.72-5.62 (m, 1H), 5.04-4.83 (m, 3H), 4.70-4.66 (m, 4H), 3.52 (s, 2H), 2.07 (s, 3H), 1.47 (s, 6H), 0.99-0.90 (m, 4H); MS (ESI) m/z 526.3 [M+H]$^+$.

Example 5

2-Allyl-1-(6-(2-hydroxypropan-2-yl)pyridin-2-yl)-6-((2-methyl-1,2,3,4-tetrahydroisoquinolin-7-yl)amino)-1,2-dihydro-3H-pyrazolo[3,4-d]pyrimidin-3-one

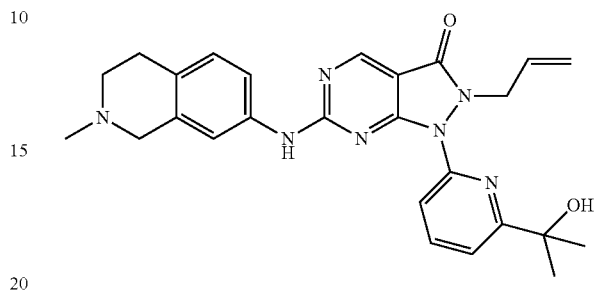

To concentrated H$_2$SO$_4$ solution (62 mL) at 4° C. was added 1,2,3,4-tetrahydroisoquinoline (15 g, 112.78 mmol) dropwise keeping the temperature below 15° C. To the stirring mixture at 4° C. was added NaNO$_3$ (12.5, 148.80 mmol) keeping internal temperature below 10° C. The reaction mixture was stirred at RT for 16 h. The reaction mixture was added to NH$_4$OH (185 mL) to a final pH=8. The mixture was extracted with DCM (3×150 mL), washed with brine (75 mL) and dried (Na$_2$SO$_4$). The solvent was removed. The resulting crude was dissolved in EtOH (50 mL) and concentrated HCl (14 mL) was added. The resulting solid was filtered and washed with diethyl ether to afford 7-nitro-1,2,3,4-tetrahydroisoquinoline (13 g, 86%) as a mixture of isomers. MS (ESI) m/z: 179.1 [M+H]$^+$.

To a stirred solution of 7-nitro-1,2,3,4-tetrahydroisoquinoline (10 g, 56.18 mmol) in dry 1,2-dichloroethane (200 mL) was added formalin (2.3 mL, 61.80 mmol, 37% aq. formaldehyde) followed by NaCNBH$_3$ (52 g, 245.35 mmol). The reaction was stirred vigorously at RT for 24 h. The solvent was removed in vacuo, and the mixture was diluted with EA (200 mL). Sat. NaHCO$_3$ (200 mL) was added with vigorous stirring. The layers were separated, and the water layer was extracted with ethyl acetate (2×100 mL). The combined organic layers were dried (Na$_2$SO$_4$) and concentrated in vacuo to give a brown oil. The crude product was purified by chromatography (SiO$_2$, MeOH/DCM) to afford mixture of 3-regio isomers (5 g, 26.041 mmol). The mixture of regioisomers (4 g) was purified by SFC-Prep (Lux Amylose-2, (4.6×250 mm), 90% CO$_2$:10% 0.5% DEA in ethanol) to afford 2-methyl-7-nitro-1,2,3,4-tetrahydroisoquinoline (1.5 g). MS (ESI) m/z 193.0 [M+H]$^+$.

To a stirred solution of 2-methyl-7-nitro-1,2,3,4-tetrahydroisoquinoline (700 mg, 3.64 mmol) in EtOH (75 mL) was added 10% Pd/C (350 mg). The reaction was stirred under a H$_2$ atmosphere at RT for 3 h. After completion, the crude reaction was filtered through a celite pad and washed with 30% MeOH:DCM (3×10 mL). The solvent was removed to afford 2-methyl-1,2,3,4-tetrahydroisoquinolin-7-amine (560 mg, 94%) as a pale yellow solid. MS (ESI) m/z 163.2 [M+H]$^+$.

Example 5 was prepared according to General Procedure B using 2-methyl-1,2,3,4-tetrahydroisoquinolin-7-amine. Melting Point: 213-215° C.; $^1$H NMR (DMSO-d$_6$, 400 MHz) δ 10.18 (br s, 1H), 8.86 (s, 1H), 8.00 (t, J=8.0 Hz, 1H), 7.76 (d, J=7.6 Hz, 1H), 7.63 (d, J=7.6 Hz, 1H), 7.56 (br s, 1H), 7.42-7.37 (m, 1H), 7.05 (d, J=8.8 Hz, 1H), 5.69-5.61

(m, 1H), 5.30 (s, 1H), 4.98 (d, J=10.4 Hz, 1H), 4.86-4.78 (m, 1H), 4.68 (d, J=6.0 Hz, 2H), 3.48 (s, 2H), 2.77 (t, J=5.6 Hz, 2H), 2.64-2.57 (m, 2H), 2.37 (s, 3H), 1.46 (s, 6H); MS (ESI) m/z 472.5 [M+H]$^+$.

Example 6

2-Allyl-1-(6-(2-hydroxypropan-2-yl)pyridin-2-yl)-6-((1,2,3,4-tetrahydroisoquinolin-7-yl)amino)-1,2-dihydro-3H-pyrazolo[3,4-d]pyrimidin-3-one hydrochloride

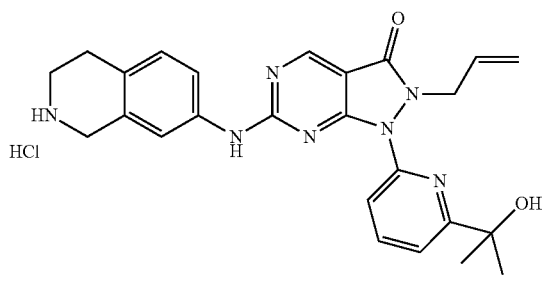 [SMILES: Cl ; C=CCn1c(=O)c2cnc(Nc3ccc4c(c3)CNCC4)nc2n1-c1cccc(C(C)(C)O)n1]

To a stirred solution of 7-nitro-1,2,3,4-tetrahydroisoquinoline (4 g, 22.41 mmol) in 1,4-dioxane: H$_2$O (2:1, 60 mL) was added 1 N NaOH (20 mL) at 0° C. After 5 min, di-tert-butyl dicarbonate (5.66 mL, 24.68 mmol) was added at 0° C., and the reaction was stirred at RT for 2 h. The reaction was acidified with KHSO$_4$ (pH: 2-3), then the mixture was extracted with EA (2×100 mL). The combined organic layers were washed with water (25 mL), dried (Na$_2$SO$_4$) and concentrated. The resulting crude was purified by column chromatography (SiO$_2$, 20% EA/pet. ether) to afford tert-butyl 7-nitro-3,4-dihydroisoquinoline-2(1H)-carboxylate (4.8 g, 77%) as a pale yellow solid. MS (ESI) m/z 223.2 [M-C$_4$H$_8$+H]$^+$.

To a stirred solution of tert-butyl 7-nitro-3,4-dihydroisoquinoline-2(1H)-carboxylate (3.5 g, 12.59 mmol) in EtOH (50 mL) was added wet 10% Pd/C (3 g), and the reaction was stirred under a H$_2$ atmosphere at RT for 3 h. After completion of the reaction, the crude reaction was filtered through a celite pad, washed with 30% MeOH:DCM (3×100 mL) and concentrated to afford tert-butyl 7-amino-3,4-dihydroisoquinoline-2(1H)-carboxylate (2.6 g, 83%) as a light yellow liquid. MS (ESI) m/z 193.2 [M-C$_4$H$_8$+H]$^+$.

Tert-butyl 7-(2-allyl-1-(6-(2-hydroxypropan-2-yl)pyridin-2-yl)-3-oxo-2,3-dihydro-1H-pyrazolo[3,4-d]pyrimidin-6-ylamino)-3,4-dihydroisoquinoline-2(1H)-carboxylate was prepared according to General Procedure B using tert-butyl 7-amino-3,4-dihydroisoquinoline-2(1H)-carboxylate. MS (ESI) m/z 558.3 [M+H]$^+$.

To a stirred solution of tert-butyl 7-(2-allyl-1-(6-(2-hydroxypropan-2-yl)pyridin-2-yl)-3-oxo-2,3-dihydro-1H-pyrazolo[3,4-d]pyrimidin-6-ylamino)-3,4-dihydroiso-quinoline-2(1H)-carboxylate (130 mg, 0.23 mmol) in 1,4-dioxane (2 mL) was added 4.0 M HCl in 1,4-dioxane (2 mL) at 0° C. The mixture was stirred at RT for 1 h. The mixture was concentrated under reduced pressure and co-distilled with diethyl ether (2×) to afford Example 6 (92 mg, 83%) as an off white solid. Melting Point: 234-236° C.; $^1$H NMR (DMSO-d$_6$, 400 MHz) δ 10.24 (br s, 1H), 9.07 (br s, 2H), 8.89 (s, 1H), 8.04 (t, J=8.0 Hz, 1H), 7.79 (d, J=7.6 Hz, 1H), 7.75-7.71 (m, 1H), 7.63 (d, J=8.0 Hz, 1H), 7.53-7.47 (m, 1H), 7.19 (d, J=8.8 Hz, 1H), 5.74-5.61 (m, 1H), 4.99 (d, J=9.2 Hz, 1H), 4.86-4.78 (m, 1H), 4.69 (d, J=5.6 Hz, 2H), 4.30-4.25 (m, 2H), 3.39 (t, J=6.4 Hz, 2H), 2.96 (t, J=6.0 Hz, 2H), 1.16 (s, 6H); MS (ESI) m/z 458.5 [M+H]$^+$.

Example 7

2-Allyl-6-((2-ethyl-1,2,3,4-tetrahydroisoquinolin-7-yl)amino)-1-(6-(2-hydroxypropan-2-yl)pyridin-2-yl)-1,2-dihydro-3H-pyrazolo[3,4-d]pyrimidin-3-one

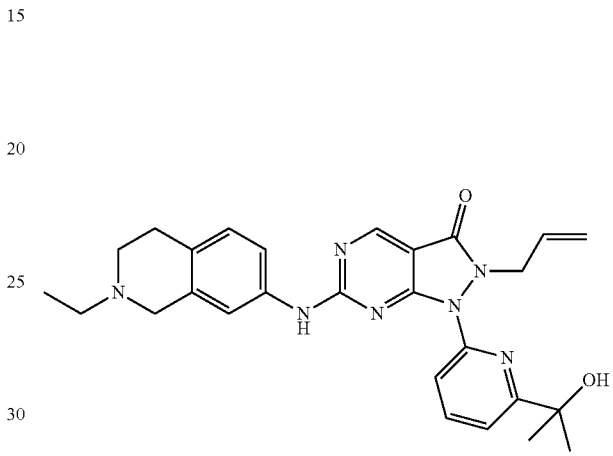

To a stirred solution of 7-nitro-1,2,3,4-tetrahydroisoquinoline (5 g, 28.09 mmol) in DMF (20 mL) was added K$_2$CO$_3$ (15.5 g, 112.36 mmol) followed by ethyl iodide (4.4 mL, 56.18 mmol). The reaction was stirred at RT for 3 h. Water (50 mL) was added, and the mixture was extracted with ethyl acetate (2×100 mL). The combined organic layers were washed with brine (25 mL), dried (Na$_2$SO$_4$) and concentrated in vacuo. The resulting crude residue was purified by column chromatography (SiO$_2$, 30% EA/pet. ether) to afford 2-ethyl-7-nitro-1,2,3,4-tetrahydroisoquinoline (3.1 g, 54%) as a pale yellow liquid. MS (ESI) m/z 207.1 [M+H]$^+$.

To a stirred solution of 2-ethyl-7-nitro-1,2,3,4-tetrahydroisoquinoline (3.1 g, 15.05 mmol) in EtOH (50 mL) was added wet 10% Pd/C (3 g), and the reaction was stirred at RT under a H$_2$ atmosphere for 3 h. After completion, the reaction was filtered through a celite pad and washed with 30% MeOH:DCM (3×100 mL) and concentrated to afford 2-ethyl-1,2,3,4-tetrahydroisoquinolin-7-amine (2.1 g, 79%) as a yellow liquid. MS (ESI) m/z 177.0 [M+H]$^+$.

Example 7 was prepared according to General Procedure B using 2-ethyl-1,2,3,4-tetrahydroisoquinolin-7-amine. $^1$H NMR (DMSO-d$_6$, 400 MHz) δ 10.26 (br s, 1H), 8.86 (s, 1H), 7.98 (t, J=7.6 Hz, 1H), 7.76 (d, J=8.4 Hz, 1H), 7.63 (d, J=8.0 Hz, 1H), 7.61-7.56 (m, 1H), 7.37 (d, J=8.4 Hz, 1H), 7.04 (d, J=8.4 Hz, 1H), 5.72-5.59 (m, 1H), 5.32 (br s, 1H), 4.98 (d, J=10.4 Hz, 1H), 4.82 (d, J=18.4 Hz, 1H), 4.68 (d, J=6.0 Hz, 2H), 3.50 (s, 2H), 2.75 (t, J=5.2 Hz, 2H), 2.64 (t, J=5.6 Hz, 2H), 2.57-2.53 (m, 2H), 1.46 (s, 6H), 1.12 (t, J=6.8 Hz, 3H); MS (ESI) m/z 486.5 [M+H]$^+$.

Example 8

6-((2-Acetyl-1,2,3,4-tetrahydroisoquinolin-7-yl)amino)-2-allyl-1-(6-(2-hydroxypropan-2-yl)pyridin-2-yl)-1,2-dihydro-3H-pyrazolo[3,4-d]pyrimidin-3-one

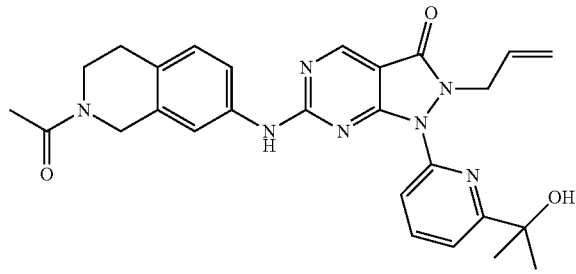 [SMILES: C=CCn1c(=O)c2cnc(Nc3ccc4c(c3)CN(C(C)=O)CC4)nc2n1-c1cccc(C(C)(C)O)n1]

To a stirred solution of 7-nitro-1,2,3,4-tetrahydroisoquinoline (1 g, 5.62 mmol) in THF (15 mL) was added Et₃N (1.6 mL, 14.04) at 0° C. After 5 min, acetyl chloride (0.35 mL, 5.62 mmol) was added at 0° C., and the reaction was stirred at RT for 2 h. The reaction was diluted with water (15 mL) and extracted with EA (2×50 mL). The combined organic layers were washed with water (15 mL), brine (25 mL), dried (Na₂SO₄) and concentrated in vacuo. The crude mixture was triturated with pentane to afford 1-(7-nitro-3,4-dihydroisoquinolin-2(1H)-yl)ethanone (600 mg, 50%) as a pale yellow solid. MS (ESI) m/z 221.2 [M+H]⁺.

To a stirred solution of 1-(7-nitro-3,4-dihydroisoquinolin-2(1H)-yl)ethanone (600 mg, 2.72 mmol) in EtOH (30 mL) was added wet 10% Pd/C (600 mg), and the reaction was stirred under a H₂ atmosphere for 3 h. After completion, the crude reaction was filtered through a celite pad, washed with 30% MeOH:DCM (3×30 mL) and concentrated to afford 1-(7-amino-3,4-dihydroisoquinolin-2(1H)-yl)ethanone (320 mg, 62%) as a light yellow liquid. MS (ESI) m/z 191.3 [M+H]⁺.

Example 8 was prepared according to General Procedure B using 1-(7-amino-3,4-dihydroisoquinolin-2(1H)-yl)ethanone. Melting Point: 222-224° C.; ¹H NMR (DMSO-d₆, 400 MHz) δ 10.26 (br s, 1H), 8.87 (s, 1H), 8.14-8.02 (m, 1H), 7.82-7.73 (m, 2H), 7.63-7.60 (m, 1H), 7.45-7.34 (m, 1H), 7.12 (d, J=8.0 Hz, 1H), 5.73-5.61 (m, 1H), 5.30 (s, 1H), 4.99 (t, J=10.4 Hz, 1H), 4.82 (d, J=17.2 Hz, 1H), 4.72-4.67 (m, 2H), 4.61 (d, J=8.8 Hz, 2H), 3.66 (t, J=5.6 Hz, 2H), 2.82 (t, J=6.0 Hz, 1H), 2.70 (t, J=6.0 Hz, 1 Hz), 2.10 (s 3H), 1.46 (s, 6H); MS (ESI) m/z 500.5 [M+H]⁺.

Example 9

2-Allyl-1-(6-(2-hydroxypropan-2-yl)pyridin-2-yl)-6-((2-(methylsulfonyl)-1,2,3,4-tetrahydroisoquinolin-7-yl)amino)-1,2-dihydro-3H-pyrazolo[3,4-d]pyrimidin-3-one

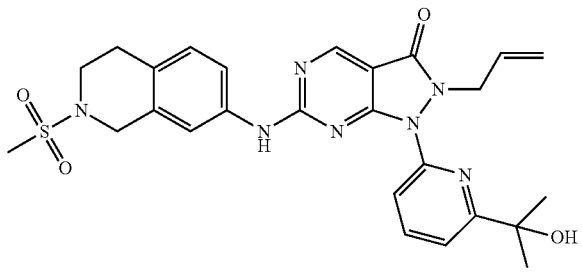 [SMILES: C=CCn1c(=O)c2cnc(Nc3ccc4c(c3)CN(S(C)(=O)=O)CC4)nc2n1-c1cccc(C(C)(C)O)n1]

To a stirred solution of 7'-nitro-2',3'-dihydro-1'H-spiro[cyclopropane-1,4'-isoquinoline] (500 mg, 2.45 mmol) in DMF (5 mL) was added K₂CO₃ (1.55 g, 11.23 mmol) at 0° C. After 5 mins, methanesulfonyl chloride (0.4 mL, 5.62 mmol) was added at 0° C., and the reaction was stirred at RT for 3 h. The reaction was diluted with water and extracted with EA (2×30 mL). The combined organic layers were washed with water (15 mL), dried (Na₂SO₄), and concentrated. The crude was triturated with pentane to afford 2-(methylsulfonyl)-7-nitro-1,2,3,4-tetrahydroisoquinoline (505 mg, 70%) as a pale yellow solid. MS (ESI) m/z 257.3 [M+H]⁺.

To a stirred solution of 2-(methylsulfonyl)-7-nitro-1,2,3,4-tetrahydroisoquinoline (500 mg, 1.95 mmol) in EtOH (20 mL) was added stannous chloride (2.26 g, 11.72 mmol) followed by NH₄Cl (0.621 g, 11.72 mmol) at RT. The reaction was stirred at 70° C. for 1 h. After completion, the reaction was concentrated under reduced pressure, diluted with water, basified with sat. aq. NaHCO₃ (pH 8-9), filtered through a celite pad and washed with 30% MeOH:DCM (3×100 mL). The filtrate was concentrated to afford 2-(methylsulfonyl)-1,2,3,4-tetrahydroisoquinolin-7-amine (356 mg, 80%) as an off white solid. MS (ESI) m/z 227.2 [M+H]⁺.

Example 9 was prepared according to General Procedure B using 2-(methylsulfonyl)-1,2,3,4-tetrahydroisoquinolin-7-amine. ¹H NMR (DMSO-d₆, 400 MHz) δ 10.28 (br s, 1H), 8.89 (s, 1H), 8.03 (t, J=7.6 Hz, 1H), 7.79 (d, J=8.4 Hz, 2H), 7.62 (d, J=7.2 Hz, 1H), 7.42 (d, J=8.4 Hz, 1H), 7.14 (d, J=8.4 Hz, 1H), 5.72-5.61 (m, 1H), 5.35 (s, 1H), 4.99 (d, J=10.4 Hz, 1H), 4.80 (d, J=17.2 Hz, 1H), 4.69 (d, J=5.2 Hz, 2H), 4.36 (s, 2H), 3.44 (t, J=6.0 Hz, 2H), 2.98 (s, 3H), 2.87 (t, J=6.0 Hz, 2H), 1.46 (s, 6H); MS (ESI) m/z 536.2 [M+H]⁺.

Example 10

2-Allyl-1-(6-(2-hydroxypropan-2-yl)pyridin-2-yl)-6-((2-isopropyl-1,2,3,4-tetrahydroisoquinolin-7-yl)amino)-1,2-dihydro-3H-pyrazolo[3,4-d]pyrimidin-3-one

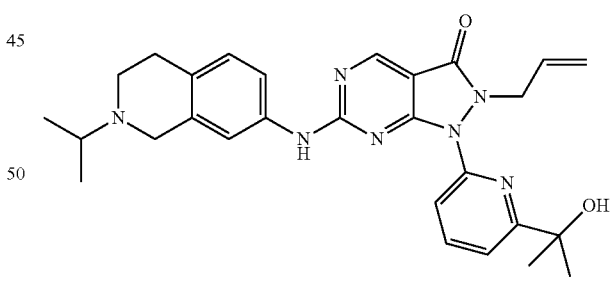

To a stirred solution of 7-nitro-1,2,3,4-tetrahydroisoquinoline (4 g, 22.47 mmol) in DMF (20 mL) was added K₂CO₃ (12.42 g, 89.88 mmol) followed by 2-iodopropane (11.23 mL, 112.35 mmol). The reaction was stirred at RT for 6 h. Water (50 mL) was added to the reaction, and the reaction was extracted with EA (2×100 mL). The combined organic layers were washed with brine (25 mL), dried (Na₂SO₄) and concentrated. The crude mixture was purified by column chromatography (SiO₂, 30% EA/pet. ether) to afford 2-isopropyl-7-nitro-1,2,3,4-tetrahydroisoquinoline (3.2 g, 65%) as a pale yellow liquid. MS (ESI) m/z 221.0 [M+H]⁺.

To a stirred solution of 2-isopropyl-7-nitro-1,2,3,4-tetrahydroisoquinoline (0.4 g, 1.81 mmol) in EtOH (50 mL) was added wet 10% Pd/C (0.3 g), and the reaction was stirred under a $H_2$ atmosphere for 3 h. After completion of the reaction, the crude reaction was filtered through a celite pad, washed with 30% MeOH:DCM (3×100 mL) and concentrated to afford 2-isopropyl-1,2,3,4-tetrahydroisoquinolin-7-amine (0.280 g, 81%) as a brown oil. MS (ESI) m/z 191.2 $[M+H]^+$.

Example 10 was prepared according to General Procedure B using 2-isopropyl-1,2,3,4-tetrahydroisoquinolin-7-amine. Melting Point: 159-161° C.; $^1$H NMR (DMSO-$d_6$, 400 MHz) δ 10.18 (br s, 1H), 8.87 (s, 1H), 7.97 (t, J=7.6 Hz, 1H), 7.77 (d, J=8.0 Hz, 1H), 7.63 (d, J=7.2 Hz, 1H), 7.61-7.56 (m, 1H), 7.35 (dd, J=8.0, 1.6 Hz, 1H), 7.02 (d, J=8.4 Hz, 1H), 5.72-5.59 (m, 1H), 5.31 (br s, 1H), 4.98 (d, J=10.4 Hz, 1H), 4.82 (d, J=18.8 Hz, 1H), 4.68 (d, J=6.0 Hz, 2H), 3.60 (s, 2H), 2.87 (sep, J=6.4 Hz, 1H), 2.76-2.64 (m, 4H), 1.46 (s, 6H), 1.08 (d, J=6.4 Hz, 6H); MS (ESI) m/z 500.5 $[M+H]^+$.

Example 11

2-Allyl-6-((4,4-dimethyl-1,2,3,4-tetrahydroisoquinolin-7-yl)amino)-1-(6-(2-hydroxypropan-2-yl)pyridin-2-yl)-1,2-dihydro-3H-pyrazolo[3,4-d]pyrimidin-3-one hydrochloride

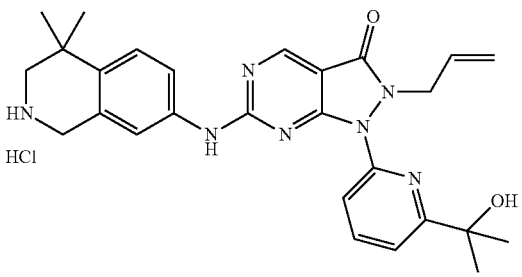 [SMILES: Cl ; C=CCn1c(=O)c2cnc(Nc3ccc4c(c3)CNCC4(C)C)nc2n1-c1cccc(C(C)(C)O)n1]

4,4-Dimethyl-7-nitro-1,2,3,4-tetrahydroisoquinoline was synthesized according to U.S. Pat. No. 7,507,748, which is hereby incorporated by reference for the limited purpose of the synthesis of 4,4-Dimethyl-7-nitro-1,2,3,4-tetrahydroisoquinoline.

To a stirred solution of 4,4-dimethyl-7-nitro-1,2,3,4-tetrahydroisoquinoline (750 mg, 3.66 mmol) in 1,4-dioxane:$H_2O$ (2:1, 12 mL) was added 1N NaOH solution (4 mL) at 0° C. The reaction was stirred for 5 mins and Boc$_2$O (0.92 mL, 4.02 mmol) was added. The ice bath was removed, and the reaction was stirred at RT for 2 h. The reaction was acidified with KHSO$_4$ (pH: 2-3) and extracted with EA (2×50 mL). The combined organic layers were washed with water (25 mL), dried (Na$_2$SO$_4$), filtered and concentrated in vacuo. The crude mixture was purified by column chromatography (SiO$_2$, 20% EA/pet. ether) to afford tert-butyl-4,4-dimethyl-7-nitro-3,4-dihydroisoquinoline-2(1H)-carboxylate (700 mg, 63%) as a pale-yellow liquid. MS (ESI) m/z 307.2 $[M+H]^+$.

To a stirred solution of tert-butyl-4,4-dimethyl-7-nitro-3,4-dihydroisoquinoline-2(1H)-carboxylate (0.7 g, 2.29 mmol) in ethanol (50 mL) was added SnCl$_2$ (2.6 g, 13.72 mmol) followed by NH$_4$Cl (0.72 g, 13.72 mmol) at RT. The reaction was heated at 70° C. for 1 h. After completion of the reaction by TLC, the reaction was concentrated in vacuo. The residue was dissolved in water, basified with sat. NaHCO$_3$ (pH: 8-9), and filtered through celite. The filtrate was extracted with 30% MeOH:DCM (3×100 mL). The combined organic layers were dried (Na$_2$SO$_4$), filtered and concentrated in vacuo to afford tert-butyl-7-amino-4,4-dimethyl-3,4-dihydroisoquinoline-2(1H)-carboxylate (500 mg, 79%) as an off-white solid. MS (ESI) m/z 277.5 $[M+H]^+$.

Tert-butyl 7-((2-allyl-1-(6-(2-hydroxypropan-2-yl)pyridin-2-yl)-3-oxo-2,3-dihydro-1H-pyrazolo[3,4-d]pyrimidin-6-yl)amino)-4,4-dimethyl-3,4-dihydroisoquinoline-2(1H)-carboxylate, was prepared according to General Procedure A using tert-butyl-7-amino-4,4-dimethyl-3,4-dihydroisoquinoline-2(1H)-carboxylate. The crude residue was purified by reverse phase HPLC (water/CH$_3$CN, 0.1% formic acid) to afford (170 mg, 22%) of the title as an off-white solid; MS (ESI) m/z 586.4 $[M+H]^+$.

To a solution of tert-butyl 7-(2-allyl-1-(6-(2-hydroxypropan-2-yl)pyridin-2-yl)-3-oxo-2,3-dihydro-1H-pyrazolo[3,4-d]pyrimidin-6-yl-amino)-4,4-dimethyl-3,4-dihydroisoquinoline-2(1H)-carboxylate (170 mg, 0.290 mmol) in 1,4-dioxane (5 mL) was added 4 N HCl in 1,4-dioxane (10 mL) at 0° C. The ice bath was removed, and the reaction was stirred at RT for 2 h. The reaction was concentrated under reduced pressure, and the residue was co-distilled with diethyl ether to afford Example 11 (160 mg) as an off-white solid. $^1$H NMR (DMSO-$d_6$, 400 MHz) δ 10.32 (br s, 1H), 9.12 (br s, 2H), 8.89 (s, 1H), 8.05 (t, J=8.0 Hz, 1H), 7.79 (d, J=8.0 Hz, 1H), 7.69 (br s, 1H), 7.63 (d, J=8.0 Hz, 1H), 7.54 (d, J=10.8 Hz, 1H), 7.44 (d, J=8.4 Hz, 1H), 5.70-5.63 (m, 1H), 5.0 (d, J=4.8 Hz, 1H) 4.69 (d, J=6.4 Hz, 1H), 4.25 (s, 2H), 3.23 (s, 2H), 1.46 (s, 6H), 1.34 (m, 6H); MS (LCMS) m/z 486.3 $[M+H]^+$.

Example 12

2-Allyl-1-(6-(2-hydroxypropan-2-yl)pyridin-2-yl)-6-((2,4,4-trimethyl-1,2,3,4-tetrahydroisoquinolin-7-yl)amino)-1,2-dihydro-3H-pyrazolo[3,4-d]pyrimidin-3-one

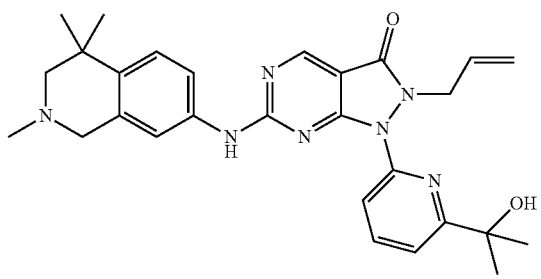 [SMILES: C=CCn1c(=O)c2cnc(Nc3ccc4c(c3)CN(C)CC4(C)C)nc2n1-c1cccc(C(C)(C)O)n1]

To a stirred solution of 4,4-dimethyl-7-nitro-1,2,3,4-tetrahydroisoquinoline (1.0 g, 4.85 mmol) was dissolved in DCE (20 mL), formaldehyde (37% aq. solution) (0.8 mL, 7.28 mmol) was added followed by NaCNBH$_3$ (4.46 g, 21.36 mmol) at 0° C. The ice bath was removed, and the reaction was stirred at RT for 16 h. The reaction was quenched with 1N NaOH, diluted with water (50 mL) and extracted with EA (2×50 mL). The combined organic layers were washed with cold water, brine (100 mL), dried (Na$_2$SO$_4$), filtered and concentrated in vacuo. The crude residue was purified by column chromatography (SiO$_2$, 15% EA/pet. ether) to afford 2,4,4-trimethyl-7-nitro-1,2,3,4-tetrahydroisoquinoline (900 mg, 84%) as a yellow solid; MS (ESI) m/z 221.1 $[M+H]^+$.

To a stirred solution of 2,4,4-trimethyl-7-nitro-1,2,3,4-tetrahydroisoquinoline (500 mg, 2.26 mmol) in EtOH (30 mL) was added SnCl₂ (2.58 g, 13.57 mmol) and NH₄Cl (0.72 g, 13.57 mmol) at RT. The reaction was heated at 70° C. for 1 h. After completion of the reaction by TLC, the reaction was concentrated in vacuo, diluted with water and basified with sat. NaHCO₃ (pH: 8-9). The mixture was filtered through a celite pad, and the filtrate was extracted with 30% MeOH:DCM (3×100 mL). The combined organic layers were dried (Na₂SO₄), filtered and concentrated in vacuo to afford 2,4,4-trimethyl-1,2,3,4-tetrahydroisoquinolin-7-amine (400 mg, 92%) as a brown oil. ¹H NMR (DMSO-d₆, 300 MHz) δ 6.95 (d, J=8.1 Hz, 1H), 6.38 (dd, J=7.8, 1.8 Hz, 1H), 6.16 (d, J=1.8 Hz, 1H), 4.77 (s, 2H), 3.28 (s, 2H), 2.27 (s, 3H), 2.25 (s, 2H), 1.15 (s, 6H).

Example 12 was synthesized according to General Procedure A using 2,4,4-trimethyl-1,2,3,4-tetrahydroisoquinolin-7-amine. ¹H NMR (DMSO-d₆, 300 MHz) δ 10.22 (br s, 1H), 8.87 (s, 1H), 8.01 (t, J=8.1 Hz, 1H), 7.76 (d, J=8.1 Hz, 1H), 7.64 (d, J=7.5 Hz, 1H), 7.54 (br s, 1H), 7.41 (d, J=8.1 Hz, 1H), 7.28 (d, J=8.4 Hz, 1H), 5.75-5.60 (m, 1H), 5.35 (s, 1H), 4.99 (d, J=10.8 Hz, 1H), 4.81 (d, J=16.8 Hz, 1H), 4.68 (d, J=5.7 Hz, 2H), 3.43 (s, 2H), 2.35 (s, 3H), 2.33 (s, 2H), 1.46 (s, 6H), 1.23 (s, 6H); MS (LCMS) m/z 500.3 [M+H]⁺.

Example 13

2-Allyl-6-((2-(2-hydroxyethyl)-1,2,3,4-tetrahydroisoquinolin-7-yl)amino)-1-(6-(2-hydroxypropan-2-yl)pyridin-2-yl)-1,2-dihydro-3H-pyrazolo[3,4-d]pyrimidin-3-one hydrochloride

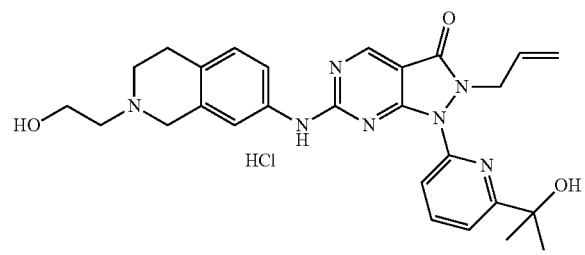 [SMILES: C=CCn1c(=O)c2cnc(Nc3ccc4c(c3)CN(CCO)CC4)nc2n1-c1cccc(C(C)(C)O)n1 ; Cl]

To a stirred solution of 7-nitro-1,2,3,4-tetrahydroisoquinoline (3.0 g, 16.85 mmol) in DMF (80 mL) was added K₂CO₃ (9.3 g, 67.42 mmol) followed by (2-bromoethoxy)(tert-butyl)dimethylsilane (8.0 g, 33.71 mmol). The reaction was stirred at RT for 6 h. Water (200 mL) was added, and the mixture was extracted with Et₂O (2×200 mL). The combined organic layers were washed with brine (100 mL), dried (Na₂SO₄) and concentrated. The crude mixture was purified by column chromatography (SiO₂, 15% EA/pet. ether) to afford 2-(2-(tert-butyldimethylsilyloxy)ethyl)-7-nitro-1,2,3,4-tetrahydroisoquinoline (2.0 g, 35%) as a brown oil; MS (LCMS) m/z 337.2 [M+H]⁺.

To a stirred solution of 2-(2-(tert-butyldimethylsilyloxy)ethyl)-7-nitro-1,2,3,4-tetrahydroisoquinoline (1.0 g, 2.98 mmol) in EtOH (50 mL) was added SnCl₂ (3.38 g, 17.86 mmol) followed by NH₄Cl (0.946 g, 17.86 mmol) at RT. The reaction was stirred at 70° C. for 1 h. After completion, the solvent was removed in vacuo, diluted with water, basified with sat. NaHCO₃ solution (pH 8-9), and filtered through a celite pad. The mixture was extracted with 30% MeOH:DCM (3×100 mL), dried (Na₂SO₄), and concentrated to afford 2-(2-(tert-butyldimethyl-silyloxy)ethyl)-1,2,3,4-tetrahydroisoquinolin-7-amine (750 mg, 82%) as a brown semi solid; MS (LCMS) m/z 307.2 [M+H]⁺.

2-Allyl-6-(2-(2-(tert-butyldimethylsilyloxy)ethyl)-1,2,3,4-tetrahydroisoquinolin-7-ylamino)-1-(6-(2-hydroxypropan-2-yl)pyridin-2-yl)-1H-pyrazolo[3,4-d]pyrimidin-3(2H)-one was prepared according to General Procedure A using 2-(2-(tert-butyldimethyl-silyloxy)ethyl)-1,2,3,4-tetrahydroisoquinolin-7-amine; MS (LCMS) m/z 616.4 [M+H]⁺.

To a stirred solution of 2-allyl-6-(2-(2-(tert-butyldimethylsilyloxy)ethyl)-1,2,3,4-tetrahydroisoquinolin-7-ylamino)-1-(6-(2-hydroxypropan-2-yl)pyridin-2-yl)-1H-pyrazolo[3,4-d]pyrimidin-3(2H)-one (130 mg, 0.21 mmol) in 1,4-dioxane (2 mL) was added 4.0 M HCl in 1,4-dioxane (2 mL) at 0° C. The ice bath was removed, and the reaction was stirred at RT for 1 h. The reaction mixture was concentrated in vacuo and co-distilled with diethyl ether (2×) to afford Example 13 (103 mg, 97%) as an off white solid. mp: 210-212° C.; ¹H NMR (DMSO-d₆, 400 MHz) δ 10.47 (brs, 1H), 10.35 (brs, 1H), 8.90 (s, 1H), 8.09 (t, J=8.0 Hz, 1H), 7.78 (d, J=7.6 Hz, 1H), 7.74 (s, 1H), 7.64 (d, J=8.0 Hz, 1H), 7.52 (d, J=6.8 Hz, 1H), 7.20 (d, J=8.8 Hz, 1H), 5.72-5.61 (m, 1H), 4.99 (d, J=9.6 Hz, 1H), 4.82 (d, J=17.2 Hz, 1H), 4.69 (d, J=5.6 Hz, 2H), 4.58-4.49 (m, 1H), 4.44-4.34 (m, 1H), 3.93-3.86 (m, 3H), 3.41-3.30 (m, 3H), 3.25-3.12 (m, 1H), 3.01-2.93 (m, 1H), 1.46 (s, 6H); MS (LCMS) m/z 502.3 [M+H]⁺.

Example 14

2-Allyl-1-(6-(2-hydroxypropan-2-yl)pyridin-2-yl)-6-((2-(oxetan-3-yl)-1,2,3,4-tetrahydroisoquinolin-7-yl)amino)-1,2-dihydro-3H-pyrazolo[3,4-d]pyrimidin-3-one

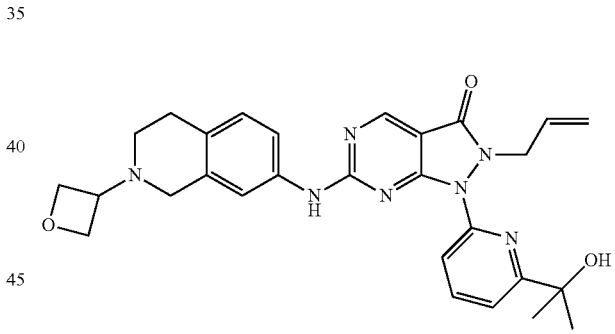

To a stirred solution of 7-nitro-1,2,3,4-tetrahydroisoquinoline (850 mg, 4.77 mmol) in MeOH (10 mL) were added oxetan-3-one (152 mg, 0.77 mmol) and ZnCl₂ (1.7 g, 23.87 mmol) followed by NaCNBH₃ (3.2 g, 23.87 mmol) at 0° C. The ice bath was removed, and the reaction was stirred at RT for 3 h. The reaction was diluted with water (25 mL) and extracted with EA (3×20 mL). The organic layers were dried (Na₂SO₄), filtered and concentrated in vacuo. The crude compound was purified by column chromatography (neutral alumina) to afford 7-nitro-2-(oxetan-3-yl)-1,2,3,4-tetrahydroisoquinoline (750 mg, 68%) as an off-white solid. MS (ESI) m/z 235.3 [M+H]⁺.

To a stirred solution of 7-nitro-2-(oxetan-3-yl)-1,2,3,4-tetrahydroisoquinoline (750 mg, 3.20 mmol) in MeOH (5 mL) was added 10% wet Pd/C (150 mg, 20% w/w). The reaction was stirred for 16 h under H₂. The reaction was filtered through a celite pad, and the filtrate was concentrated in vacuo to afford 2-(oxetan-3-yl)-1,2,3,4-tetrahydroisoquinolin-7-amine (600 mg, 91%); MS (ESI) m/z 205.3 [M+H]⁺.

Example 14 was prepared according to General Procedure A using 2-(oxetan-3-yl)-1,2,3,4-tetrahydroisoquinolin-7-amine. $^1$H NMR (400 MHz, DMSO-$d_6$) δ 10.26 (br s, 1H), 8.87 (s, 1H), 7.98-7.94 (m, 1H), 7.75 (d, J=8.4 Hz, 1H), 7.63 (d, J=7.2 Hz, 2H), 7.38 (d, J=7.6 Hz, 1H), 7.06 (d, J=8.4 Hz, 1H), 5.71-5.62 (m, 1H), 5.35 (s, 1H), 4.99 (d, J=10.0 Hz, 1H), 4.81 (d, J=18.0 Hz, 1H), 4.69-4.64 (m, 4H), 4.55 (t, J=6.0 Hz, 2H), 3.65-3.60 (m, 1H), 3.42 (s, 2H), 2.79-2.74 (m, 2H), 2.54-2.49 (m, 2H), 1.45 (s, 6H); MS (ESI) m/z 514.2 [M+H]$^+$.

Example 15

2-Allyl-1-(6-(2-hydroxypropan-2-yl)pyridin-2-yl)-6-((1,2,3,4-tetrahydroisoquinolin-6-yl)amino)-1,2-dihydro-3H-pyrazolo[3,4-d]pyrimidin-3-one hydrogen chloride

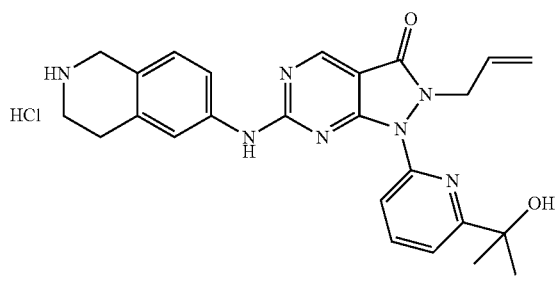 [SMILES: Cl ; C=CCn1c(=O)c2cnc(Nc3ccc4c(c3)CCNC4)nc2n1-c1cccc(C(C)(C)O)n1]

Tert-butyl 6-((2-allyl-1-(6-(2-hydroxypropan-2-yl)pyridin-2-yl)-3-oxo-2,3-dihydro-1H-pyrazolo[3,4-d]pyrimidin-6-yl)amino)-3,4-dihydroisoquinoline-2(1H)-carboxylate was prepared according to General Procedure A using tert-butyl 6-amino-3,4-dihydroisoquinoline-2(1H)-carboxylate; MS (ESI) m/z 558.3 [M+H]$^+$.

To a solution of tert-butyl 6-(2-allyl-1-(6-(2-hydroxypropan-2-yl)pyridin-2-yl)-3-oxo-2,3-dihydro-1H-pyrazolo[3,4-d]pyrimidin-6-yl-amino)-3,4-dihydroisoquinoline-2(1H)-carboxylate (120 mg, 0.22 mmol) in 1,4-dioxane (5 mL) was added 4M HCl in 1,4-dioxane (10 mL) at 0° C. The ice bath was removed, and the reaction was stirred at RT for 2 h. The reaction was concentrated under reduced pressure. Diethyl ether was added, and the reaction concentrated. This process was repeated followed by drying at high vacuum to afford Example 15 (114 mg) as an off-white solid. $^1$H NMR (400 MHz, DMSO-$d_6$) δ 10.36 (s, 1H), 9.16 (br s, 2H), 8.90 (s, 1H), 8.04 (t, J=8.0 Hz, 1H), 7.82-7.74 (m, 2H), 7.64 (d, J=8.0 Hz, 1H), 7.49 (d, J=8.4 Hz, 1H), 7.17 (d, J=8.8 Hz, 1H), 5.72-5.60 (m, 1H), 5.32 (s, 1H), 4.99 (d, J=10.0 Hz, 1H), 4.82 (d, J=17.2 Hz, 1H), 4.74-4.68 (m, 2H), 4.22 (s, 2H), 3.45-3.38 (m, 2H), 3.00 (t, J=6.0 Hz, 2H), 1.46 (s, 6H); MS (ESI) m/z 458.3 [M+H]$^+$.

Example 16

2-Allyl-1-(6-(2-hydroxypropan-2-yl)pyridin-2-yl)-6-((2-methyl-1,2,3,4-tetrahydroisoquinolin-6-yl)amino)-1,2-dihydro-3H-pyrazolo[3,4-d]pyrimidin-3-one

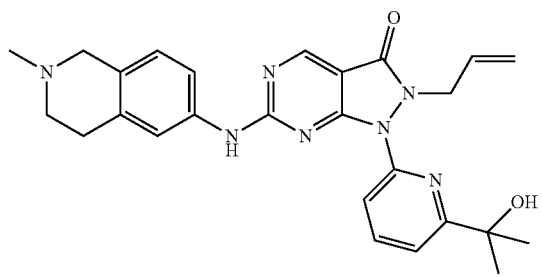 [SMILES: C=CCn1c(=O)c2cnc(Nc3ccc4c(c3)CCN(C)C4)nc2n1-c1cccc(C(C)(C)O)n1]

To a stirred solution of tert-butyl-6-amino-3,4-dihydroisoquinoline-2(1H)-carboxylate (500 mg, 2.01 mmol) in THF (10 mL) was added LiAlH$_4$ (382 mg, 10.07 mmol) at 0° C. The ice bath was removed, and the reaction was stirred at 60° C. for 16 h. The reaction was quenched with sat. Na$_2$SO$_4$, and the reaction was then filtered through a celite pad. The filtrate was dried (Na$_2$SO$_4$), filtered and concentrated in vacuo to afford 2-methyl-1,2,3,4-tetrahydroisoquinolin-6-amine (350 mg) as a brown semi-solid. MS (ESI) m/z 163.0 [M+H]$^+$.

Example 16 was synthesized according to General Procedure A using 2-methyl-1,2,3,4-tetrahydroisoquinolin-6-amine. $^1$H NMR (400 MHz, DMSO-$d_6$) δ 10.2 (br s, 1H), 8.86 (s, 1H), 8.01 (t, J=8.0 Hz, 1H), 7.77 (d, J=7.6 Hz, 1H), 7.63 (d, J=8.0 Hz, 2H), 7.37 (d, J=7.6 Hz, 1H), 6.99 (d, J=8.4 Hz, 1H), 5.72-5.60 (m, 1H), 5.30 (s, 1H), 4.99 (d, J=10.0 Hz, 1H), 4.82 (d, J=17.2 Hz, 1H), 4.69 (d, J=6.0 Hz, 2H), 3.43 (s, 2H), 2.85-2.78 (m, 2H), 2.68-2.58 (m, 2H), 2.33 (s, 3H), 1.46 (s, 6H); MS (ESI) m/z 472.2 [M+H]$^+$.

Example 17

2-Allyl-6-((2-(2-hydroxyethyl)-1,2,3,4-tetrahydroisoquinolin-6-yl)amino)-1-(6-(2-hydroxypropan-2-yl)pyridin-2-yl)-1,2-dihydro-3H-pyrazolo[3,4-d]pyrimidin-3-one hydrogen chloride

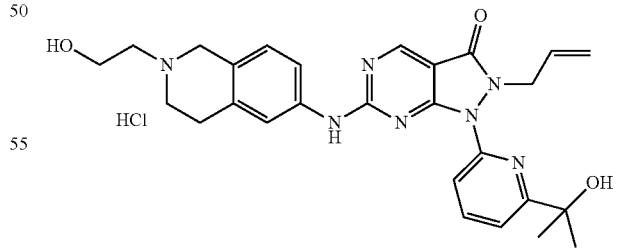

To a stirred solution of tert-butyl 6-amino-3,4-dihydroisoquinoline-2(1H)-carboxylate (4 g, 16.13 mmol) in toluene (40 mL) was added DIPEA (2.82 mL, 16.13 mmol) followed by phthalic anhydride (2.63 g, 17.74 mmol). The reaction was stirred at reflux for 16 h. After completion, the reaction was cooled to RT, diluted with EA (200 mL) and washed with sat. NaHCO$_3$ (2×50 mL), water (50 mL) and brine (50 mL). The organic layers were dried (Na$_2$SO$_4$), filtered and evaporated under vacuum to afford tert-butyl 6-(1,3-dioxoisoindolin-2-yl)-3,4-dihydroisoquinoline-2(1H)-carboxylate (5.1 g, 85% yield) as a light brown solid; MS (ESI) m/z 401.3 [M+Na]$^+$.

To a stirred solution of tert-butyl 6-(1,3-dioxoisoindolin-2-yl)-3,4-dihydroisoquinoline-2(1H)-carboxylate (2 g, 5.29 mmol) in CH$_2$Cl$_2$ (20 mL) was added 4 M HCl in dioxane (20 mL) at 0° C. The ice bath was removed, and the reaction was stirred at RT for 2 h. After completion of the reaction by TLC, the solvent was evaporated under reduced pressure. The crude residue was triturated with n-pentane to afford 2-(1,2,3,4-tetrahydroisoquinolin-6-yl) isoindoline-1,3-dione hydrochloride (1.6 g, 94%) as an off white solid. MS (ESI) m/z 279.4 [M+H]$^+$.

To a RT solution of 2-(1,2,3,4-tetrahydroisoquinolin-6-yl) isoindoline-1,3-dione hydrochloride (2 g, 7.19 mmol) in acetone (20 mL), were added (2-bromoethoxy)(tert-butyl)dimethylsilane (2.58 g, 10.79 mmol) followed by K$_2$CO$_3$ (2.98 g, 21.58 mmol). The reaction was stirred at 50° C. for 24 h. Upon completion, the reaction was diluted with EA (200 mL) and washed with sat. NaHCO$_3$ (100 mL), water (100 mL) and brine (100 mL). The organic layer was dried (Na$_2$SO$_4$) and evaporated under vacuum. The crude was purified by column chromatography (SiO$_2$, 5% EA/pet. ether) to afford 2-(2-(2-((tert-butyldimethylsilyl)oxy)ethyl)-1,2,3,4-tetrahydroisoquinolin-6-yl)isoindoline-1,3-dione (1.1 g, 35%) as an off-white solid; MS (ESI) m/z 437.5 [M+H]$^+$.

To a stirred solution of 2-(2-(2-((tert-butyldimethylsilyl)oxy)ethyl)-1,2,3,4-tetrahydroisoquinolin-6-yl)isoindoline-1,3-dione (500 mg, 1.14 mmol) in EtOH:H$_2$O (9:1, 10 mL) was added NH$_2$NH$_2$ (0.07 mL, 2.29 mmol). The reaction was stirred at RT for 1 h. After completion of the reaction by TLC, the reaction was concentrated, dissolved in DCM (10 mL) and stirred for 10 mins. The reaction mixture was then filtered to separate the precipitated solid. The filtrate was evaporated under reduced pressure to afford 2-(2-((tert-butyldimethylsilyl)oxy)ethyl)-1,2,3,4-tetrahydroisoquinolin-6-amine (240 mg, 68%) as a yellow solid; MS (ESI) m/z 307.4 [M+H]$^+$.

2-allyl-6-((2-(2-((tert-butyldimethylsilyl)oxy)ethyl)-1,2,3,4-tetrahydroisoquinolin-6-yl)amino)-1-(6-(2-hydroxypropan-2-yl)pyridin-2-yl)-1,2-dihydro-3H-pyrazolo[3,4-d]pyrimidin-3-on was synthesized according to General Procedure A using 2-(2-((tert-butyldimethylsilyl)oxy)ethyl)-1,2,3,4-tetrahydroisoquinolin-6-amine; MS (ESI) m/z 617.1 [M+H]$^+$.

To a 0° C. stirred solution of 2-allyl-6-((2-(2-((tert-butyldimethylsilyl)oxy)ethyl)-1,2,3,4-tetrahydroisoquinolin-6-yl)amino)-1-(6-(2-hydroxypropan-2-yl)pyridin-2-yl)-1,2-dihydro-3H-pyrazolo[3,4-d]pyrimidin-3-one (300 mg, 0.49 mmol) in dioxane (4 mL) was added 4 M HCl in dioxane (1 mL). The ice bath was removed, and the reaction was stirred at RT for 2 h. After completion of the reaction by TLC, the solvent was removed under reduced pressure, and the residue was triturated with diethyl ether to afford Example 17 (233 mg, 95%) as a yellow solid. $^1$H NMR (400 MHz, DMSO-d$_6$) δ 10.46 (br s, 1H), 10.34 (br s, 1H), 8.91 (s, 1H), 8.07 (t, J=8.0 Hz, 1H), 7.82 (br s, 1H), 7.78 (d, J=6.3 Hz, 1H), 7.64 (d, J=7.2 Hz, 1H), 7.49 (d, J=8.8 Hz, 1H), 7.16 (d, J=8.4 Hz, 1H), 5.72-5.64 (m, 1H), 4.99 (dd, J=10.0, 0.8 Hz, 1H), 4.81 (dd, J=17.2, 1.2 Hz, 1H), 4.70 (d, J=4.8 Hz, 2H), 4.50 (d, J=14.4 Hz, 1H), 4.34-4.26 (m, 1H), 3.86 (t, J=5.6 Hz, 2H), 3.80-3.73 (m, 1H), 3.44-3.19 (m, 4H), 3.05-2.97 (m, 1H), 1.46 (s, 6H); MS (ESI) m/z 502.5 [M+H]$^+$.

Example 18

2-Allyl-1-(6-(2-hydroxypropan-2-yl)pyridin-2-yl)-6-((2-(oxetan-3-yl)-1,2,3,4-tetrahydroisoquinolin-6-yl)amino)-1,2-dihydro-3H-pyrazolo[3,4-d]pyrimidin-3-one

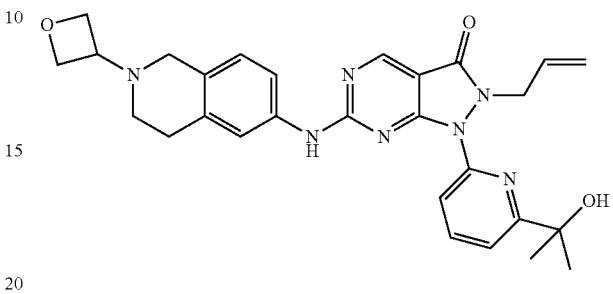

To a stirred 0° C. solution of tert-butyl 6-amino-3,4-dihydroisoquinoline-2(1H)-carboxylate (1 g, 4.02 mmol) in DCM (15 mL) was added Et$_3$N (1.7 mL, 12.07 mmol) followed by (CF$_3$CO)$_2$O (0.85 mL, 6.03 mmol). The ice bath was removed, and the reaction was stirred at RT for 2 h. After completion of the reaction, the reaction was diluted with DCM (20 mL) washed with sat. NaHCO$_3$ (2×20 mL), water (20 mL) and brine (20 mL), dried (Na$_2$SO$_4$) and evaporated under vacuum to afford tert-butyl 6-(2,2,2-trifluoroacetamido)-3,4-dihydro isoquinoline-2(1H)-carboxylate (1.2 g, 81%) as a brown solid; MS (ESI) m/z 289.4 [(M-tBu)+H]$^+$.

To a stirred 0° C. solution of tert-butyl-6-(2,2,2-trifluoroacetamido)-3,4-dihydroisoquinoline-2(1H)-carboxylate (5.7 g, 16.56 mmol) in DCM (30 mL) was added 4 M HCl in dioxane (30 mL). The ice bath was removed, and the reaction was stirred at RT for 2 h. The solvent was removed, and the residue was treated with sat. aq. NaHCO$_3$ (100 mL) and extracted with DCM (3×100 mL). The combined organic layers were washed with water (100 mL) and brine (100 mL), dried (Na$_2$SO$_4$) and evaporated under vacuum to afford 2,2,2-trifluoro-N-(1,2,3,4-tetrahydroisoquinolin-6-yl) acetamide (3.8 g, 94%). MS (ESI) m/z 245.3 [M+H]$^+$.

To a solution of 2,2,2-trifluoro-N-(1,2,3,4-tetrahydroisoquinolin-6-yl)acetamide (3.8 g, 15.57 mmol) in DCM (38 mL) was added oxetan-3-one (1.12 g, 15.57 mmol) and a catalytic amount of AcOH. The reaction was stirred at RT for 1 h. Na(OAc)$_3$BH (9.9 g, 46.72 mmol) was added, and the reaction was stirred at RT for 16 h. After completion of the reaction by TLC, the reaction was diluted with DCM (100 mL) and washed sat. NaHCO$_3$ solution. The separated organic layer was washed with water (100 mL) and brine (100 mL), dried (Na$_2$SO$_4$) and evaporated under vacuum to afford 2,2,2-trifluoro-N-(2-(oxetan-3-yl)-1,2,3,4-tetrahydroisoquinolin-6-yl)acetamide (2.8 g, 60%); MS (ESI) m/z 301.3 [M+H]$^+$.

To a stirred RT solution of 2,2,2-trifluoro-N-(2-(oxetan-3-yl)-1,2,3,4-tetrahydroisoquinolin-6-yl)acetamide (450 mg, 1.50 mmol) in MeOH (5 mL) was added K$_2$CO$_3$ (0.62 g, 4.50 mmol). The reaction was stirred at 70° C. for 32 h. The reaction was filtered, and the filtrate was evaporated. The crude material was purified column chromatography (SiO$_2$, 30% EA/pet. ether) to afford 2-(oxetan-3-yl)-1,2,3,4-tetrahydroisoquinolin-6-amine (220 mg, 72%); MS (ESI) m/z 205.2 [M+H]$^+$.

Example 18 was prepared according to General Procedure A using 2-(oxetan-3-yl)-1,2,3,4-tetrahydroisoquinolin-6-amine. $^1$H NMR (400 MHz, DMSO-d$_6$) δ 10.30 (br s, 1H), 8.88 (s, 1H), 8.03 (t, J=7.6 Hz, 1H), 7.77 (d, J=8.0 Hz, 1H), 7.69 (br s, 1H), 7.62 (d, J=8.0 Hz, 1H), 7.37 (d, J=8.8 Hz, 1H), 7.00 (d, J=8.4 Hz, 1H), 5.70-5.63 (m, 1H), 5.34 (s, 1H), 4.99 (d, J=10.4 Hz, 1H), 4.81 (d, J=17.2 Hz, 1H), 4.69 (d, J=6.0 Hz, 2H), 4.62 (t, J=6.4 Hz, 2H), 4.53 (t, J=5.6 Hz, 2H), 3.58 (t, J=6.4 Hz, 1H), 3.40 (s, 2H). 2.82 (t, J=5.6 Hz, 2H), 2.55-2.50 (m, 2H), 1.46 (s, 6H); MS (ESI) m/z 514.5.

Example 19

7-((2-Allyl-1-(6-(2-hydroxypropan-2-yl)pyridin-2-yl)-3-oxo-2,3-dihydro-1H-pyrazolo[3,4-d]pyrimidin-6-yl)amino)-3,4-dihydroisoquinolin-1(2H)-one

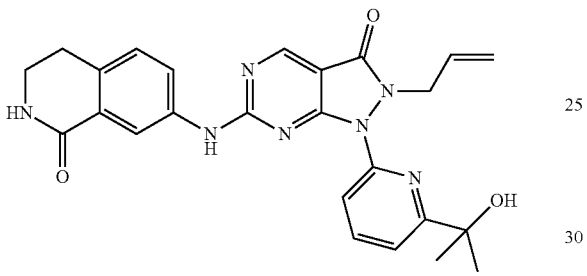

Example 19 was prepared according to General Procedure B using commercially available 7-amino-3,4-dihydroisoquinolin-1(2H)-one. $^1$H NMR (DMSO-d$_6$, 400 MHz) δ 10.43 (brs, 1H), 8.90 (s, 1H), 8.51 (brs, 1H), 8.06 (t, J=10.8 Hz, 1H), 8.02-7.97 (m, 1H), 7.89 (d, J=10.8 Hz, 1H), 7.68 (d, J=8.8 Hz, 1H), 7.59 (d, J=10.4 Hz, 1H), 7.27 (d, J=10.8 Hz, 1H), 5.74-5.61 (m, 1H), 5.31 (s, 1H), 4.99 (d, J=14.0 Hz, 1H), 4.86-4.77 (m, 1H), 4.72 (d, J=7.6 Hz, 2H), 3.42-3.35 (m, 2H), 2.86 (t, J=8.4 Hz, 2H), 1.45 (s, 6H); MS (ESI) m/z 472.2 [M+H]$^+$.

Example 20

7-((2-Allyl-1-(6-(2-hydroxypropan-2-yl)pyridin-2-yl)-3-oxo-2,3-dihydro-H-pyrazolo[3,4-d]pyrimidin-6-yl)amino)-2-methyl-3,4-dihydroisoquinolin-1(2H)-one

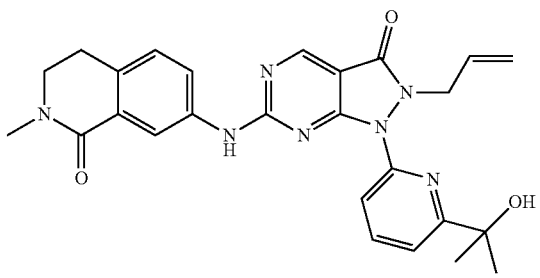 [SMILES: C=CCn1c(=O)c2cnc(Nc3ccc4c(c3)C(=O)N(C)CC4)nc2n1-c1cccc(C(C)(C)O)n1]

7-Amino-2-methyl-3,4-dihydroisoquinolin-1(2H)-one was prepared according to WO 2016/086200, which is hereby incorporated by reference for the limited purpose of the synthesis of 7-Amino-2-methyl-3,4-dihydroisoquinolin-1(2H)-one.

Example 20 was prepared according to General Procedure A using 7-amino-2-methyl-3,4-dihydroisoquinolin-1(2H)-one. $^1$H NMR (400 MHz, DMSO-d$_6$) δ 10.38 (br s, 1H), 8.89 (s, 1H), 8.47 (br s, 1H), 8.04 (t, J=8.0 Hz, 1H), 7.89 (d, J=8.4 Hz, 1H), 7.74-7.68 (m, 1H), 7.59 (d, J=7.6 Hz, 1H), 7.24 (d, J=8.4 Hz, 1H), 5.73-5.63 (m, 1H), 5.28 (s, 1H), 5.00 (d, J=10.4 Hz, 1H), 4.82 (d, J=17.2 Hz, 1H), 4.71 (d, J=6.0 Hz, 2H), 3.55 (t, J=6.0 Hz, 2H). 3.08 (s, 3H), 2.94 (t, J=6.8 Hz, 2H), 1.45 (s, 6H); MS (ESI) m/z 486.3 [M+H]$^+$.

Example 21

2-Allyl-1-(6-(2-hydroxypropan-2-yl)pyridin-2-yl)-6-(isoindolin-5-ylamino)-1,2-dihydro-3H-pyrazolo[3,4-d]pyrimidin-3-one hydrogen chloride

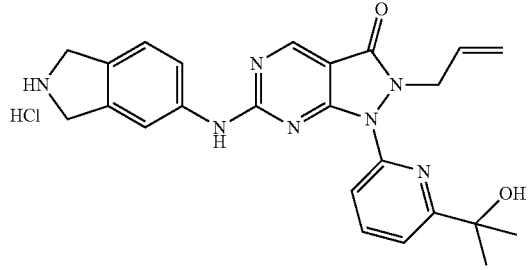 [SMILES: Cl ; C=CCn1c(=O)c2cnc(Nc3ccc4c(c3)CNC4)nc2n1-c1cccc(C(C)(C)O)n1]

Tert-butyl-5-((2-allyl-1-(6-(2-hydroxypropan-2-yl)pyridin-2-yl)-3-oxo-2,3-dihydro-1H-pyrazolo[3,4-d]pyrimidin-6-yl)amino)-isoindoline-2-carboxylate was prepared according the General Procedure A using tert-butyl 5-aminoisoindoline-2-carboxylate; MS (ESI) m/z 544.3 [M+H]$^+$.

To a stirred 0° C. solution of tert-butyl-5-((2-allyl-1-(6-(2-hydroxypropan-2-yl)pyridin-2-yl)-3-oxo-2,3-dihydro-1H-pyrazolo[3,4-d]pyrimidin-6-yl)amino)isoindoline-2-carboxylate (105 mg, 0.19 mmol) in 1,4-dioxane (2 mL), was added 4M HCl in 1,4-dioxane (3 mL). The ice bath was removed, and the reaction was stirred at RT for 2 h. The reaction mixture was concentrated under reduced pressure and co-distilled with Et$_2$O to afford Example 21 (90 mg) as an off-white solid. $^1$H NMR (400 MHz, DMSO-d$_6$) δ 10.42 (br s, 1H), 9.58 (br s, 2H), 8.91 (s, 1H), 8.04 (t, J=8.0 Hz, 1H), 7.90 (s, 1H), 7.77 (d, J=8.0 Hz, 1H), 7.62 (t, J=7.6 Hz, 2H), 7.35 (d, J=8.4 Hz, 1H), 5.73-5.62 (m, 1H), 4.99 (d, J=10.0 Hz, 1H), 4.82 (d, J=16.4 Hz, 1H), 4.69 (d, J=6.0 Hz, 2H), 4.54-4.46 (m, 4H), 1.46 (s, 6H); MS (ESI) m/z 444.2 [M+H]$^+$.

Example 22

2-allyl-6-((2-(dimethylamino)-2,3-dihydro-1H-inden-5-yl)amino)-1-(6-(2-hydroxypropan-2-yl)pyridin-2-yl)-1,2-dihydro-3H-pyrazolo[3,4-d]pyrimidin-3-one

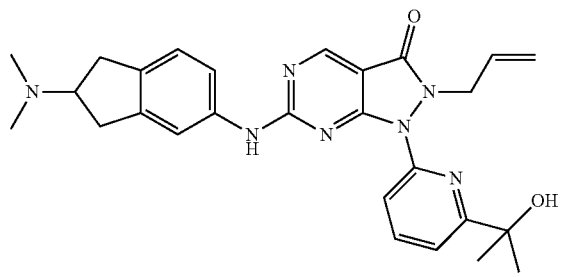 [SMILES: C=CCn1c(=O)c2cnc(Nc3ccc4c(c3)CC(N(C)C)C4)nc2n1-c1cccc(C(C)(C)O)n1]

To a stirred solution of 5-nitro-1H-inden-2(3H)-one (1 g, 5.65 mmol) in DCM (15 mL) was added AcOH (1.6 mL, 28.25 mmol) followed by N,N-dimethylamine (2M in THF) (5.6 mL, 11.30 mmol) at 0° C. After 15 mins, NaCNBH$_3$ (4.79 g, 22.60 mmol) was added. The ice bath was removed, and the reaction was stirred at RT for 16 h. The reaction was concentrated, diluted with water, and the pH was adjusted to 11 with 1N NaOH. The mixture was extracted with 5% MeOH:DCM (2×300 mL). The combined organic layers were washed with water (15 mL), dried (Na$_2$SO$_4$) and concentrated to afford N,N-dimethyl-5-nitro-2,3-dihydro-1H-inden-2-amine (1.1 g, 94%) as a dark oil; MS (LCMS) m/z 207.0.

To a stirred RT solution of N,N-dimethyl-5-nitro-2,3-dihydro-1H-inden-2-amine (1.09 g, 5.27 mmol) in EtOH (50 mL) was added SnCl$_2$ (5.5 g, 28.98 mmol) followed by NH$_4$Cl (1.54 g, 28.98 mmol). The reaction was stirred at 70° C. for 1 h. After completion, the reaction was concentrated under reduced pressure, diluted with water and the pH was adjusted with sat. NaHCO$_3$ (pH 8-9). The reaction was filtered through a celite pad, extracted with 30% MeOH:DCM (3×100 mL) and concentrated to afford N,N-dimethyl-2,3-dihydro-1H-indene-2,5-diamine (550 mg, 59%) as a brown solid; MS (LCMS) m/z 177.1 [M+H]$^+$.

Example 22 was prepared according to General Procedure A using N,N-dimethyl-2,3-dihydro-1H-indene-2,5-diamine. mp: 186-188° C.; $^1$H NMR (DMSO-d$_6$, 400 MHz) δ 10.18 (br s, 1H), 8.85 (s, 1H), 7.99 (t, J=8.0 Hz, 1H), 7.76 (d, J=7.6 Hz, 1H), 7.68-7.64 (m, 1H), 7.62 (d, J=8.0 Hz, 1H), 7.40 (d, J=7.6 Hz, 1H), 7.12 (d, J=8.4 Hz, 1H), 5.72-5.61 (m, 1H), 5.29 (s, 1H), 4.99 (d, J=9.6 Hz, 1H), 4.82 (d, J=17.2 Hz, 1H), 4.68 (d, J=6.0 Hz, 2H), 3.04-2.89 (m, 3H), 2.80-2.65 (m, 2H), 2.20 (s, 6H), 1.46 (s, 6H); MS (LCMS) m/z 486.3 [M+H]$^+$.

Example 23

2-Allyl-1-(6-(2-hydroxypropan-2-yl)pyridin-2-yl)-6-((2-methylisoindolin-5-yl)amino)-1,2-dihydro-3H-pyrazolo[3,4-d]pyrimidin-3-one

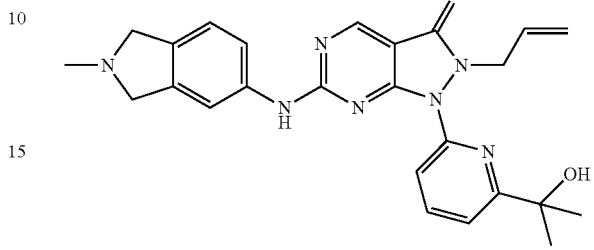

Example 23 was prepared according to General Procedure A using commercially available 2-methylisoindolin-5-amine. $^1$H NMR (400 MHz, DMSO-d$_6$) δ 10.29 (br s, 1H), 8.88 (s, 1H), 8.01 (t, J=8.0 Hz, 1H), 7.76 (d, J=8.4 Hz, 2H), 7.63 (d, J=9.6 Hz, 1H), 7.44 (d, J=9.6 Hz, 1H), 7.16 (d, J=8.4 Hz, 1H), 5.72-5.60 (m, 1H), 5.34 (s, 1H), 4.99 (d, J=10.4 Hz, 1H), 4.81 (d, J=18.4 Hz, 1H), 4.69 (d, J=6.0 Hz, 2H), 3.80 (s, 2H), 3.76 (s, 2H), 2.49 (s, 3H), 1.45 (s, 6H); MS (ESI) m/z 458.2 [M+H]$^+$.

Example 24

2-Allyl-1-(6-(2-hydroxypropan-2-yl)pyridin-2-yl)-6-((7-methyl-5,6,7,8-tetrahydro-1,7-naphthyridin-2-yl)amino)-1,2-dihydro-3H-pyrazolo[3,4-d]pyrimidin-3-one

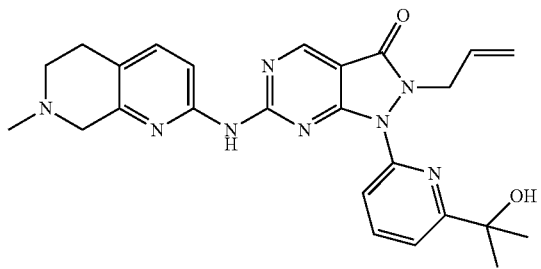 [SMILES: C=CCn1c(=O)c2cnc(Nc3ccc4c(n3)CN(C)CC4)nc2n1-c1cccc(C(C)(C)O)n1]

In a pressure tube, to a stirred solution of 4-iodopyridin-3-amine (12 g, 54.54 mmol) in DMF (50 mL) was added TEA (11.01 g, 109.08 mmol), Pd(OAc)$_2$ (3.67 g, 5.45 mmol), and (O-tolyl)$_3$P (3.32 g, 10.90 mmol). The solution was degassed with argon, followed by addition of ethyl acrylate (6.544 g, 65.44 mmol). The reaction mixture was heated at 80° C. for 16 h. The reaction was diluted with EA (200 mL), washed with water (2×100 mL), brine (150 mL), dried (Na$_2$SO$_4$), filtered and concentrated under reduced pressure. The crude mixture was purified by column chromatography (SiO$_2$, EA/pet. ether) to afford ethyl (E)-3-(3-aminopyridin-4-yl) acrylate (6.0 g, 57%) as a semi-solid; MS (ESI) m/z 193.0 [M+H]$^+$.

To a stirred solution of ethyl (E)-3-(3-aminopyridin-4-yl) acrylate (5.0 g, 26.04 mmol) in EtOH (60 mL) was added NaOEt (21% in EtOH w/v, 42 mL, 130.2 mmol) at RT. The reaction was stirred at 80° C. for 2 h. The reaction was concentrated under reduced pressure. The crude mixture was purified by column chromatography (SiO$_2$, 3% MeOH/DCM) to afford 1,7-naphthyridin-2(1H)-one (900 mg, 23%) as an off-white solid; MS (ESI) m/z 147.0[M+H]$^+$.

1,7-naphthyridin-2(1H)-one (900 mg, 6.16 mmol) was suspended in EtOH (6 mL) and heated at 70° C. for 10 mins. Benzyl bromide (6 mL) was added. The mixture was refluxed for 16 h and then cooled to RT. The precipitated solid was filtered, washed with EtOH and dried under vacuum to afford 7-benzyl-2-oxo-1,2-dihydro-1,7-naphthyridin-7-ium (1.3 g, 89%) as an off-white solid. MS (ESI) m/z 237.1 [M+H]$^+$.

To a stirred 0° C. solution of 7-benzyl-2-oxo-1,2-dihydro-1,7-naphthyridin-7-ium (1.3 g, 5.49 mmol) in EtOH (10 mL) was added NaBH$_4$ (1.037 g, 27.42 mmol). The reaction was stirred for 30 mins at 0° C. The reaction was warmed to RT and 6N HCl (3 mL) was added. The mixture was stirred at RT for 90 mins. The pH was adjusted to 10 using 2N NaOH solution and then extracted with EA (2×100 mL). The combined organic layers were dried (Na$_2$SO$_4$), filtered and concentrated under reduced pressure to obtain 7-benzyl-5,6,7,8-tetrahydro-1,7-naphthyridin-2(1H)-one (850 mg) as an off-white solid; MS (ESI) m/z 241.1 [M+H]$^+$.

In a steel bomb, to a stirred solution of 7-benzyl-5,6,7,8-tetrahydro-1,7-naphthyridin-2(1H)-one (900 mg, 3.75 mmol) in MeOH (8.0 mL) was added Pd/C (300 mg) and TFA (0.5 mL). The reaction was stirred at RT under H$_2$ atmosphere (50 psi) for 5 h. The reaction was filtered through a celite pad, and the filtrate was concentrated under reduced pressure to afford 5,6,7,8-tetrahydro-1,7-naphthyridin-2(1H)-one (TFA salt) (700 mg, 66%) as a semi-solid; MS (ESI) m/z 151.0 [M+H]$^+$.

To a stirred solution of 5,6,7,8-tetrahydro-1,7-naphthyridin-2(1H)-one (TFA salt) (700 mg, 4.66 mmol) in MeOH (10 mL) was added paraformaldehyde (1.4 g, 46.6 mmol) and Pd/C (500 mg). The reaction was stirred under H$_2$ for 16 h. The reaction mixture was filtered through a celite pad, and the filtrate was concentrated under reduced pressure to afford 7-methyl-5,6,7,8-tetrahydro-1,7-naphthyridin-2(1H)-one (600 mg, 78%) as a semi-sold; MS (ESI) m/z 165.1 [M+H]$^+$.

A mixture of POCl$_3$ (4 mL) and 7-methyl-5,6,7,8-tetrahydro-1,7-naphthyridin-2(1H)-one (600 mg, 3.65 mmol) was refluxed for 48 h. The reaction mixture was concentrated under reduced pressure, and the residue was dissolved in water. The pH was adjusted to 8 with sat. NaHCO$_3$, and the mixture was extracted with 10% MeOH in DCM (2×20 mL). The combined organic layers were dried (Na$_2$SO$_4$), filtered and concentrated under reduced pressure to afford 2-chloro-7-methyl-5,6,7,8-tetrahydro-1,7-naphthyridine (250 mg, 37%) as a pale yellow solid; MS (ESI) m/z 183.1 [M+H]$^+$.

In a pressure tube, to a stirred solution of 2-chloro-7-methyl-5,6,7,8-tetrahydro-1,7-naphthyridine (250 mg, 1.37 mmol) in 1,4-dioxane (5 mL), were added benzophenone imine (495 mg, 2.74 mmol) and Cs$_2$CO$_3$ (1.113 g, 3.42 mmol). The mixture was degassed with argon for 10 mins, then Xantphos (79 mg, 0.14 mmol) and Pd$_2$(dba)$_3$ (62 mg, 0.07 mmol) were added to the reaction mixture. The reaction was heated to 100° C. for 16 h. The reaction was cooled to RT, filtered through a celite pad and washed with 10% MeOH/DCM. The filtrate was concentrated under reduced pressure to afford crude N-(7-methyl-5,6,7,8-tetrahydro-1,7-naphthyridin-2-yl)-1,1-diphenylmethanimine (1.0 g) as a semi-solid. MS (ESI) m/z 328.1 [M+H]$^+$.

To a stirred solution of N-(7-methyl-5,6,7,8-tetrahydro-1,7-naphthyridin-2-yl)-1,1-diphenylmethanimine (1.0 g, 3.05 mmol) in MeOH (10 mL), was added NH$_2$OH.HCl (1.059 g, 15.25 mmol). The reaction was stirred at RT for 16 h. The reaction was concentrated under reduced pressure, and the residue was dissolved in water (30 mL) and extracted with EA (1×20 mL). The pH of the aqueous layer was adjusted to 8 using sat. NaHCO$_3$, and the mixture was extracted with 10% MeOH/DCM (3×20 mL). The combined organic layers were dried (Na$_2$SO$_4$), filtered and concentrated under reduced pressure to obtain 7-methyl-5,6,7,8-tetrahydro-1,7-naphthyridin-2-amine (120 mg, 79%) as an off white solid. $^1$H NMR (300 MHz, DMSO-d$_6$) δ 7.09 (d, J=8.4 Hz, 1H), 6.24 (d, J=8.1 Hz, 1H), 5.63 (br s, 2H), 3.25 (s, 2H), 2.65-2.50 (m, 4H), 2.31 (s, 3H); MS (ESI) m/z 164.1 [M+H]$^+$.

Intermediate B (120 mg) was prepared according to General Procedure A. To a stirred solution of 7-methyl-5,6,7,8-tetrahydro-1,7-naphthyridin-2-amine (120 mg, 0.74 mmol) in THF (4 mL) was added 1M in THF LiHMDS (2.2 mL, 2.20 mmol) at 0° C. followed by addition of Intermediate B (290 mg, 0.74 mmol). The ice bath was removed, and the reaction was stirred at RT for 1 h. The reaction was quenched with sat. NH$_4$Cl (20 mL) and extracted with EA (2×15 mL). The combined organic layers were dried (Na$_2$SO$_4$), filtered and concentrated under reduced pressure. The resulting residue was purified by reverse phase HPLC (acetonitrile, 10 mM NH$_4$HCO$_3$) to afford Example 24 (22 mg) as an off-white solid. $^1$H NMR (400 MHz, DMSO-d$_6$) δ 10.40 (br s, 1H), 8.92 (s, 1H), 8.03 (t, J=8.0 Hz, 1H), 7.94 (d, J=8.4 Hz, 1H), 7.81 (d, J=8.4 Hz, 1H), 7.61 (d, J=7.6 Hz, 1H), 7.56 (d, J=8.8 Hz, 1H), 5.73-5.63 (m, 1H), 5.60 (br s, 1H), 4.99 (d, J=10.0 Hz, 1H), 4.82 (d, J=17.2 Hz, 1H), 4.72 (d, J=5.6 Hz, 2H), 3.45 (s, 2H), 2.83-2.78 (m, 2H), 2.66-2.59 (m, 2H), 2.36 (s, 3H), 1.46 (s, 6H); MS (ESI) m/z 473.4 [M+H]$^+$.

Example 25

2-Allyl-1-(6-(2-hydroxypropan-2-yl)pyridin-2-yl)-6-((6-methyl-5,6,7,8-tetrahydro-1,6-naphthyridin-3-yl)amino)-1,2-dihydro-3H-pyrazolo[3,4-d]pyrimidin-3-one

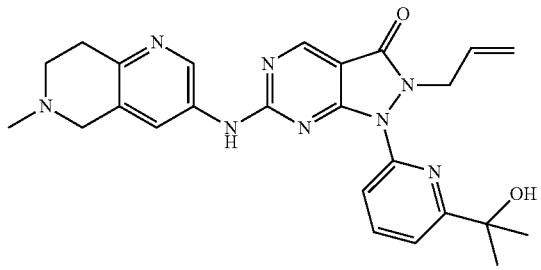 [SMILES: C=CCn1c(=O)c2cnc(Nc3cnc4c(c3)CN(C)CC4)nc2n1-c1cccc(C(C)(C)O)n1]

Example 25 was prepared according to General Procedure A using commercially available 6-methyl-5,6,7,8-tetrahydro-1,6-naphthyridin-3-amine. $^1$H NMR (400 MHz, DMSO-d$_6$) δ 10.33 (br s, 1H), 8.90 (s, 1H), 8.54 (d, J=2.0 Hz, 1H), 8.02-7.96 (m, 2H), 7.73 (d, J=8.4 Hz, 1H), 7.65 (d, J=7.2 Hz, 1H), 5.71-5.61 (m, 1H), 5.31 (s, 1H), 4.99 (d, J=11.6 Hz, 1H), 4.82 (d, J=18.8 Hz, 1H), 4.68 (d, J=5.6 Hz, 2H), 3.51 (s, 2H), 2.87-2.81 (m, 2H), 2.72-2.65 (m, 2H), 2.39 (s, 3H), 1.45 (s, 6H); MS (ESI) m/z 473.2 [M+H]$^+$.

Example 26

2-Allyl-1-(6-(2-hydroxypropan-2-yl)pyridin-2-yl)-6-((6-methyl-5,6,7,8-tetrahydro-1,6-naphthyridin-2-yl)amino)-1,2-dihydro-3H-pyrazolo[3,4-d]pyrimidin-3-one

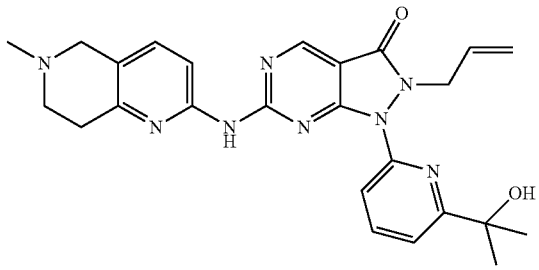 [SMILES: C=CCn1c(=O)c2cnc(Nc3ccc4c(n3)CCN(C)C4)nc2n1-c1cccc(C(C)(C)O)n1]

Crude Intermediate B (170 mg) was prepared according to General Procedure A. To a stirred solution of 6-methyl-5,6,7,8-tetrahydro-1,6-naphthyridin-2-amine (170 mg, 1.04 mmol) in THF (5 mL) was added LiHMDS (1M in THF) (3.2 mL, 3.13 mmol). The reaction was stirred 10 mins and cooled to 0° C. Intermediate B (447 mg, 1.15 mmol) in THF (5 mL) was added. The ice bath was removed, and the reaction was stirred at RT for 1 h. The reaction was quenched with sat. NH$_4$Cl (5 mL) and extracted with EA (2×30 mL). The combined organic layers were washed with brine (20 mL), dried (Na$_2$SO$_4$), filtered and concentrated under reduced pressure. The resulting crude compound was triturated with acetonitrile to afford Example 26 (70 mg) as an off-white solid. $^1$H NMR (400 MHz, DMSO-d$_6$) δ 10.41 (s, 1H), 8.92 (s, 1H), 8.03 (t, J=8.4 Hz, 1H), 7.93 (d, J=8.8 Hz, 1H), 7.81 (d, J=8.4 Hz, 1H), 7.62 (d, J=7.2 Hz, 1H), 7.49 (d, J=8.4 Hz, 1H), 5.72-5.61 (m, 1H), 5.33 (s, 1H), 4.99 (d, J=10.4 Hz, 1H), 4.82 (d, J=17.2 Hz, 1H), 4.72 (d, J=6.4 Hz, 2H), 3.48 (s, 2H), 2.83 (t, J=5.6 Hz, 2H), 2.69 (t, J=5.2 Hz, 2H), 2.36 (s, 3H), 1.46 (s, 6H); MS (ESI) m/z 473.4 [M+H]$^+$.

Example 27

2-Allyl-6-((4,4-difluoro-2-methyl-1,2,3,4-tetrahydroisoquinolin-7-yl)amino)-1-(6-(2-hydroxypropan-2-yl)pyridin-2-yl)-1,2-dihydro-3H-pyrazolo[3,4-d]pyrimidin-3-one

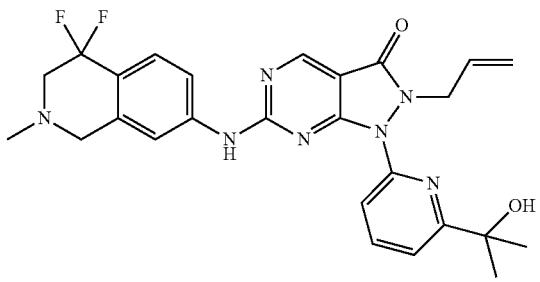 [SMILES: C=CCn1c(=O)c2cnc(Nc3ccc4c(c3)CN(C)CC4(F)F)nc2n1-c1cccc(C(C)(C)O)n1]

To a stirred solution of 2-bromo-5-chlorobenzonitrile (15 g, 69.76 mmol) in DMSO (150 mL) was added ethyl 2-bromo-2,2-difluoroacetate (35.22 g, 174.4 mmol) and copper powder (23.05 g, 362.75 mmol) at RT. The reaction was heated to 65° C. and stirred for 16 h. The reaction was poured into 10% aq. KH$_2$PO$_4$ solution and stirred at RT for 30 mins. The reaction was extracted with EA (2×200 mL). The combined organic layers were dried (Na$_2$SO$_4$), filtered and concentrated under reduced pressure to afford ethyl 2-(4-chloro-2-cyanophenyl)-2,2-difluoroacetate (17 g, crude) as a brown oil. A mixture of conc. H$_2$SO$_4$ (50 mL) and ethyl 2-(4-chloro-2-cyanophenyl)-2,2-difluoroacetate (17 g, 65.63 mmol) were stirred at RT for 20 h. The reaction mixture was poured into ice-water and extracted with EA (2×200 mL). The combined organic layers were washed with water (200 mL) and brine (200 mL), dried (Na$_2$SO$_4$), filtered and concentrated under reduced pressure. The crude mixture was purified by column chromatography (SiO$_2$, EA/pet. ether) to afford 7-chloro-4,4-difluoroisoquinoline-1,3(2H,4H)-dione (2.5 g, 15%) as an off-white solid. MS (ESI) m/z 230.40 [M−H]$^-$.

BF$_3$-Et$_2$O (6.14 g, 43.28 mmol) was added to a stirred solution of NaBH$_4$ (1.23 g, 32.46 mmol) in THF (15 mL) dropwise at 0° C. The ice bath was removed, and the reaction was stirred at RT for 1 h. 7-chloro-4,4-difluoroisoquinoline-1,3(2H,4H)-dione (2.5 g, 10.82 mmol) in THF (10 mL) was added, and the reaction was refluxed for 2 h. The pH was adjusted 8 using sat. NaHCO$_3$, and the mixture was then concentrated under reduced pressure. The mixture was dissolved in EtOH (30 mL). 6N HCl (1 mL) was added, and the mixture was refluxed for 1 h. The mixture was concentrated under reduced pressure, and the residue was dissolved in water (20 mL). The pH was adjusted to 8 using sat. NaHCO$_3$ solution and extracted with EA (2×20 mL). The organic layers were dried (Na$_2$SO$_4$), filtered and concentrated under reduced pressure to afford 7-chloro-4,4-difluoro-1,2,3,4-tetrahydroisoquinoline (2.2 g, 98%) as a colourless oil; MS (ESI) m/z 204.3 [M+H]$^+$.

To a stirred solution of 7-chloro-4,4-difluoro-1,2,3,4-tetrahydroisoquinoline (2.2 g, 10.83 mmol) in formic acid (30 mL) was added paraformaldehyde (3.24 g, 108.3 mmol), and the mixture was heated at 100° C. for 16 h. The reaction was concentrated under reduced pressure, and the residue was dissolved in water (15 mL). The pH was adjusted to 8 using sat. NaHCO$_3$, and the mixture was extracted with EA (2×10 mL). The organic layers were dried (Na$_2$SO$_4$), filtered and concentrated under reduced pressure. The crude mixture was purified by column chromatography (SiO$_2$, EA/pet. ether) to afford 7-chloro-4,4-difluoro-2-methyl-1,2,3,4-tetrahydroisoquinoline (1.2 g, 51%) as an off-white solid; MS (ESI) m/z 218.3 [M+H]$^+$.

Intermediate B (2.2 g) was prepared according to General Procedure A. To a stirred solution of Intermediate B (2.2 g, 5.65 mmol) in isopropanol (25 mL) was added aq. NH$_3$ (10 mL) drop-wise at 0° C. The ice bath was removed, and the reaction was stirred at RT for 30 mins. The mixture was extracted with DCM (2×10 mL), and the organic layers were dried (Na$_2$SO$_4$), filtered and concentrated under reduced pressure. The crude compound was triturated with diethyl ether to afford 2-allyl-6-amino-1-(6-(2-hydroxypropan-2-yl)pyridin-2-yl)-1,2-dihydro-3H-pyrazolo[3,4-d] pyrimidin-3-one (530 mg, 29%) as an off-white solid; MS (ESI) m/z 327.5 [M+H]$^+$.

To a stirred solution of 2-allyl-6-amino-1-(6-(2-hydroxypropan-2-yl)pyridin-2-yl)-1,2-dihydro-3H-pyrazolo[3,4-d]pyrimidin-3-one (1.0 g, 3.07 mmol) and 7-chloro-4,4-difluoro-2-methyl-1,2,3,4-tetrahydroisoquinoline (0.665 g, 3.07 mmol) in 1,4-dioxane (15 mL) was added NaOtBu (0.588 g, 6.13 mmol). The resulting solution was degassed with argon for 10 mins. Brettphos (65 mg, 0.122 mmol) and G3 precatalyst (27 mg, 0.03 mmol) were added, and the mixture was heated at 100° C. for 2 h in microwave. The reaction mixture was filtered through a celite pad and washed 10% MeOH in DCM. The filtrate was concentrated under reduced pressure. The crude mixture was purified by column chromatography (SiO$_2$, EA/pet. ether). The compound was further purified by reverse phase HPLC (water/acetonitrile, 0.1% formic acid) to afford Example 27 (35 mg) as a white solid. $^1$H NMR (400 MHz, DMSO-d$_6$) δ 8.76 (br s, 1H), 7.83 (d, J=7.2 Hz, 1H), 7.76 (t, J=7.6 Hz, 1H), 7.65 (d, J=8.0 Hz, 1H), 7.43-7.38 (m, 3H), 6.07-5.94 (m, 1H), 5.32 (br s, 1H), 5.19 (d, J=17.6 Hz, 1H), 5.12 (d, J=9.6 Hz, 1H), 4.73 (d, J=4.4 Hz, 2H), 3.59 (s, 2H), 3.07 (t, J=12.4 Hz, 2H), 2.41 (s, 3H), 1.68 (s, 1H), 1.43 (s, 6H); MS (ESI) m/z 508.13 [M+H]$^+$.

Example 28

2-Allyl-6-((4,4-difluoro-1,2,3,4-tetrahydroisoquinolin-7-yl)amino)-1-(6-(2-hydroxypropan-2-yl)pyridin-2-yl)-1,2-dihydro-3H-pyrazolo[3,4-d]pyrimidin-3-one hydrogen chloride

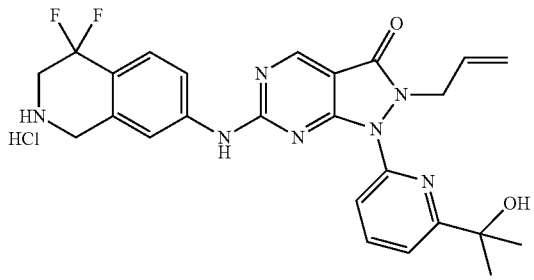 [SMILES: Cl ; C=CCn1c(=O)c2cnc(Nc3ccc4c(c3)CNCC4(F)F)nc2n1-c1cccc(C(C)(C)O)n1]

To a stirred solution of 7-chloro-4,4-difluoro-1,2,3,4-tetrahydroisoquinoline (3.8 g, 18.71 mmol) in DCM (40 mL) was added DIPEA (9.78 mL, 56.13 mmol) and di-tert-butyl dicarbonate (6.24 mL, 28.06 mmol) at 0° C. The ice bath was removed, and reaction was stirred at RT for 16 h. The reaction was diluted with DCM (150 mL) and washed with water (200 mL) and brine (100 mL). The organic layers were dried (Na$_2$SO$_4$), filtered and concentrated under reduced pressure. The crude mixture was purified by column chromatography (SiO$_2$, 20% EA/pet. ether) to afford tert-butyl 7-chloro-4,4-difluoro-3,4-dihydroisoquinoline-2(1H)-carboxylate (3.5 g, 61%) as an off-white solid. $^1$H NMR (400 MHz, CDCl$_3$) δ 7.63 (d, J=8.4 Hz, 1H), 7.33 (d, J=8.4 Hz, 1H), 7.21 (s, 1H), 4.64 (s, 2H), 4.0 (t, J=11.2 Hz, 2H), 1.49 (s, 9H).

To a stirred solution of 2-allyl-6-amino-1-(6-(2-hydroxypropan-2-yl)pyridin-2-yl)-1,2-dihydro-3H-pyrazolo[3,4-d]pyrimidin-3-one (1.0 g, 3.07 mmol) and tert-butyl 7-chloro-4,4-difluoro-3,4-dihydroisoquinoline-2(1H)-carboxylate (0.929 g, 3.07 mmol) in 1,4-dioxane (15 mL) was added NaOtBu (0.588 g, 6.13 mmol). The resulting solution was degassed with argon. Brettphos (65 mg, 0.122 mmol) and G$_3$ precatalyst (27 mg, 0.03 mmol) were added. The resulting mixture was heated in the microwave at 100° C. for 2 h. The reaction was filtered through a celite pad and washed with 10% MeOH in DCM. The filtrate was concentrated under reduced pressure. The crude compound was purified by reverse phase HPLC (acetonitrile, 10 mM NH$_4$HCO$_3$) to afford tert-butyl 7-((2-allyl-1-(6-(2-hydroxypropan-2-yl)pyridin-2-yl)-3-oxo-2,3-dihydro-1H-pyrazolo[3,4-d]pyrimidin-6-yl)amino)-4,4-difluoro-3,4-dihydroisoquinoline-2(1H)-carboxylate (100 mg) as a white solid; MS (ESI) m/z 594.2 [M+H]$^+$.

To a stirred solution of tert-butyl 7-((2-allyl-1-(6-(2-hydroxypropan-2-yl)pyridin-2-yl)-3-oxo-2,3-dihydro-1H-pyrazolo[3,4-d]pyrimidin-6-yl)amino)-4,4-difluoro-3,4-dihydroisoquinoline-2(1H)-carboxylate (100 mg, 0.17 mmol) in Et$_2$O (4 mL) was added 2M HCl in Et$_2$O (3 mL) dropwise at 0° C. The ice bath was removed, and the reaction was stirred at RT for 2 h. The reaction was concentrated under reduced pressure, and the residue was triturated with pentane and diethyl ether to afford Example 28 (73 mg, mmol, 82%) as a pale yellow solid. $^1$H NMR (400 MHz, DMSO-d$_6$) δ 10.68 (br s, 1H), 10.13 (br s, 2H), 8.98 (s, 1H), 8.08 (t, J=8.4 Hz, 1H), 7.96 (br s, 1H), 7.83-7.70 (m, 3H), 7.65 (d, J=8.0 Hz, 1H), 5.71-5.64 (m, 1H), 5.01 (d, J=9.6 Hz, 1H), 4.82 (d, J=17.2 Hz, 1H), 4.70 (d, J=6.0 Hz, 2H), 4.42 (s, 2H), 4.04 (t, J=11.6 Hz, 2H), 1.46 (s, 6H); MS (ESI) m/z 494.2 [M+H]$^+$.

Examples 29 and 30

(R)-2-Allyl-1-(6-(2-hydroxypropan-2-yl)pyridin-2-yl)-6-((1,4,4-trimethyl-1,2,3,4-tetrahydroisoquinolin-7-yl)amino)-1,2-dihydro-3H-pyrazolo[3,4-d]pyrimidin-3-one hydrogen chloride (29)

(S)-2-Allyl-1-(6-(2-hydroxypropan-2-yl)pyridin-2-yl)-6-((1,4,4-trimethyl-1,2,3,4-tetrahydroisoquinolin-7-yl)amino)-1,2-dihydro-3H-pyrazolo[3,4-d]pyrimidin-3-one hydrogen chloride (30)

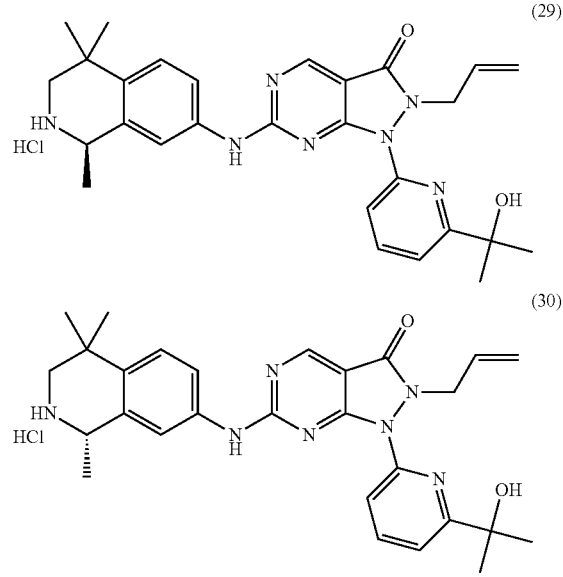

To a stirred RT solution of 2-methyl-2-phenylpropan-1-amine (3 g, 20.10 mmol) in pyridine (1.78 mL, 22.11 mmol) was added Ac$_2$O (2.28 mL, 24.12 mmol). The reaction was heated to 90° C. for 2 h. After completion, the reaction was poured into ice and conc. HCl (20 mL) was added. The aqueous layer was extracted with EA (2×20 mL). The combined extracts were washed with sat. NaHCO$_3$ (30 mL), dried (Na$_2$SO$_4$) and evaporated under reduced pressure. The crude mixture was purified by column chromatography (SiO$_2$, 20% EA/hexanes) to afford N-(2-methyl-2-phenylpropyl)acetamide (2.7 g, 70%); MS (ESI) m/z 192.4 [M+H]$^+$.

N-(2-methyl-2-phenylpropyl)acetamide (20 g, 104.5 mmol) in PPA (200 mL, 10 vol) was heated to 200° C. for 3 h. After completion, the mixture was poured onto ice and basified with aq. NH$_3$. The mixture was extracted with EA (3×100 mL). The combined extracts were washed with brine (200 mL), dried (Na$_2$SO$_4$) and evaporated under reduced pressure to afford 1,4,4-trimethyl-3,4-dihydroisoquinoline (15 g, 83%); MS (ESI) m/z 174.2 [M+H]$^+$.

To a stirred solution of 1,4,4-trimethyl-3,4-dihydroisoquinoline (8 g, 46.17 mmol) in MeOH (10 mL) was added NaBH$_4$ (2.07 g, 55.40 mmol) at 0° C. The reaction was stirred at RT for 2 h. Upon completion, the reaction was concentrated, and the mixture was partitioned between sat. NH$_4$Cl and EA. The organic layer was separated, dried (Na$_2$SO$_4$) and evaporated under reduced pressure. The crude mixture was purified by column chromatography (SiO$_2$, 3% MeOH/DCM) to afford compound 1,4,4-trimethyl-1,2,3,4-tetrahydroisoquinoline (4.8 g, 59%); MS (ESI) m/z 176.2 [M+H]$^+$.

To a stirred solution of 1,4,4-trimethyl-1,2,3,4-tetrahydroisoquinoline (400 mg, 2.71 mmol) in H$_2$SO$_4$ (4 ml) was added HNO$_3$ (0.1 mL, 2.44 mmol) dropwise at −10° C. The reaction was stirred at −10° C. for 2 h. Upon completion, the reaction was poured on to crushed ice, basified with sat. NaHCO$_3$ solution (200 mL) and extracted with EA (2×300 mL). The organic layer was washed with brine (300 mL) dried (Na$_2$SO$_4$) and evaporated under reduced pressure to afford 1,4,4-trimethyl-7-nitro-1,2,3,4-tetrahydroisoquinoline (420 mg) as an oil; MS (ESI) m/z 221.1 [M+H]$^+$.

To a stirred RT solution of crude 1,4,4-trimethyl-7-nitro-1,2,3,4-tetrahydroisoquinoline (420 mg, 1.91 mmol) in DCM (6 mL) were added TEA (0.4 mL, 2.86 mmol) and di-tert-butyl dicarbonate (0.52 mL, 2.29 mmol). The reaction was stirred at RT for 1 h. Upon completion, the reaction was diluted with DCM (20 mL) and washed with water (20 mL). The organic layer was dried (Na$_2$SO$_4$) and evaporated under reduced pressure. The crude mixture was purified by column chromatography (SiO$_2$, 3% MeOH/DCM) to afford tert-butyl 1,4,4-trimethyl-7-nitro-3,4-dihydroisoquinoline-2 (1H)-carboxylate (430 mg, 70%) as a brown oil; MS (ESI) m/z 265.2 [M-tBu+H]$^+$.

To a stirred solution of tert-butyl 1,4,4-trimethyl-7-nitro-3,4-dihydroisoquinoline-2(1H)-carboxylate (4 g, 12.48 mmol) in MeOH (40 ml) was added Pd/C (400 mg, 10% w/w), and the reaction mixture was stirred under H$_2$ at RT for 16 h. After completion by TLC, the reaction was filtered through a pad of celite, and the filtrate was evaporated. The crude mixture was purified by column chromatography (SiO$_2$, 30% EA/hex) to afford tert-butyl 7-amino-1,4,4-trimethyl-3,4-dihydroisoquinoline-2(1H)-carboxylate (2.1 g, 58%) as an oil; MS (ESI) m/z 291.5 [M+H]$^+$.

Crude Intermediate B (800 mg) was prepared according to General Procedure A. In a microwave vial, to a stirred solution of Intermediate B (800 mg, 2.06 mmol) in dioxane (15 mL) were added tert-butyl 7-amino-1,4,4-trimethyl-3,4-dihydroisoquinoline-2(1H)-carboxylate (596 mg, 2.06 mmol) and DIPEA (1.07 mL, 6.165 mmol) at RT. The reaction was stirred at 90° C. for 2 h in the microwave. Upon completion, the reaction was concentrated under reduced pressure. The crude mixture was purified by column chromatography (SiO$_2$, 50% EA/Hex) to afford 600 mg which was further purified by reverse phase HPLC (acetonitrile, 10 mM NH$_4$HCO$_3$) to afford racemic tert-butyl 7-((2-allyl-1-(6-(2-hydroxypropan-2-yl)pyridin-2-yl)-3-oxo-2,3-dihydro-1H-pyrazolo[3,4-d]pyrimidin-6-yl)amino)-1,4,4-trimethyl-3,4-dihydroisoquinoline-2(1H)-carboxylate (250 mg) as an off white solid. The enantiomers were separated by chiral SFC chromatography (Chiralpak AD-H (30×250 mm), CO$_2$, MeOH) to afford peak 1 (tert-butyl (R)-7-((2-allyl-1-(6-(2-hydroxypropan-2-yl)pyridin-2-yl)-3-oxo-2,3-dihydro-1H-pyrazolo[3,4-d]pyrimidin-6-yl)amino)-1,4,4-trimethyl-3,4-dihydroisoquinoline-2(1H)-carboxylate, 85 mg), MS (ESI) m/z 600.7 [M+H]+; and peak 2 (tert-butyl (S)-7-((2-allyl-1-(6-(2-hydroxypropan-2-yl)pyridin-2-yl)-3-oxo-2,3-dihydro-1H-pyrazolo[3,4-d]pyrimidin-6-yl)amino)-1,4,4-trimethyl-3,4-dihydroisoquinoline-2(1H)-carboxylate, 105 mg); MS (ESI) m/z 600.7 [M+H]$^+$. Please note the stereochemistry for peaks 1 and 2 is arbitrarily defined.

To a stirred solution of tert-butyl (R)-7-((2-allyl-1-(6-(2-hydroxypropan-2-yl)pyridin-2-yl)-3-oxo-2,3-dihydro-1H-pyrazolo[3,4-d]pyrimidin-6-yl)amino)-1,4,4-trimethyl-3,4-dihydro-isoquinoline-2(1H)-carboxylate (peak1) (85 mg, 0.141 mmol) in dioxane (0.9 mL) was added 4 M HCl in dioxane (0.9 mL) at 0° C. The ice bath was removed, and the reaction was stirred at RT for 2 h. Upon completion, the solvent was evaporated under reduced pressure. The crude residue was triturated with n-pentane/diethyl ether to afford Example 29 (50 mg, 66%) as an off white solid. $^1$H NMR (400 MHz, DMSO-d$_6$) δ 10.29 (br s, 1H), 9.42 (br s, 1H), 8.94 (br s, 1H), 8.90 (s, 1H), 8.03 (t, J=7.6 Hz, 1H), 7.74 (d, J=8 Hz, 1H), 7.65-7.61 (m, 3H), 7.44 (d, J=8.8 Hz, 1H), 5.70-5.63 (m, 1H), 4.99 (d, J=10.4 Hz, 1H), 4.82 (d, J=17.2 Hz, 1H), 4.66 (d, J=4.8 Hz, 2H), 4.53-4.52 (m, 1H), 3.30-3.17 (m, 2H), 1.53 (d, J=6.8 Hz, 3H), 1.46 (s, 6H), 1.34 (d, J=14.8 Hz, 6H); MS (ESI) m/z 500.6 [M+H]$^+$.

To a stirred solution of tert-butyl (S)-7-((2-allyl-1-(6-(2-hydroxypropan-2-yl)pyridin-2-yl)-3-oxo-2,3-dihydro-1H-pyrazolo[3,4-d]pyrimidin-6-yl)amino)-1,4,4-trimethyl-3,4-dihydroisoquinoline-2(1H)-carboxylate (peak 2) (105 mg, 0.175 mmol) in dioxane (1 mL) was added 4 M HCl in dioxane (1 mL) at 0° C. The ice bath was removed, and the reaction was stirred RT for 2 h. After completion, the solvent was evaporated under reduced pressure. The crude residue was triturated with n-pentane/diethyl ether to afford Example 30 (61 mg, 65%) as an off white solid. $^1$H NMR (400 MHz, DMSO-d$_6$) δ 10.29 (br s, 1H), 9.56 (br s, 1H), 9.03 (br s, 1H), 8.90 (s, 1H), 8.03 (t, J=7.6 Hz, 1H), 7.74 (d, J=8 Hz, 1H), 7.65-7.61 (m, 3H), 7.44 (d, J=8.8 Hz, 1H), 5.70-5.63 (m, 1H), 4.99 (d, J=10.4 Hz, 1H), 4.82 (d, J=17.2 Hz, 1H), 4.66 (d, J=4.8 Hz, 2H), 4.53-4.52 (m, 1H), 3.30-3.17 (m, 2H), 1.53 (d, J=6.8 Hz, 3H), 1.46 (s, 6H), 1.34 (d, J=14.8 Hz, 6H); MS (ESI) m/z 500.6 [M+H]$^+$. The stereochemistry for Example 29 and 30 is arbitrarily defined.

Procedure A

Wee1 Binding Assay

Wee 1 kinase was determined by using Flurorescence Resonance Energy Transfer (FRET) assay. In 384-well plates, Wee1 kinase (2 nM final concentration) was mixed with AlexaFluor labeled tracer 178 (50 nM final concentration, K$_d$=24 nM), Eu-anti-GST antibody (2 nM final concentration) and then inhibitor (0.003 to 10 micromolar) in a final volume of 16 μl kinase buffer (50 mM HEPES pH 7.5, 0.01% BRIJ-35, 10 mM MgCl2, 1 mM EGTA). The plate was shaken for 30 seconds, incubated for 60 min at RT, and recorded on fluorescence plate reader. The results are shown in Table 1.

Procedure B

SW480 Cellular Proliferation Assay

SW480 [ATCC (CRL-228™)] cells were grown and maintained in 1:4 RPMI-1640 medium with 10% FBS (heat inactivated) and 1% penicillin-streptomycin. Cells were treated with compounds diluted in DMSO and a 10 point 3-fold serial dilutions. Plates were placed in 37° C., 5% $CO_2$ for to incubate for 4 days. Before they were developed by adding 100 μL of CellTiter-Glo reagent (Promega) to the assay plate, plates were shaken briefly for 2 mins and allowed to incubate at RT for 60 mins. The bottom of the plates was pasted with white back seal and luminescence was recorded with Enspire or Envision. The results are shown in Table 1.

Procedure C

H23 Cellular Proliferation Assay

H23 [ATCC (CRL-5800™)] cells were grown and maintained in RPMI-1640 medium with 10% FBS and 1% penicillin-streptomycin. Cells were treated with compounds diluted in DMSO and a 9 point 5-fold serial dilutions. Plates were placed in 37° C., 5% $CO_2$ to incubate for 4 days. Before they were developed by adding 100 μL of CellTiter-Glo reagent (Promega) to the assay plate, plates were shaken briefly for 2 mins and allowed to incubate at RT for 10 mins. The plates are read with a M5e plate reader according to CellTiter-Glo protocol. The GraphPad Prism software was used to get $IC_{50}$ values. The results are shown in Table 1 at RT for 60 mins. The bottom of the plates was pasted with white back seal and luminescence was recorded with Enspire or Envision. The results are shown in Table 1.

TABLE 1

| Wee1 Enzymatic and cellular data | | | |
|---|---|---|---|
| Example # | Wee1 Enzymatic $IC_{50}$ (nM) | SW480 $IC_{50}$ (nM) | H23 $IC_{50}$ (nM) |
| AZD1775 | A | B | B |
| 1 | A | B | A |
| 2 | A | C | A |
| 3 | A | — | — |
| 4 | A | — | — |
| 5 | A | B | A |
| 6 | A | B | B |
| 7 | A | — | B |
| 8 | A | B | C |
| 9 | A | B | — |
| 10 | A | — | — |
| 11 | A | — | A |
| 12 | A | C | A |
| 13 | A | C | B |
| 14 | — | — | B |
| 15 | A | C | B |
| 16 | A | C | A |
| 17 | — | — | B |
| 18 | A | — | B |
| 19 | A | C | C |
| 20 | A | B | B |
| 21 | A | — | B |
| 22 | A | C | B |
| 23 | A | — | B |
| 24 | B | — | — |
| 25 | A | — | — |
| 26 | B | — | — |
| 27 | — | — | C |
| 28 | A | — | B |
| 29 | A | — | B |
| 30 | A | — | A |

For Wee1 enzymatic $IC_{50}$: A = a single $IC_{50}$ ≤10 nM; B = a single $IC_{50}$ >10 nM and <100 nM; C = a single $IC_{50}$ ≥100 nM. For SW480 $IC_{50}$: A = a single $IC_{50}$ ≤10 nM; B = a single $IC_{50}$ >100 nM and <1000 nM; C = a single $IC_{50}$ ≥1000 nM. For H23 $IC_{50}$: A = a single $IC_{50}$ ≤100 nM; B = a single $IC_{50}$ >100 nM and <1000 nM; C = a single $IC_{50}$ ≥1000 nM.

Furthermore, although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

What is claimed is:

1. A compound of Formula (I), or a pharmaceutically acceptable salt thereof, having the structure:

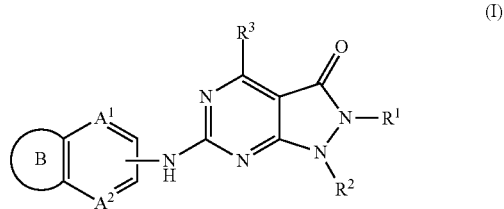

wherein:

$R^1$ is selected from the group consisting of an optionally substituted $C_{1-4}$ alkyl, an optionally substituted $C_{2-4}$ alkenyl, an optionally substituted $C_{2-4}$ alkynyl, an optionally substituted $C_{3-6}$ cycloalkyl and an optionally substituted $C_{3-6}$ cycloalkyl($C_{1-4}$ alkyl), wherein when substituted, the $C_{1-4}$ alkyl, the $C_{2-4}$ alkenyl and the $C_{2-4}$ alkynyl are independently substituted with one or more substituents selected from the group consisting of halogen, $C_{1-4}$ alkoxy, $C_{1-4}$ haloalkyl, $C_{1-4}$ haloalkoxy, cyano, amino, mono-$C_{1-4}$ alkyl amine and di-$C_{1-4}$ alkyl amine, and wherein the ring(s) of the $C_{3-6}$ cycloalkyl and the $C_{3-6}$ cycloalkyl($C_{1-4}$ alkyl) are independently substituted with one or more substituents selected from the group consisting of halogen, $C_{1-4}$ alkyl, $C_{1-4}$ alkoxy, $C_{1-4}$ haloalkyl, $C_{1-4}$ haloalkoxy, cyano, amino, mono-$C_{1-4}$ alkyl amine and di-$C_{1-4}$ alkyl amine;

$R^2$ is an optionally substituted aryl or an optionally substituted heteroaryl, wherein when the aryl or the heteroaryl are substituted, the aryl and the heteroaryl are independently substituted with one or more substituents selected from the group consisting of an unsubstituted $C_{1-4}$ alkyl and

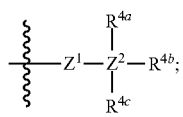

$R^3$ is hydrogen or an unsubstituted $C_{1-4}$ alkyl;

$A^1$ is $CR^{6A}$ or N;

$A^2$ is $CR^{6B}$ or N;

$Z^1$ is a single bond, —C(=O)— or an optionally substituted $C_{1-6}$ alkylene group, wherein one or two more methylene groups constituting the optionally substituted $C_{1-6}$ alkylene group are independently optionally replaced by an oxygen atom or carbonyl group, and wherein when the $C_{1-6}$ alkylene group is substituted, one or more methylene group are independently substituted with an unsubstituted $C_{1-6}$ alkyl group;

$Z^2$ is N or C, and when $Z^2$ is N, then $R^{4c}$ is absent;

$R^{4a}$ and $R^{4b}$ are independently selected from the group consisting of hydrogen, halogen, cyano, hydroxy, an unsubstituted $C_{1-6}$ alkyl, an unsubstituted hydroxy($C_{1-6}$ alkyl), an unsubstituted alkoxy($C_{1-6}$ alkyl), an unsubstituted $C_{2-7}$ acyl, an unsubstituted —C-carboxy having 2-7 carbons, an unsubstituted —C-amido and an unsubstituted $C_{1-7}$ alkylsulfonyl; or $R^{4a}$ and $R^{4b}$ together form an optionally substituted $C_{1-6}$ alkylene, wherein one or two more methylene groups constituting the $C_{1-6}$ alkylene group are independently optionally replaced by an oxygen atom, a sulfur atom, a sulfinyl group, a sulfonyl group, a carbonyl group or —(NR$^5$)—, and wherein when the $C_{1-6}$ alkylene group is substituted, one or more methylene group are independently substituted with a substituent selected from the group consisting of halogen and an unsubstituted $C_{1-6}$ alkyl; or $R^{4a}$ and $R^{4b}$ together with $Z^2$ form an unsubstituted monocyclic $C_{3-6}$ cycloalkyl and an unsubstituted 4-, 5-, or 6-membered heterocyclyl;

$R^{4c}$ is selected from the group consisting of halogen, hydroxy, an unsubstituted $C_{1-6}$ alkyl and an unsubstituted hydroxy($C_{1-6}$ alkyl);

$R^5$ is hydrogen, an unsubstituted $C_{1-6}$ alkyl or an unsubstituted $C_{1-6}$ haloalkyl;

$R^{6A}$ and $R^{6B}$ are independently hydrogen, halogen or an unsubstituted $C_{1-4}$ alkyl; and Ring B is an optionally substituted monocyclic $C_{5-7}$ cycloalkyl, an optionally substituted 5-7 membered monocyclic heterocyclyl or an optionally substituted 7-10 membered bicyclic heterocyclyl, wherein when Ring B is substituted, Ring B is substituted with one or more substituents selected from the group consisting of halogen, an optionally substituted $C_{1-6}$ alkyl, an optionally substituted $C_{1-6}$ haloalkyl, an optionally substituted $C_{3-6}$ cycloalkyl, an optionally substituted aryl, an optionally substituted heteroaryl, an optionally substituted heterocyclyl, an optionally substituted aryl($C_{1-6}$ alkyl), an optionally substituted heteroaryl($C_{1-6}$ alkyl), an optionally substituted heterocyclyl($C_{1-6}$ alkyl), an optionally substituted acyl, an optionally substituted -hydroxy($C_{1-6}$ alkyl), an optionally substituted —C-amido, an optionally substituted —C-amido($C_{1-6}$ alkyl), an optionally substituted —N-amido, an optionally substituted —N-amido($C_{1-6}$ alkyl), an optionally substituted mono-substituted amine, an optionally substituted di-substituted amine, an optionally substituted mono-substituted amine($C_{1-6}$ alkyl), an optionally substituted di-substituted amine($C_{1-6}$ alkyl) and an optionally substituted sulfonyl.

2. The compound of claim 1, wherein $R^1$ is an optionally substituted $C_{2-4}$ alkenyl.

3. The compound of claim 1, wherein $R^1$ is an optionally substituted $C_{1-4}$ alkyl, an optionally substituted $C_{2-4}$ alkynyl, an optionally substituted $C_{3-6}$ cycloalkyl or an optionally substituted $C_{3-6}$ cycloalkyl($C_{1-4}$ alkyl).

4. The compound of claim 1, wherein $R^2$ is an optionally substituted heteroaryl.

5. The compound of claim 4, wherein $R^2$ is substituted with

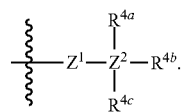

6. The compound of claim 5, wherein $Z^1$ is a single bond and $Z^2$ is C.

7. The compound of claim 6, wherein $R^{4a}$ and $R^{4b}$ are independently selected from the group consisting of hydrogen, halogen, cyano, hydroxy, an unsubstituted $C_{1-6}$ alkyl, an unsubstituted hydroxy($C_{1-6}$ alkyl), an unsubstituted alkoxy($C_{1-6}$ alkyl), an unsubstituted $C_{2-7}$ acyl, an unsubstituted —C-carboxy having 2-7 carbons, an unsubstituted —C-amido and an unsubstituted $C_{1-7}$ alkylsulfonyl.

8. The compound of claim 7, wherein $R^{4a}$ and $R^{4b}$ are independently hydroxy or an unsubstituted $C_{1-6}$ alkyl.

9. The compound of claim 7, wherein $R^{4c}$ is an unsubstituted $C_{1-6}$ alkyl.

10. The compound of claim 1, wherein $R^3$ is hydrogen.

11. The compound of claim 1, wherein $A^1$ is $CR^{6A}$; and $A^2$ is $CR^{6B}$.

12. The compound of claim 11, wherein $R^{6A}$ is hydrogen; and $R^{6B}$ is hydrogen.

13. The compound claim 1, wherein $A^1$ is N; and $A^2$ is $CR^{6B}$; or $A^1$ is $CR^{6A}$; and $A^2$ is N.

14. The compound of claim 13, wherein $R^{6A}$ is hydrogen; and $R^{6B}$ is hydrogen.

15. The compound claim 1, wherein Ring B is an optionally substituted monocyclic $C_{5-7}$ cycloalkyl.

16. The compound of claim 1, wherein Ring B is an optionally substituted 5-7 membered monocyclic heterocyclyl or an optionally substituted 7-10 membered bicyclic heterocyclyl.

17. The compound of claim 16, wherein Ring B is selected from the group consisting of:

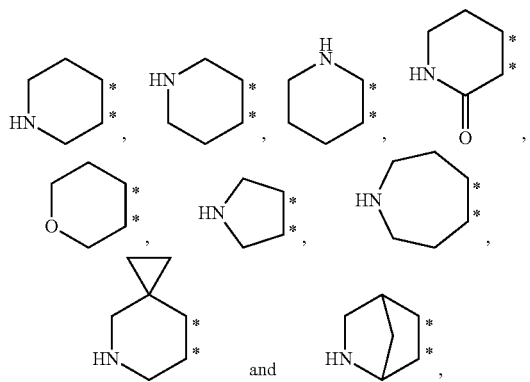

wherein the asterisks indicate the points of attachment to ring
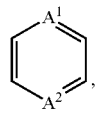
wherein each ring can be optionally substituted at a ring carbon, and wherein each ring can be optionally substituted at a ring nitrogen.
18. The compound of claim 1, wherein the compound is selected from the group consisting of:
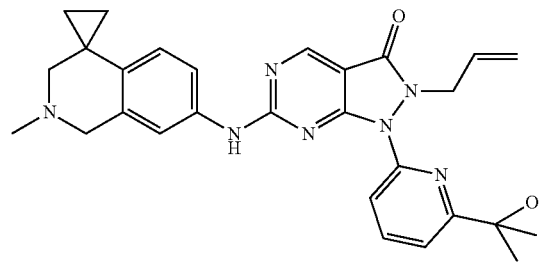
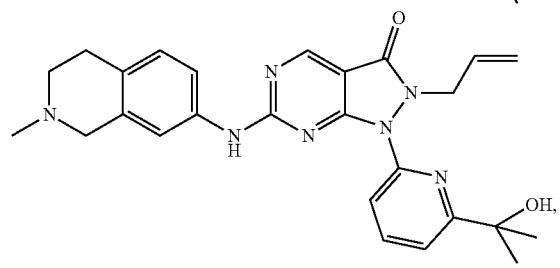
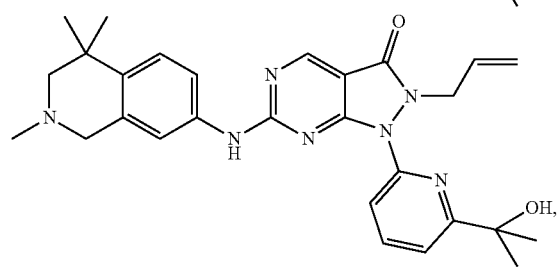
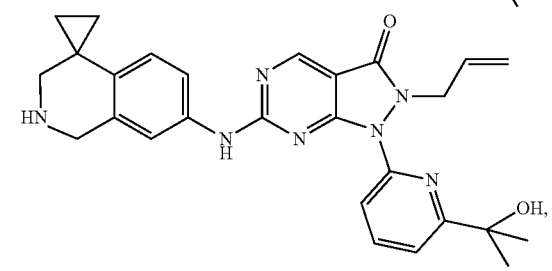
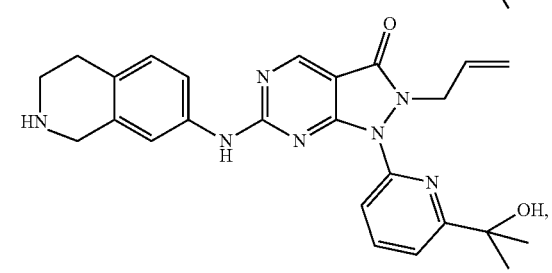
-continued
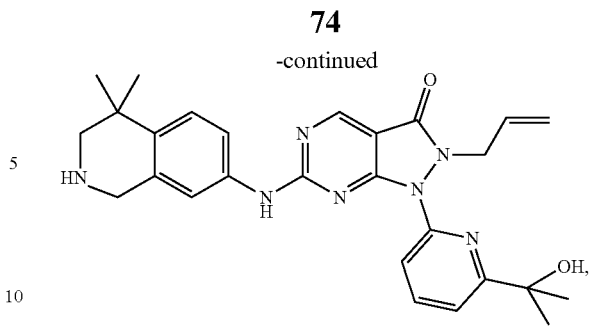
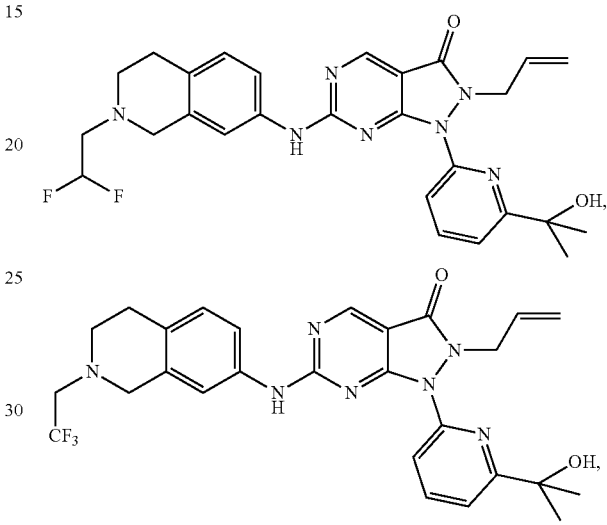
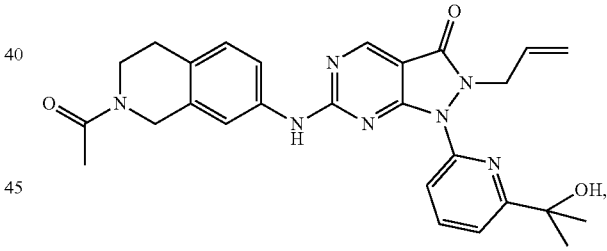
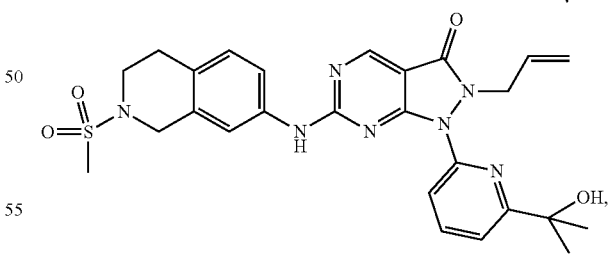
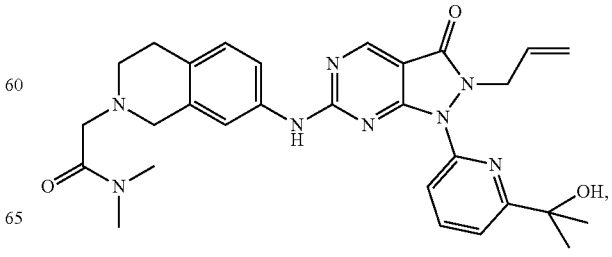

75
-continued
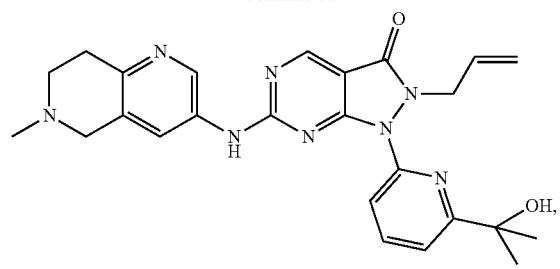
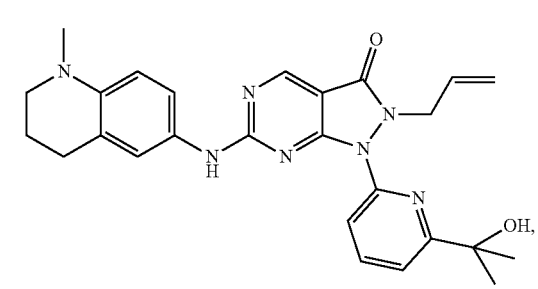
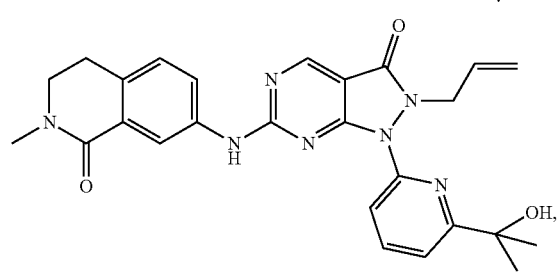
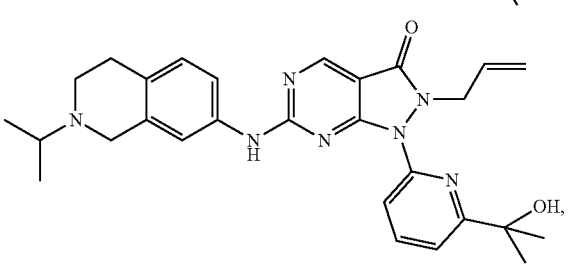
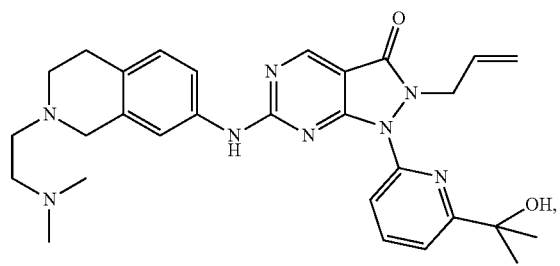
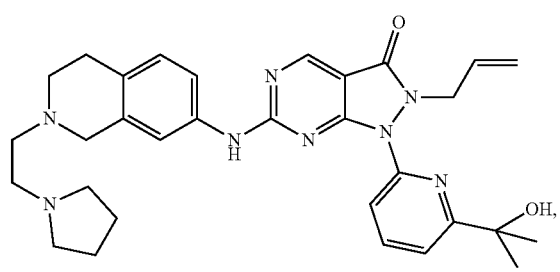
76
-continued
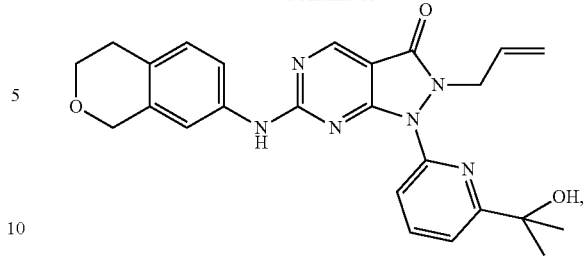
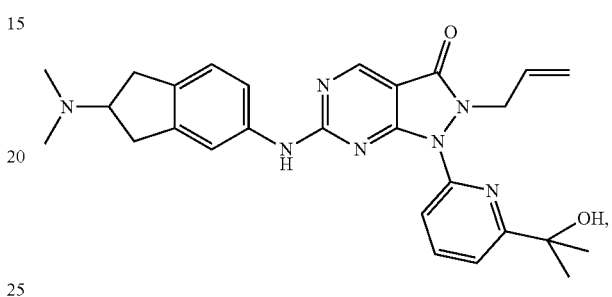
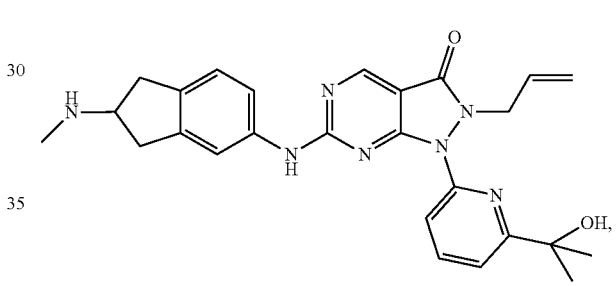
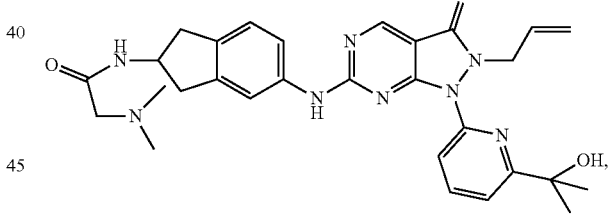
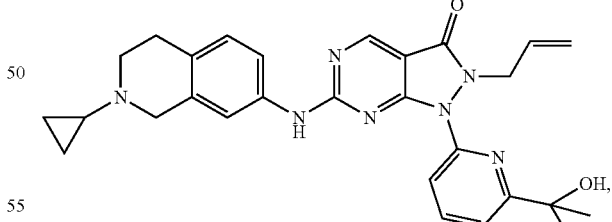
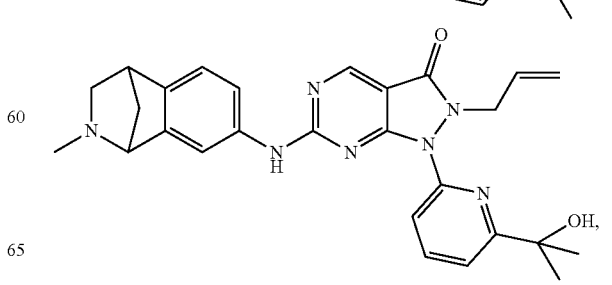

77
-continued
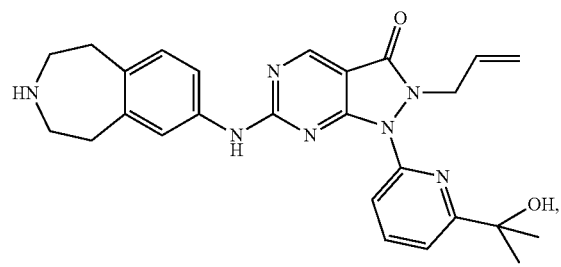
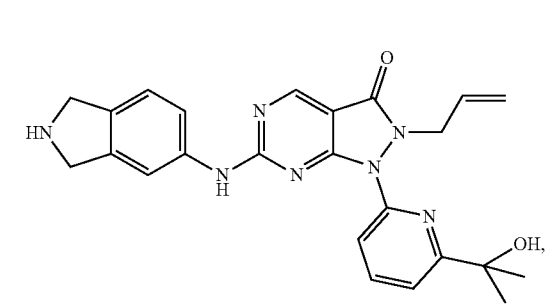
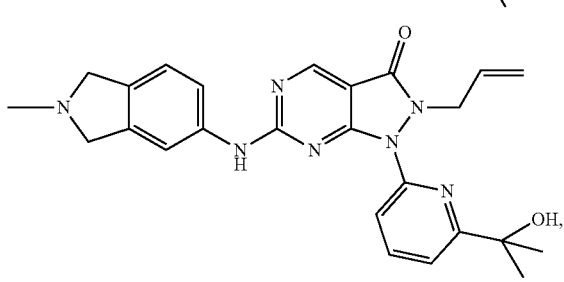
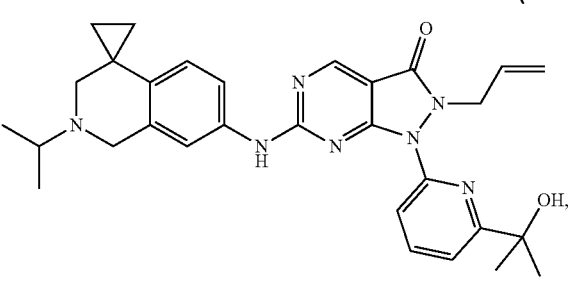
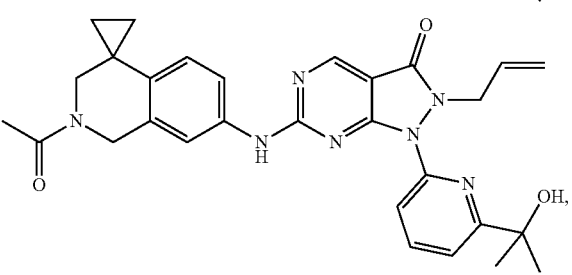
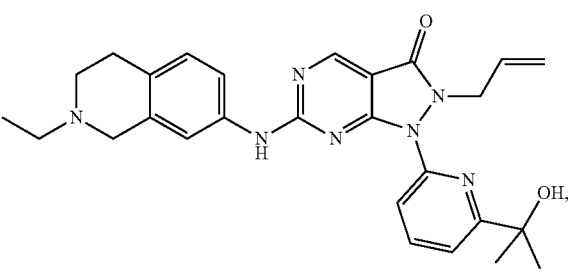
78
-continued
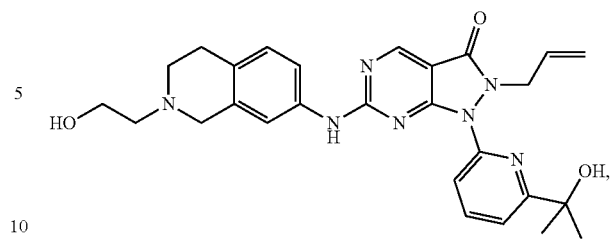
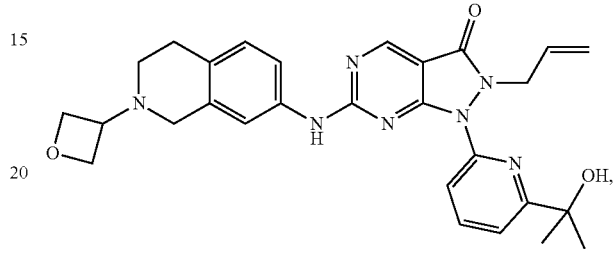
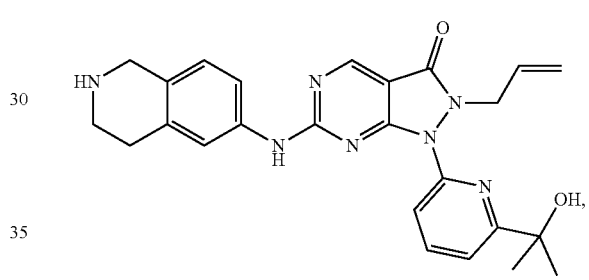
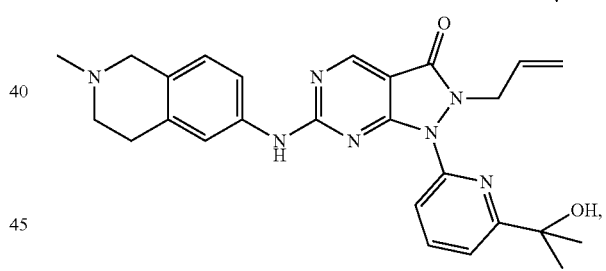
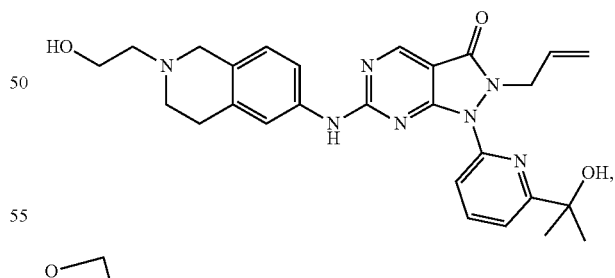
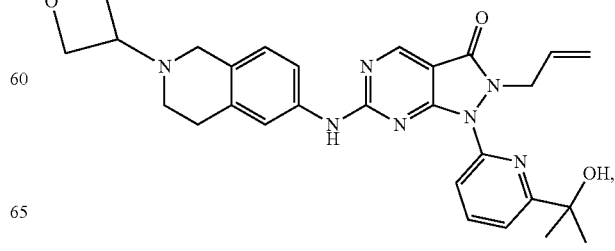

79
-continued
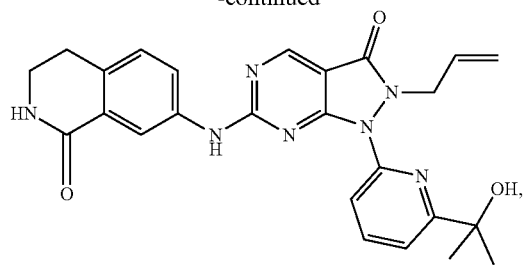
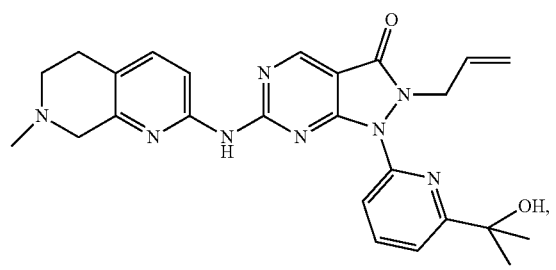
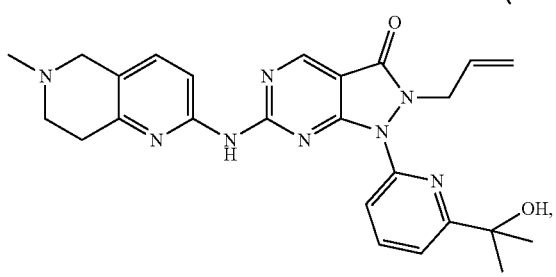
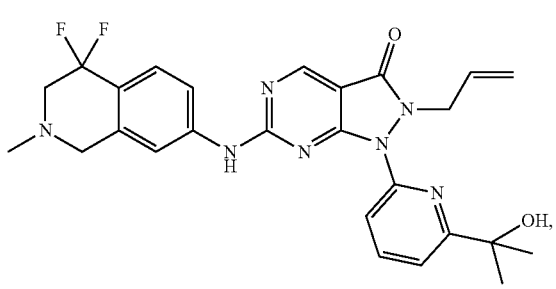
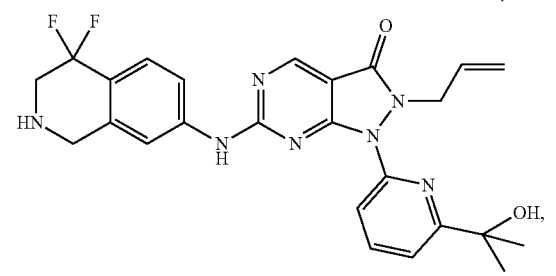
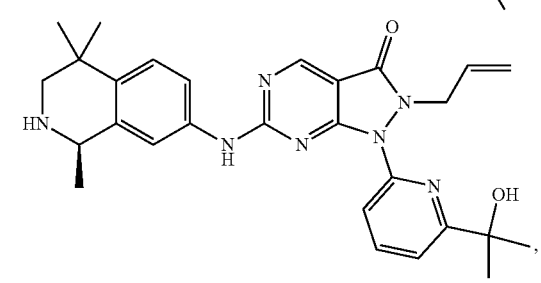
80
-continued
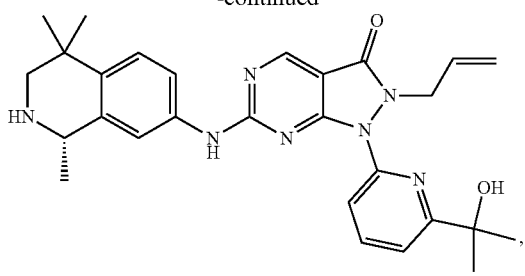
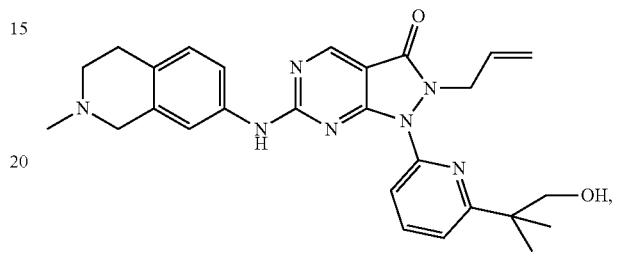
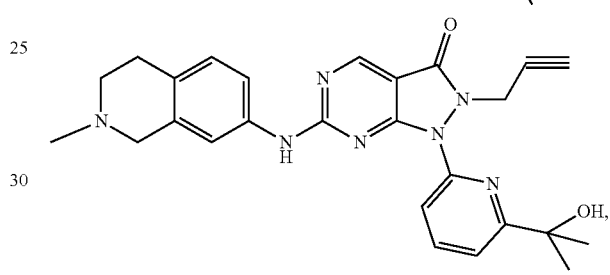
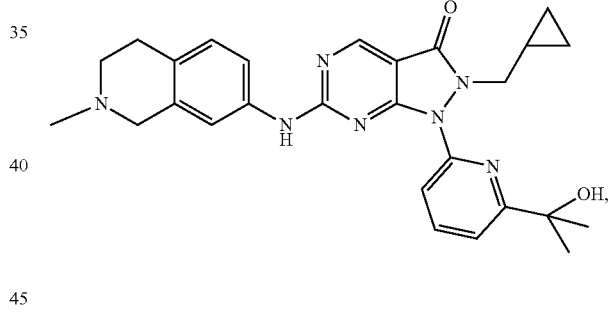
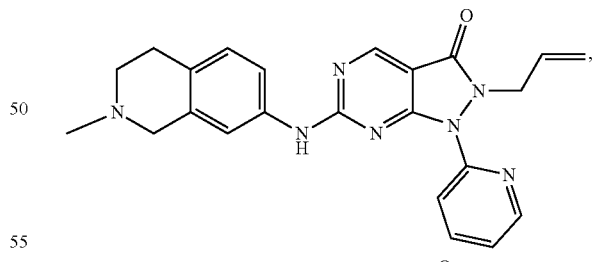
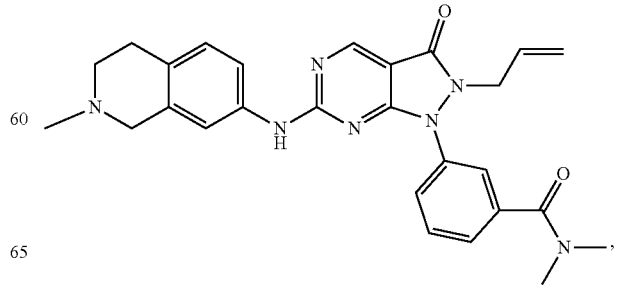

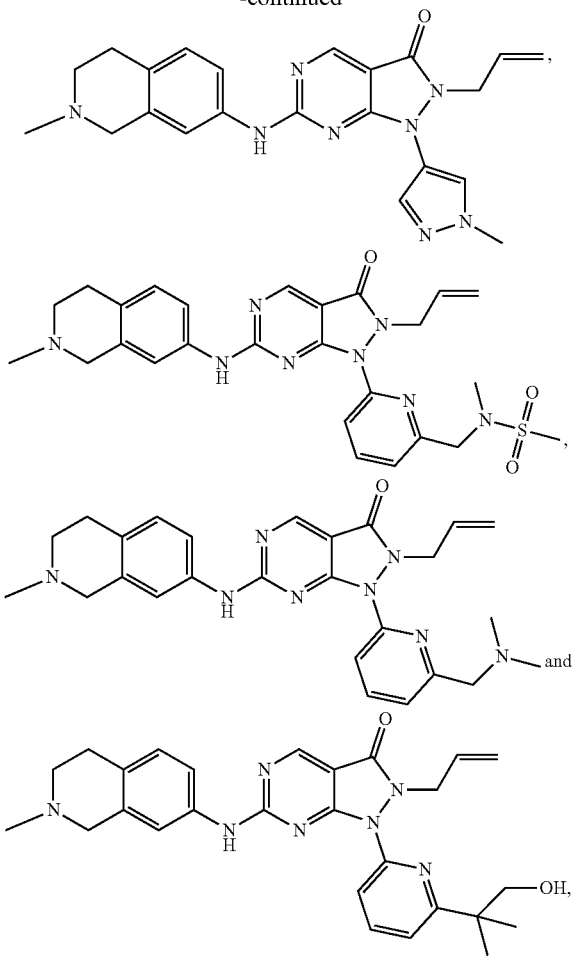

or a pharmaceutically acceptable salt of any of the foregoing.

19. A pharmaceutical composition comprising an effective amount of the compound of claim 1, or a pharmaceutically acceptable salt thereof, and a pharmaceutically acceptable carrier, diluent, excipient or combination thereof.

20. A method for ameliorating or treating a cancer comprising administering an effective amount of a compound of claim 1, or a pharmaceutically acceptable salt thereof, to a subject having the cancer, wherein the cancer is selected from a brain cancer, a cervicocerebral cancer, an esophageal cancer, a thyroid cancer, a small cell cancer, a non-small cell cancer, a breast cancer, a lung cancer, a stomach cancer, a gallbladder/bile duct cancer, a liver cancer, a pancreatic cancer, a colon cancer, a rectal cancer, an ovarian cancer, a choriocarcinoma, an uterus body cancer, an uterocervical cancer, a renal pelvis/ureter cancer, a bladder cancer, a prostate cancer, a penis cancer, a testicular cancer, a fetal cancer, Wilms' cancer, a skin cancer, malignant melanoma, a neuroblastoma, an osteosarcoma, an Ewing's tumor, a soft part sarcoma, an acute leukemia, a chronic lymphatic leukemia, a chronic myelocytic leukemia, polycythemia vera, a malignant lymphoma, multiple myeloma, a Hodgkin's lymphoma, and a non-Hodgkin's lymphoma.

21. A method for inhibiting replication of a malignant growth or a tumor comprising contacting the growth or the tumor with an effective amount of a compound of claim 1, or a pharmaceutically acceptable salt thereof, wherein the malignant growth or tumor is due to a cancer selected from a brain cancer, a cervicocerebral cancer, an esophageal cancer, a thyroid cancer, a small cell cancer, a non-small cell cancer, a breast cancer, a lung cancer, a stomach cancer, a gallbladder/bile duct cancer, a liver cancer, a pancreatic cancer, a colon cancer, a rectal cancer, an ovarian cancer, a choriocarcinoma, an uterus body cancer, an uterocervical cancer, a renal pelvis/ureter cancer, a bladder cancer, a prostate cancer, a penis cancer, a testicular cancer, a fetal cancer, Wilms' cancer, a skin cancer, malignant melanoma, a neuroblastoma, an osteosarcoma, an Ewing's tumor, a soft part sarcoma, an acute leukemia, a chronic lymphatic leukemia, a chronic myelocytic leukemia, polycythemia vera, a malignant lymphoma, multiple myeloma, a Hodgkin's lymphoma, and a non-Hodgkin's lymphoma.

22. A method for inhibiting the activity of WEE1 comprising providing an effective amount of a compound of claim 1, or a pharmaceutically acceptable salt thereof, to a cancer cell, wherein the cancer cell is from a cancer selected from a brain cancer, a cervicocerebral cancer, an esophageal cancer, a thyroid cancer, a small cell cancer, a non-small cell cancer, a breast cancer, a lung cancer, a stomach cancer, a gallbladder/bile duct cancer, a liver cancer, a pancreatic cancer, a colon cancer, a rectal cancer, an ovarian cancer, a choriocarcinoma, an uterus body cancer, an uterocervical cancer, a renal pelvis/ureter cancer, a bladder cancer, a prostate cancer, a penis cancer, a testicular cancer, a fetal cancer, Wilms' cancer, a skin cancer, malignant melanoma, a neuroblastoma, an osteosarcoma, an Ewing's tumor, a soft part sarcoma, an acute leukemia, a chronic lymphatic leukemia, a chronic myelocytic leukemia, polycythemia vera, a malignant lymphoma, multiple myeloma, a Hodgkin's lymphoma, and a non-Hodgkin's lymphoma.

* * * * *